US011780890B2

(12) United States Patent
Kelly et al.

(10) Patent No.: US 11,780,890 B2
(45) Date of Patent: Oct. 10, 2023

(54) PESTICIDAL GENES AND METHODS OF USE

(71) Applicant: AGBIOME, INC., Durham, NC (US)

(72) Inventors: Rebekah Deter Kelly, Durham, NC (US); Jessica Parks, Apex, NC (US); Rebecca E. Thayer, Morrisville, NC (US); Francois Torney, Mahomet, IL (US)

(73) Assignee: AgBiome, Inc., Durham, NC (US)

( * ) Notice: Subject to any disclaimer, the term of this patent is extended or adjusted under 35 U.S.C. 154(b) by 0 days.

(21) Appl. No.: 17/534,792

(22) Filed: Nov. 24, 2021

(65) Prior Publication Data

US 2022/0162269 A1  May 26, 2022

Related U.S. Application Data

(60) Provisional application No. 63/140,058, filed on Jan. 21, 2021, provisional application No. 63/117,797, filed on Nov. 24, 2020.

(51) Int. Cl.
| C07K 14/195 | (2006.01) |
| A01N 63/50 | (2020.01) |
| A01P 7/04 | (2006.01) |
| C12N 15/82 | (2006.01) |

(52) U.S. Cl.
CPC ............ C07K 14/195 (2013.01); A01N 63/50 (2020.01); A01P 7/04 (2021.08); C12N 15/8286 (2013.01)

(58) Field of Classification Search
CPC ......... C07K 14/195; A01N 63/50; A01P 7/04; C12N 15/8286
See application file for complete search history.

(56) References Cited

U.S. PATENT DOCUMENTS

| 5,240,842 | A | 8/1993 | Mets |
| 7,473,822 | B1 | 1/2009 | Paz et al. |
| 10,947,556 | B2 | 3/2021 | Beilinson et al. |
| 2016/0355842 | A1 | 12/2016 | Parks et al. |
| 2017/0137842 | A1* | 5/2017 | Bowen et al. ....... C07K 14/325 |
| 2019/0284571 | A1 | 9/2019 | Parks et al. |

FOREIGN PATENT DOCUMENTS

| WO | WO 01/38514 | 5/2001 |
| WO | WO 2015/023846 | 2/2015 |
| WO | WO 2017/030808 | 2/2017 |

OTHER PUBLICATIONS

Huynh et al., "Development of an improved and accessible diet for western corn rootworm larvae using response surface modeling," 2019, Sci Rep, 9:16009 (9 pp).
Ludwick et al., "A new artificial diet for western corn rootworm larvae is compatible with and detects resistance to all current Bt toxins," 2018, Sci Rep, 8:5379 (10 pp).
Marrone et al., "Improvements in Laboratory Rearing of the Southern Corn Rootworm, *Diabrotica undecimpuncta howardi* Barber (Coleoptera: Chrysomelidae), on an Artificial Diet and Corn," 1985, J Econ Entomol, 78:290-293.
NCBI WP_087094398.1, "ETX/MTX2 family pore-forming toxin [Bacillus cytotoxicus]," Jul. 29, 2021, 2 pp.
NCBI WP_098259338.1, "Etx/MTX2 family pore-forming toxin [Bacillus cereus]," Jul. 29, 2021, 2 pp.
NCBI WP_098873554.1, "ETX/MTX2 family pore-forming toxin [Bacillus cereus]," Jul. 29, 2021, 2 pp.
Hayakawa et al., "Cry46Ab from *Bacillus thuringiensis* Tk-E6 is a new mosquitocidal toxin with aerolysin-type architecture," Insects Biochemistry and Molecular Biology, 2017, 87:100-106 (abstract only).
UniProtKB, Accession No. A0A1D9LBV6, Feb. 15, 2017.
Vöing et al., "Draft Genome Sequence of *Chromobacterium vaccinii*, a Potential Biocontrol Agent against Mosquito (*Aedes aegypti*) Larvae," Genome Announcements, 2015, 3(3):e00477-15 (2 pp).
Wei et al., "A selective insecticidal protein from *Pseudomonas mosselii* for corn rootworm control," Plant Biotechnology Journal, 2018, 16(2):649-649.
Xu et al., "Crystal structure of CRY51Aa1: a potential novel insecticidal aerolysin-type [Beta]-pore-forming toxin from *Bacillus thuringiensis*," May 7, 2015, 462(3):184-189.

(Continued)

*Primary Examiner* — Matthew R Keogh
*Assistant Examiner* — Rebecca Stephens
(74) *Attorney, Agent, or Firm* — Womble Bond Dickinson (US) LLP

(57) ABSTRACT

Compositions having pesticidal activity and methods for their use are provided. Compositions include isolated and recombinant polypeptide sequences having pesticidal activity, recombinant and synthetic nucleic acid molecules encoding the pesticidal polypeptides, DNA constructs comprising the nucleic acid molecules, vectors comprising the nucleic acid molecules, host cells comprising the vectors, and antibodies to the pesticidal polypeptides. Nucleotide sequences encoding the polypeptides provided herein can be used in DNA constructs or expression cassettes for transformation and expression in organisms of interest. The compositions and methods provided herein are useful for the production of organisms with enhanced pest resistance or tolerance. Transgenic plants and seeds comprising a nucleotide sequence that encodes a pesticidal protein of the invention are also provided. Methods are provided for producing the polypeptides disclosed herein, and for using those polypeptides for controlling a pest. Methods and kits for detecting polypeptides of the invention in a sample are also included.

35 Claims, No Drawings
Specification includes a Sequence Listing.

(56) References Cited

OTHER PUBLICATIONS

Yonglei et al., "Cry64Ba and Cry64Ca, Two ETX/MTX2-Type *Bacillius thuringiensis* Insecticidal Proteins Active against Hemipteran Pests," Appl Environ Microbiol, Feb. 2018, 84(3):e01996-17 (11 pp).

* cited by examiner

SEQUENCE LISTING

<160> NUMBER OF SEQ ID NOS: 40

<210> SEQ ID NO 1
<211> LENGTH: 798
<212> TYPE: DNA
<213> ORGANISM: Raoultella ornithinolytica

<400> SEQUENCE: 1

```
atgcattctg aagatattaa agaaaaaaca cttacctggt ttaactacat taccagtccg      60
gtaaataatg aagatgtatt tatgcgaagc tcacaggata tacttgttat gaatcctgcg     120
atagcagctg caacgcaaga gtatatcgat ggaaatactc acgatagtca gctattcaac     180
acaccatcat cagcgcctca aacgatgttt gatggcctgc aaaccattgt aaacctttgc     240
cgtgtgcaat caggttataa tgcacttgat cctaatggaa ccggaagtaa ggcgtatttt     300
acgaaattta ctcagaacat agcaaatgtt ccgtgcctga cgttgttgag tgcggaaaca     360
aaaaatatta aacaacaaag ccataatgca gatgagctca tcaactcatt tgtcgatgct     420
tttgatgggc ttacacaaag cgaccagtct aagattaagt catccgtaac ctcgttagta     480
aaagcagccc tgagctatgc aaatgaagat cagaaatcat caaatttcac gcaaaatatt     540
ttgcaaaccg gtgatgatca ggtgatattc acgttgtatg ccagtacatt tgaaatttct     600
tcgaccaaaa gcaaaggtgt tatatctttt aaatccgaat actcattgca gcaggcgtta     660
tatagccttt cccgcgcaag ctgggaacgg gtgaaagatc tgtttgctga acaagaaaaa     720
actactatgg atcagtggtt aaatgatatg aaaacgccac agaaaagtgg cagtacagta     780
aaagcattat gtttagaa                                                  798
```

<210> SEQ ID NO 2
<211> LENGTH: 266
<212> TYPE: PRT
<213> ORGANISM: Raoultella ornithinolytica

<400> SEQUENCE: 2

Met His Ser Glu Asp Ile Lys Glu Lys Thr Leu Thr Trp Phe Asn Tyr
1               5                   10                  15

Ile Thr Ser Pro Val Asn Asn Glu Asp Val Phe Met Arg Ser Ser Gln
            20                  25                  30

```
Asp Ile Leu Val Met Asn Pro Ala Ile Ala Ala Ala Thr Gln Glu Tyr
            35                  40                  45
Ile Asp Gly Asn Thr His Asp Ser Gln Leu Phe Asn Thr Pro Ser Ser
 50                  55                  60
Ala Pro Gln Thr Met Phe Asp Gly Leu Gln Thr Ile Val Asn Leu Cys
 65                  70                  75                  80
Arg Val Gln Ser Gly Tyr Asn Ala Leu Asp Pro Asn Gly Thr Gly Ser
                 85                  90                  95
Lys Ala Tyr Phe Thr Lys Phe Thr Gln Asn Ile Ala Asn Val Pro Cys
            100                 105                 110
Leu Thr Leu Leu Ser Ala Glu Thr Lys Asn Ile Lys Gln Gln Ser His
            115                 120                 125
Asn Ala Asp Glu Leu Ile Asn Ser Phe Val Asp Ala Phe Asp Gly Leu
130                 135                 140
Thr Gln Ser Asp Gln Ser Lys Ile Lys Ser Ser Val Thr Ser Leu Val
145                 150                 155                 160
Lys Ala Ala Leu Ser Tyr Ala Asn Glu Asp Gln Lys Ser Ser Asn Phe
                165                 170                 175
Thr Gln Asn Ile Leu Gln Thr Gly Asp Asp Gln Val Ile Phe Thr Leu
            180                 185                 190
Tyr Ala Ser Thr Phe Glu Ile Ser Ser Thr Lys Ser Lys Gly Val Ile
            195                 200                 205
Ser Phe Lys Ser Glu Tyr Ser Leu Gln Gln Ala Leu Tyr Ser Leu Ser
            210                 215                 220
Arg Ala Ser Trp Glu Arg Val Lys Asp Leu Phe Ala Glu Gln Glu Lys
225                 230                 235                 240
Thr Thr Met Asp Gln Trp Leu Asn Asp Met Lys Thr Pro Gln Lys Ser
                245                 250                 255
Gly Ser Thr Val Lys Ala Leu Cys Leu Glu
            260                 265

<210> SEQ ID NO 3
<211> LENGTH: 1311
<212> TYPE: DNA
<213> ORGANISM: Chryseobacterium sp.

<400> SEQUENCE: 3
atgaaattga taaaagccac gcttcccgct tcaatattgc tcattgcttg ccagcagcag      60
gcatgggcgg cagataccgt gccacaattc agcgacgtgg tgtatacgga gatgtccccg     120
gataatgagt ccaccattca gaaaattgtg acgtcggacg cattttttcaa ccatgggcg     180 ttactggcgc attatctcgg ttatggctgg gtaggcggca ataccaacgg caataccgcc     240
gtgggcaagg agtttgaata ccggcgcatc gacaccatgc tggataatct gtcgatgccc     300
gacaataaat accgctacat gatgaatgcc aagtacgatc cgaaggggcc gggcgggtat     360
tgggcggaca gcgtttccg catggccttt tccaacatcc agtggatgat ggaaccggac     420
gacatgaaac tggctcgcc ggagctgtat aacaagaaac cgctgaaagt ggtgacggtg     480
gtgctggaaa tcacagcga ccagtccgac accggcgtgg ccaacctgaa atacgattcc     540
acggtcagtt ggtccaaagc cgacaagatc agcgtcagcg gcaaggtgac gatgaccaac     600
aagtggacgg gcggtctgcc gctgatcggc ggggcggaaa cctcggtagc ggtagagatc     660
gcttccgggg cggactggac caccaccaac ggcaccagca gcaccacttc gcaaacggcg     720
gagtaccggg cggtgttgcc gcccaagagc aaacgcctga tcacgctgac gctgttcgag     780
```

-continued

```
cagaaagcca atattcccta tacctccaag atgttcctga cttacgaggc ggagctgtac    840
aacttcctgc gctacagcga caacgcgctg aacggccatc cgtccaaccg tccgttttat    900
ctgagcaagt tcggcggcaa ggacggcctg aacggcgcgc aggatctgct gtcgcaatac    960
ctgaatccgg cgacgtcgaa atgggattgg ccgtgggcgg tgaaccagta ctcgcgaagc   1020
accatcgagt actacatcgg ctcgatttcc aaacgcaagt tcaagcagca gttcaccggg   1080
gtcttcagcg cggtggactc cacggcctac accatcacgg ccggtccggt ggaaccgctg   1140
agcgcgcagg cgcagaccgc ccgctcggcc agcctgggcg cggcggcctc cggcggaatc   1200
cagtatcgcg tggtgagcgg ggacctgaag gatgtgccgg ccgcttgaa gaacctgcgc    1260 ttcacagtgg gcaagccgca ggctgcgcca tccgccgcat cgccgatccg g            1311
```

<210> SEQ ID NO 4
<211> LENGTH: 437
<212> TYPE: PRT
<213> ORGANISM: Chryseobacterium sp.

<400> SEQUENCE: 4

```
Met Lys Leu Ile Lys Ala Thr Leu Pro Ala Ser Ile Leu Leu Ile Ala
1               5                   10                  15

Cys Gln Gln Gln Ala Trp Ala Ala Asp Thr Val Pro Gln Phe Ser Asp
            20                  25                  30

Val Val Tyr Thr Glu Met Ser Pro Asp Asn Glu Ser Thr Ile Gln Lys
        35                  40                  45

Ile Val Thr Ser Asp Ala Phe Phe Lys Pro Trp Ala Leu Leu Ala His
    50                  55                  60

Tyr Leu Gly Tyr Gly Trp Val Gly Gly Asn Thr Asn Gly Asn Thr Ala
65                  70                  75                  80

Val Gly Lys Glu Phe Glu Tyr Arg Arg Ile Asp Thr Met Leu Asp Asn
                85                  90                  95

Leu Ser Met Pro Asp Asn Lys Tyr Arg Tyr Met Met Asn Ala Lys Tyr
            100                 105                 110

Asp Pro Lys Gly Pro Gly Gly Tyr Trp Ala Asp Lys Arg Phe Arg Met
        115                 120                 125

Ala Phe Ser Asn Ile Gln Trp Met Met Glu Pro Asp Asp Met Lys Leu
    130                 135                 140

Gly Ser Pro Glu Leu Tyr Asn Lys Lys Pro Leu Lys Val Val Thr Val
145                 150                 155                 160

Val Leu Glu Asn His Ser Asp Gln Ser Asp Thr Gly Val Ala Asn Leu
                165                 170                 175

Lys Tyr Asp Ser Thr Val Ser Trp Ser Lys Ala Asp Lys Ile Ser Val
            180                 185                 190

Ser Gly Lys Val Thr Met Thr Asn Lys Trp Thr Gly Gly Leu Pro Leu
        195                 200                 205

Ile Gly Gly Ala Glu Thr Ser Val Ala Val Glu Ile Ala Ser Gly Ala
    210                 215                 220

Asp Trp Thr Thr Thr Asn Gly Thr Ser Ser Thr Ser Gln Thr Ala
225                 230                 235                 240

Glu Tyr Arg Ala Val Leu Pro Pro Lys Ser Lys Arg Leu Ile Thr Leu
                245                 250                 255

Thr Leu Phe Glu Gln Lys Ala Asn Ile Pro Tyr Thr Ser Lys Met Phe
            260                 265                 270

Leu Thr Tyr Glu Ala Glu Leu Tyr Asn Phe Leu Arg Tyr Ser Asp Asn
        275                 280                 285
```

Ala Leu Asn Gly His Pro Ser Asn Arg Pro Phe Tyr Leu Ser Lys Phe
        290                 295                 300

Gly Gly Lys Asp Gly Leu Asn Gly Ala Gln Asp Leu Leu Ser Gln Tyr
305                 310                 315                 320

Leu Asn Pro Ala Thr Ser Lys Trp Asp Trp Pro Trp Ala Val Asn Gln
                325                 330                 335

Tyr Ser Arg Ser Thr Ile Glu Tyr Tyr Ile Gly Ser Ile Ser Lys Arg
                340                 345                 350

Lys Phe Lys Gln Gln Phe Thr Gly Val Phe Ser Ala Val Asp Ser Thr
        355                 360                 365

Ala Tyr Thr Ile Thr Ala Gly Pro Val Glu Pro Leu Ser Ala Gln Ala
        370                 375                 380

Gln Thr Ala Arg Ser Ala Ser Leu Gly Ala Ala Ala Ser Gly Gly Ile
385                 390                 395                 400

Gln Tyr Arg Val Val Ser Gly Asp Leu Lys Asp Val Pro Gly Arg Leu
                405                 410                 415

Lys Asn Leu Arg Phe Thr Val Gly Lys Pro Gln Ala Ala Pro Ser Ala
                420                 425                 430

Ala Ser Pro Ile Arg
        435

<210> SEQ ID NO 5
<211> LENGTH: 1245
<212> TYPE: DNA
<213> ORGANISM: Artificial Sequence
<220> FEATURE:
<223> OTHER INFORMATION: Synthetic polynucleotide

<400> SEQUENCE: 5
atggcagata ccgtgccaca attcagcgac gtggtgtata cggagatgtc cccggataat      60
gagtccacca ttcagaaaat tgtgacgtcg gacgcatttt tcaaaccatg ggcgttactg     120
gcgcattatc tcggttatgg ctgggtaggc ggcaatacca acggcaatac cgccgtgggc     180
aaggagtttg aataccggcg catcgacacc atgctggata tctgtcgat gcccgacaat      240 aaataccgct acatgatgaa tgccaagtac gatccgaagg ggccgggcgg gtattgggcg     300
gacaagcgtt tccgcatggc cttttccaac atccagtgga tgatggaacc ggacgacatg     360
aaactgggct cgccggagct gtataacaag aaaccgctga agtggtgac ggtggtgctg      420 gaaaatcaca gcgaccagtc cgacaccggc gtggccaacc tgaaatacga ttccacggtc     480
agttggtcca agccgacaa gatcagcgtc agcggcaagg tgacgatgac caacaagtgg      540
acgggcggtc tgccgctgat cggcggggcg gaaacctcgg tagcggtaga gatcgcttcc     600
ggggcggact ggaccaccac caacggcacc agcagcacca cttcgcaaac ggcggagtac     660
cgggcggtgt gccgcccaa gagcaaacgc ctgatcacgc tgacgctgtt cgagcagaaa      720
gccaatattc cctatacctc caagatgttc ctgacttacg aggcggagct gtacaacttc     780
ctgcgctaca gcgacaacgc gctgaacggc catccgtcca accgtccgtt ttatctgagc     840
aagttcggcg gcaaggacgg cctgaacggc gcgcaggatc tgctgtcgca atacctgaat     900
ccggcgacgt cgaaatggga ttggccgtgg gcggtgaaca gtactcgcg aagcaccatc      960 gagtactaca tcggctcgat ttccaaacgc aagttcaagc agcagttcac cggggtcttc    1020
agcgcggtgg actccacggc ctacaccatc acggccggtc cggtggaacc gctgagcgcg    1080
caggcgcaga ccgcccgctc ggccagcctg ggcgcggcgg cctccggcgg aatccagtat    1140

-continued

```
cgcgtggtga gcggggacct gaaggatgtg ccgggccgct tgaagaacct gcgcttcaca    1200
gtgggcaagc cgcaggctgc gccatccgcc gcatcgccga tccgg                    1245
```

<210> SEQ ID NO 6
<211> LENGTH: 415
<212> TYPE: PRT
<213> ORGANISM: Artificial Sequence
<220> FEATURE:
<223> OTHER INFORMATION: Synthetic polypeptide

<400> SEQUENCE: 6

```
Met Ala Asp Thr Val Pro Gln Phe Ser Asp Val Val Tyr Thr Glu Met
1               5                   10                  15

Ser Pro Asp Asn Glu Ser Thr Ile Gln Lys Ile Val Thr Ser Asp Ala
            20                  25                  30

Phe Phe Lys Pro Trp Ala Leu Leu Ala His Tyr Leu Gly Tyr Gly Trp
        35                  40                  45

Val Gly Gly Asn Thr Asn Gly Asn Thr Ala Val Gly Lys Glu Phe Glu
    50                  55                  60

Tyr Arg Arg Ile Asp Thr Met Leu Asp Asn Leu Ser Met Pro Asp Asn
65                  70                  75                  80

Lys Tyr Arg Tyr Met Met Asn Ala Lys Tyr Asp Pro Lys Gly Pro Gly
                85                  90                  95

Gly Tyr Trp Ala Asp Lys Arg Phe Arg Met Ala Phe Ser Asn Ile Gln
            100                 105                 110

Trp Met Met Glu Pro Asp Asp Met Lys Leu Gly Ser Pro Glu Leu Tyr
        115                 120                 125

Asn Lys Lys Pro Leu Lys Val Val Thr Val Val Leu Glu Asn His Ser
    130                 135                 140

Asp Gln Ser Asp Thr Gly Val Ala Asn Leu Lys Tyr Asp Ser Thr Val
145                 150                 155                 160

Ser Trp Ser Lys Ala Asp Lys Ile Ser Val Ser Gly Lys Val Thr Met
                165                 170                 175

Thr Asn Lys Trp Thr Gly Gly Leu Pro Leu Ile Gly Gly Ala Glu Thr
            180                 185                 190

Ser Val Ala Val Glu Ile Ala Ser Gly Ala Asp Trp Thr Thr Thr Asn
        195                 200                 205

Gly Thr Ser Ser Thr Ser Gln Thr Ala Glu Tyr Arg Ala Val Leu
    210                 215                 220

Pro Pro Lys Ser Lys Arg Leu Ile Thr Leu Thr Leu Phe Glu Gln Lys
225                 230                 235                 240

Ala Asn Ile Pro Tyr Thr Ser Lys Met Phe Leu Thr Tyr Glu Ala Glu
                245                 250                 255

Leu Tyr Asn Phe Leu Arg Tyr Ser Asp Asn Ala Leu Asn Gly His Pro
            260                 265                 270

Ser Asn Arg Pro Phe Tyr Leu Ser Lys Phe Gly Gly Lys Asp Gly Leu
        275                 280                 285

Asn Gly Ala Gln Asp Leu Leu Ser Gln Tyr Leu Asn Pro Ala Thr Ser
    290                 295                 300

Lys Trp Asp Trp Pro Trp Ala Val Asn Gln Tyr Ser Arg Ser Thr Ile
305                 310                 315                 320

Glu Tyr Tyr Ile Gly Ser Ile Ser Lys Arg Lys Phe Lys Gln Gln Phe
                325                 330                 335

Thr Gly Val Phe Ser Ala Val Asp Ser Thr Ala Tyr Thr Ile Thr Ala
            340                 345                 350
```

Gly Pro Val Glu Pro Leu Ser Ala Gln Ala Gln Thr Ala Arg Ser Ala
            355                 360                 365

Ser Leu Gly Ala Ala Ala Ser Gly Gly Ile Gln Tyr Arg Val Val Ser
        370                 375                 380

Gly Asp Leu Lys Asp Val Pro Gly Arg Leu Lys Asn Leu Arg Phe Thr
385                 390                 395                 400

Val Gly Lys Pro Gln Ala Ala Pro Ser Ala Ala Ser Pro Ile Arg
                405                 410                 415

<210> SEQ ID NO 7
<211> LENGTH: 996
<212> TYPE: DNA
<213> ORGANISM: Chryseobacterium sp.

<400> SEQUENCE: 7
atgattaaaa tgattaaaaa aatcaattct ttttggtttc tcttgttgat gctttcggta      60
tcgtgttcaa gggatgaagt gagtgctatt aatgatgatt cagaaaaggt aaattattct     120
gaagtaaaga aagtacagct gacggaagct gaaatgctgc agaaaggctg gaaaattgta     180
gaccagttta aattatcaga tcaaaataat ctgggtgtaa aagttcgac caatgaagag      240 cgtgaaatcc ctttcaagcc taaccatttg aaagatatag gatatgatat cagttttcc     300 ggtgaaaaaa cgaggttaaa aaatgttttt gcctacgccg ccaggttcc ggatggaatt      360 atatttaatc ctgatctttc tgtagatgga gatacccgga atacagcccc caatccaaat     420
gtttctattg ttttagggac accacaggta acaataaaaa ctgacggagt agatttaccg     480
gataatgctt atactacgga agctattaat aacggagatc gtgaaagtga aattacggtg     540
tcttattctt acaaaaaagg atattcaact tcgtggaaac gtacggtctc agggtcattt     600
gaggtagcag catcagtatc cgttgatatt ccgttggttg caaaagcttc agcaagtact     660
aaagttgttg taggtggaga tacaacggaa ggtacagaaa attctgagga aattacagaa     720
accagtacct ataagactat tgttccggca cactccaaaa agacaatttc tatcctgacg     780
aaattaaaag gatcttctgt agaatacttt gtgcctatga gttgaacgg aagattgcag      840 gccaactttc cttctccggc caatggccat tattattggg cttttcctat cgaaaacttc     900
cctgattttc tttctactat acacggagaa tccggtactg tgaagtcggt cagcaatgta     960
agtgttacgg ttctggaatc gcctgcacaa gctata                               996

<210> SEQ ID NO 8
<211> LENGTH: 332
<212> TYPE: PRT
<213> ORGANISM: Chryseobacterium sp.

<400> SEQUENCE: 8

Met Ile Lys Met Ile Lys Lys Ile Asn Ser Phe Trp Phe Leu Leu Leu
1               5                   10                  15

Met Leu Ser Val Ser Cys Ser Arg Asp Glu Val Ser Ala Ile Asn Asp
            20                  25                  30

Asp Ser Glu Lys Val Asn Tyr Ser Glu Val Lys Lys Val Gln Leu Thr
        35                  40                  45

Glu Ala Glu Met Leu Gln Lys Gly Trp Lys Ile Val Asp Gln Phe Lys
    50                  55                  60

Leu Ser Asp Gln Asn Asn Leu Gly Val Lys Ser Ser Thr Asn Glu Glu
65                  70                  75                  80

Arg Glu Ile Pro Phe Lys Pro Asn His Leu Lys Asp Ile Gly Tyr Asp

```
                        85                  90                  95
Ile Ser Phe Ser Gly Glu Lys Thr Arg Leu Lys Asn Val Phe Ala Tyr
            100                 105                 110

Ala Gly Gln Val Pro Asp Gly Ile Ile Phe Asn Pro Asp Leu Ser Val
        115                 120                 125

Asp Gly Asp Thr Arg Asn Thr Ala Pro Asn Pro Asn Val Ser Ile Val
    130                 135                 140

Leu Gly Thr Pro Gln Val Thr Ile Lys Thr Asp Gly Val Asp Leu Pro
145                 150                 155                 160

Asp Asn Ala Tyr Thr Thr Glu Ala Ile Asn Asn Gly Asp Arg Glu Ser
                165                 170                 175

Glu Ile Thr Val Ser Tyr Ser Tyr Lys Lys Gly Tyr Ser Thr Ser Trp
            180                 185                 190

Lys Arg Thr Val Ser Gly Ser Phe Glu Val Ala Ala Ser Val Ser Val
        195                 200                 205

Asp Ile Pro Leu Val Ala Lys Ala Ser Ala Ser Thr Lys Val Val Val
    210                 215                 220

Gly Gly Asp Thr Thr Glu Gly Thr Glu Asn Ser Glu Glu Ile Thr Glu
225                 230                 235                 240

Thr Ser Thr Tyr Lys Thr Ile Val Pro Ala His Ser Lys Lys Thr Ile
                245                 250                 255

Ser Ile Leu Thr Lys Leu Lys Gly Ser Ser Val Glu Tyr Phe Val Pro
            260                 265                 270

Met Lys Leu Asn Gly Arg Leu Gln Ala Asn Phe Pro Ser Pro Ala Asn
        275                 280                 285

Gly His Tyr Tyr Trp Ala Phe Pro Ile Glu Asn Phe Pro Asp Phe Leu
    290                 295                 300

Ser Thr Ile His Gly Glu Ser Gly Thr Val Lys Ser Val Ser Asn Val
305                 310                 315                 320

Ser Val Thr Val Leu Glu Ser Pro Ala Gln Ala Ile
                325                 330

<210> SEQ ID NO 9
<211> LENGTH: 987
<212> TYPE: DNA
<213> ORGANISM: Artificial Sequence
<220> FEATURE:
<223> OTHER INFORMATION: Synthetic polynucleotide

<400> SEQUENCE: 9
atgattaaaa aaatcaattc ttttggtttt ctcttgttga tgctttcggt atcgtgttca    60
agggatgaag tgagtgctat taatgatgat tcagaaaagg taaattattc tgaagtaaag   120
aaagtacagc tgacggaagc tgaaatgctg cagaaaggct ggaaaattgt agaccagttt   180
aaattatcag atcaaaataa tctgggtgta aaaagttcga ccaatgaaga gcgtgaaatc   240
cctttcaagc ctaaccattt gaaagatata ggatatgata tcagttttc cggtgaaaaa   300 acgaggttaa aaaatgtttt tgcctacgcc ggccaggttc cggatggaat tatatttaat   360
cctgatcttt ctgtagatgg agataccccg aatacagccc ccaatccaaa tgtttctatt   420
gttttaggga caccacaggt aacaataaaa actgacggag tagatttacc ggataatgct   480
tatactacgg aagctattaa taacggagat cgtgaaagtg aaattacggt gtcttattct   540
tacaaaaaag gatattcaac ttcgtggaaa cgtacggtct cagggtcatt tgaggtagca   600
gcatcagtat ccgttgatat tccgttggtt gcaaaagctt cagcaagtac taaagttgtt   660
```

```
gtaggtggag atacaacgga aggtacagaa aattctgagg aaattacaga aaccagtacc    720
tataagacta ttgttccggc acactccaaa aagacaattt ctatcctgac gaaattaaaa    780
ggatcttctg tagaatactt tgtgcctatg aagttgaacg gaagattgca ggccaacttt    840
ccttctccgg ccaatggcca ttattattgg gcttttccta tcgaaaactt ccctgatttt    900
ctttctacta tacacggaga atccggtact gtgaagtcgg tcagcaatgt aagtgttacg    960
gttctggaat cgcctgcaca agctata                                        987
```

<210> SEQ ID NO 10
<211> LENGTH: 329
<212> TYPE: PRT
<213> ORGANISM: Artificial Sequence
<220> FEATURE:
<223> OTHER INFORMATION: Synthetic polypeptide

<400> SEQUENCE: 10

```
Met Ile Lys Lys Ile Asn Ser Phe Trp Phe Leu Leu Met Leu Ser
1               5                   10                  15

Val Ser Cys Ser Arg Asp Glu Val Ser Ala Ile Asn Asp Ser Glu
                20                  25                  30

Lys Val Asn Tyr Ser Glu Val Lys Lys Val Gln Leu Thr Glu Ala Glu
            35                  40                  45

Met Leu Gln Lys Gly Trp Lys Ile Val Asp Gln Phe Lys Leu Ser Asp
        50                  55                  60

Gln Asn Asn Leu Gly Val Lys Ser Ser Thr Asn Glu Glu Arg Glu Ile
65                  70                  75                  80

Pro Phe Lys Pro Asn His Leu Lys Asp Ile Gly Tyr Asp Ile Ser Phe
                85                  90                  95

Ser Gly Glu Lys Thr Arg Leu Lys Asn Val Phe Ala Tyr Ala Gly Gln
            100                 105                 110

Val Pro Asp Gly Ile Ile Phe Asn Pro Asp Leu Ser Val Asp Gly Asp
        115                 120                 125

Thr Arg Asn Thr Ala Pro Asn Pro Asn Val Ser Ile Val Leu Gly Thr
130                 135                 140

Pro Gln Val Thr Ile Lys Thr Asp Gly Val Asp Leu Pro Asp Asn Ala
                145                 150                 155                 160

Tyr Thr Thr Glu Ala Ile Asn Asn Gly Asp Arg Glu Ser Glu Ile Thr
                165                 170                 175

Val Ser Tyr Ser Tyr Lys Lys Gly Tyr Ser Thr Ser Trp Lys Arg Thr
            180                 185                 190

Val Ser Gly Ser Phe Glu Val Ala Ala Ser Val Ser Val Asp Ile Pro
        195                 200                 205

Leu Val Ala Lys Ala Ser Ala Ser Thr Lys Val Val Gly Gly Asp
    210                 215                 220

Thr Thr Glu Gly Thr Glu Asn Ser Glu Glu Ile Thr Glu Thr Ser Thr
225                 230                 235                 240

Tyr Lys Thr Ile Val Pro Ala His Ser Lys Thr Ile Ser Ile Leu
                245                 250                 255

Thr Lys Leu Lys Gly Ser Ser Val Glu Tyr Phe Val Pro Met Lys Leu
            260                 265                 270

Asn Gly Arg Leu Gln Ala Asn Phe Pro Ser Pro Ala Asn Gly His Tyr
        275                 280                 285

Tyr Trp Ala Phe Pro Ile Glu Asn Phe Pro Asp Phe Leu Ser Thr Ile
    290                 295                 300
```

His Gly Glu Ser Gly Thr Val Lys Ser Val Ser Asn Val Ser Val Thr
305                 310                 315                 320

Val Leu Glu Ser Pro Ala Gln Ala Ile
                325

<210> SEQ ID NO 11
<211> LENGTH: 912
<212> TYPE: DNA
<213> ORGANISM: Artificial Sequence
<220> FEATURE:
<223> OTHER INFORMATION: Synthetic polynucleotide

<400> SEQUENCE: 11

```
atgattaatg atgattcaga aaaggtaaat tattctgaag taaagaaagt acagctgacg    60
gaagctgaaa tgctgcagaa aggctggaaa attgtagacc agtttaaatt atcagatcaa   120
aataatctgg gtgtaaaaag ttcgaccaat gaagagcgtg aaatcccttt caagcctaac   180
catttgaaag atataggata tgatatcagt ttttccggtg aaaaaacgag gttaaaaaat   240 gttttttgcct acgccggcca ggttccggat ggaattatat taatcctga tctttctgta   300 gatggagata cccggaatac agcccccaat ccaaatgttt ctattgtttt agggacacca   360
caggtaacaa taaaaactga cggagtagat ttaccggata atgcttatac tacggaagct   420
attaataacg gagatcgtga aagtgaaatt acggtgtctt attcttacaa aaaggatat   480 tcaacttcgt ggaaacgtac ggtctcaggg tcatttgagg tagcagcatc agtatccgtt   540
gatattccgt tggttgcaaa agcttcagca agtactaaag ttgttgtagg tggagataca   600
acggaaggta cagaaaattc tgaggaaatt acagaaacca gtacctataa gactattgtt   660
ccggcacact ccaaaaagac aatttctatc ctgacgaaat taaaaggatc ttctgtagaa   720
tactttgtgc ctatgaagtt gaacggaaga ttgcaggcca actttccttc ccggccaat   780 ggccattatt attgggcttt tcctatcgaa aacttccctg attttctttc tactatacac   840
ggagaatccg gtactgtgaa gtcggtcagc aatgtaagtg ttacggttct ggaatcgcct   900
gcacaagcta ta                                                      912
```

<210> SEQ ID NO 12
<211> LENGTH: 304
<212> TYPE: PRT
<213> ORGANISM: Artificial Sequence
<220> FEATURE:
<223> OTHER INFORMATION: Synthetic polypeptide

<400> SEQUENCE: 12

Met Ile Asn Asp Asp Ser Glu Lys Val Asn Tyr Ser Glu Val Lys Lys
1               5                   10                  15

Val Gln Leu Thr Glu Ala Glu Met Leu Gln Lys Gly Trp Lys Ile Val
                20                  25                  30

Asp Gln Phe Lys Leu Ser Asp Gln Asn Asn Leu Gly Val Lys Ser Ser
            35                  40                  45

Thr Asn Glu Glu Arg Glu Ile Pro Phe Lys Pro Asn His Leu Lys Asp
        50                  55                  60

Ile Gly Tyr Asp Ile Ser Phe Ser Gly Glu Lys Thr Arg Leu Lys Asn
65                  70                  75                  80

Val Phe Ala Tyr Ala Gly Gln Val Pro Asp Gly Ile Ile Phe Asn Pro
                85                  90                  95

Asp Leu Ser Val Asp Gly Asp Thr Arg Asn Thr Ala Pro Asn Pro Asn
            100                 105                 110

Val Ser Ile Val Leu Gly Thr Pro Gln Val Thr Ile Lys Thr Asp Gly
            115                 120                 125

Val Asp Leu Pro Asp Asn Ala Tyr Thr Thr Glu Ala Ile Asn Asn Gly
        130                 135                 140

Asp Arg Glu Ser Glu Ile Thr Val Ser Tyr Lys Lys Gly Tyr
145                 150                 155                 160

Ser Thr Ser Trp Lys Arg Thr Val Ser Gly Ser Phe Glu Val Ala Ala
                165                 170                 175

Ser Val Ser Val Asp Ile Pro Leu Val Ala Lys Ala Ser Ala Ser Thr
            180                 185                 190

Lys Val Val Val Gly Gly Asp Thr Thr Glu Gly Thr Glu Asn Ser Glu
        195                 200                 205

Glu Ile Thr Glu Thr Ser Thr Tyr Lys Thr Ile Val Pro Ala His Ser
    210                 215                 220

Lys Lys Thr Ile Ser Ile Leu Thr Lys Leu Lys Gly Ser Ser Val Glu
225                 230                 235                 240

Tyr Phe Val Pro Met Lys Leu Asn Gly Arg Leu Gln Ala Asn Phe Pro
                245                 250                 255

Ser Pro Ala Asn Gly His Tyr Tyr Trp Ala Phe Pro Ile Glu Asn Phe
            260                 265                 270

Pro Asp Phe Leu Ser Thr Ile His Gly Glu Ser Gly Thr Val Lys Ser
        275                 280                 285

Val Ser Asn Val Ser Val Thr Val Leu Glu Ser Pro Ala Gln Ala Ile
    290                 295                 300

<210> SEQ ID NO 13
<211> LENGTH: 990
<212> TYPE: DNA
<213> ORGANISM: Chryseobacterium sp.

<400> SEQUENCE: 13
atgatcaaaa aaatcaattc tatttgtatt ctcttattga tgttttcggt atcatgttca      60
agggatgaag tgagtgctat taatgatgat tcagaaaaag taaattattc tgaactaaac    120
aaatcacaga ttacagaggc agagatgctt cagcagggct ggaaaattgt agatgagttt    180
aaattaccag gtaatgatag tctgagaaca aactatagtt catctaatga gagcgtgaa     240
attcctttca gtctaatca tctgaaagac atgggatatg atgtcagtta ttccggagaa    300
agaacgaggt tgaaaaacgt ttttgcttat tccggccagg ttccggatgg aattatattt    360
aatccagacc tttctgtaga tggagatgcc cggaatacag ctccaaaccc aaatgtttcc    420
attgttttgg gaacacctga ggtgactata aaaacagacg gtgcagatct gccggacaat    480
acctatacta cggaagcaat taacaatggc gacagagaaa gtgaaattac ggtaacgtat    540
tcttataaaa aaggatattc tacttcctgg aaacgtactg tatcgggctc atttgaagtg    600
gcagcctcag tatccgttga tattccgctg gttgcaaaag cttcagcaag cacaaaagtt    660
gtggtgggag agatacaac ggaaggtacg gaaaattctg aagaaattac cgaaaccagc    720
agctacaaga ccattgtgcc cgctcattct aaaaaaacga tttctgtcct tacaaaattg    780
aagggatcat ccgttgaata ctttgtaccg atgaaattaa aggaagatt gcaggccaac    840
tttccttcac ctgtagatgg acattattac tgggctttc ctattgaaag cttccctgat    900
tttctttcca atatacacgg agagtcggga attgtaaaat ctgtcagcaa cgtaagtgtt    960
actgtaatgg aatcacctgc gcagaggatt                                      990

```
<210> SEQ ID NO 14
<211> LENGTH: 330
<212> TYPE: PRT
<213> ORGANISM: Chryseobacterium sp.

<400> SEQUENCE: 14
```

| | | | | | | | | | | | | | | |
|---|---|---|---|---|---|---|---|---|---|---|---|---|---|---|
|Met|Ile|Lys|Lys|Ile|Asn|Ser|Ile|Cys|Ile|Leu|Leu|Met|Phe|Ser|
|1| | | |5| | | | |10| | | | |15|
|Val|Ser|Cys|Ser|Arg|Asp|Glu|Val|Ser|Ala|Ile|Asn|Asp|Ser|Glu|
| | | |20| | | | |25| | | | |30| |
|Lys|Val|Asn|Tyr|Ser|Glu|Leu|Asn|Lys|Ser|Gln|Ile|Thr|Glu|Ala|Glu|
| | | | |35| | | | |40| | | | |45| |
|Met|Leu|Gln|Gln|Gly|Trp|Lys|Ile|Val|Asp|Glu|Phe|Lys|Leu|Pro|Gly|
| |50| | | | |55| | | | |60| | | | |
|Asn|Asp|Ser|Leu|Arg|Thr|Asn|Tyr|Ser|Ser|Asn|Glu|Glu|Arg|Glu|
|65| | | | |70| | | | |75| | | | |80|
|Ile|Pro|Phe|Lys|Ser|Asn|His|Leu|Lys|Asp|Met|Gly|Tyr|Asp|Val|Ser|
| | | | |85| | | | |90| | | | |95| |
|Tyr|Ser|Gly|Glu|Arg|Thr|Arg|Leu|Lys|Asn|Val|Phe|Ala|Tyr|Ser|Gly|
| | | |100| | | | |105| | | | |110| | |
|Gln|Val|Pro|Asp|Gly|Ile|Ile|Phe|Asn|Pro|Asp|Leu|Ser|Val|Asp|Gly|
| | | |115| | | | |120| | | | |125| | |
|Asp|Ala|Arg|Asn|Thr|Ala|Pro|Asn|Pro|Asn|Val|Ser|Ile|Val|Leu|Gly|
| |130| | | | |135| | | | |140| | | | |
|Thr|Pro|Glu|Val|Thr|Ile|Lys|Thr|Asp|Gly|Ala|Asp|Leu|Pro|Asp|Asn|
|145| | | | |150| | | | |155| | | | |160|
|Thr|Tyr|Thr|Thr|Glu|Ala|Ile|Asn|Asn|Gly|Asp|Arg|Glu|Ser|Glu|Ile|
| | | | |165| | | | |170| | | | |175| |
|Thr|Val|Thr|Tyr|Ser|Tyr|Lys|Lys|Gly|Tyr|Ser|Thr|Ser|Trp|Lys|Arg|
| | | |180| | | | |185| | | | |190| | |
|Thr|Val|Ser|Gly|Ser|Phe|Glu|Val|Ala|Ala|Ser|Val|Ser|Val|Asp|Ile|
| | | |195| | | | |200| | | | |205| | |
|Pro|Leu|Val|Ala|Lys|Ala|Ser|Ala|Ser|Thr|Lys|Val|Val|Gly|Gly|
| |210| | | | |215| | | | |220| | | | |
|Asp|Thr|Thr|Glu|Gly|Thr|Glu|Asn|Ser|Glu|Glu|Ile|Thr|Glu|Thr|Ser|
|225| | | | |230| | | | |235| | | | |240|
|Ser|Tyr|Lys|Thr|Ile|Val|Pro|Ala|His|Ser|Lys|Lys|Thr|Ile|Ser|Val|
| | | | |245| | | | |250| | | | |255| |
|Leu|Thr|Lys|Leu|Lys|Gly|Ser|Ser|Val|Glu|Tyr|Phe|Val|Pro|Met|Lys|
| | | |260| | | | |265| | | | |270| | |
|Leu|Lys|Gly|Arg|Leu|Gln|Ala|Asn|Phe|Pro|Ser|Pro|Val|Asp|Gly|His|
| | |275| | | | |280| | | | |285| | | |
|Tyr|Tyr|Trp|Ala|Phe|Pro|Ile|Glu|Ser|Phe|Pro|Asp|Phe|Leu|Ser|Asn|
| |290| | | | |295| | | | |300| | | | |
|Ile|His|Gly|Glu|Ser|Gly|Ile|Val|Lys|Ser|Val|Ser|Asn|Val|Ser|Val|
|305| | | | |310| | | | |315| | | | |320|
|Thr|Val|Met|Glu|Ser|Pro|Ala|Gln|Arg|Ile|
| | | | |325| | | | |330|

```
<210> SEQ ID NO 15
<211> LENGTH: 915
<212> TYPE: DNA
<213> ORGANISM: Artificial Sequence
<220> FEATURE:
<223> OTHER INFORMATION: Synthetic polynucleotide

<400> SEQUENCE: 15
```

```
atgattaatg atgattcaga aaaagtaaat tattctgaac taaacaaatc acagattaca      60
gaggcagaga tgcttcagca gggctggaaa attgtagatg agtttaaatt accaggtaat     120
gatagtctga gaacaaacta tagttcatct aatgaagagc gtgaaattcc tttcaagtct     180
aatcatctga agacatggg atatgatgtc agttattccg gagaaagaac gaggttgaaa      240
aacgttttg cttattccgg ccaggttccg gatggaatta tatttaatcc agacctttct      300
gtagatggag atgcccggaa tacagctcca aacccaaatg tttccattgt tttgggaaca    360
cctgaggtga ctataaaaac agacggtgca gatctgccgg acaataccta tactacggaa    420
gcaattaaca atggcgacag agaaagtgaa attacggtaa cgtattctta taaaaaagga    480
tattctactt cctggaaacg tactgtatcg ggctcatttg aagtggcagc ctcagtatcc    540
gttgatattc cgctggttgc aaaagcttca gcaagcacaa agttgtggt gggaggagat     600
acaacggaag gtacggaaaa ttctgaagaa attaccgaaa ccagcagcta caagaccatt    660
gtgcccgctc attctaaaaa aacgatttct gtccttacaa aattgaaggg atcatccgtt    720
gaatactttg taccgatgaa attaaaagga agattgcagg ccaactttcc ttcacctgta    780
gatggacatt attactgggc ttttcctatt gaaagcttcc ctgattttct ttccaatata    840
cacggagagt cgggaattgt aaaatctgtc agcaacgtaa gtgttactgt aatggaatca    900
cctgcgcaga ggatt                                                     915

<210> SEQ ID NO 16
<211> LENGTH: 305
<212> TYPE: PRT
<213> ORGANISM: Artificial Sequence
<220> FEATURE:
<223> OTHER INFORMATION: Synthetic polypeptide

<400> SEQUENCE: 16

Met Ile Asn Asp Asp Ser Glu Lys Val Asn Tyr Ser Glu Leu Asn Lys
1               5                   10                  15

Ser Gln Ile Thr Glu Ala Glu Met Leu Gln Gln Gly Trp Lys Ile Val
            20                  25                  30

Asp Glu Phe Lys Leu Pro Gly Asn Asp Ser Leu Arg Thr Asn Tyr Ser
        35                  40                  45

Ser Ser Asn Glu Glu Arg Glu Ile Pro Phe Lys Ser Asn His Leu Lys
    50                  55                  60

Asp Met Gly Tyr Asp Val Ser Tyr Ser Gly Glu Arg Thr Arg Leu Lys
65                  70                  75                  80

Asn Val Phe Ala Tyr Ser Gly Gln Val Pro Asp Gly Ile Ile Phe Asn
                85                  90                  95

Pro Asp Leu Ser Val Asp Gly Asp Ala Arg Asn Thr Ala Pro Asn Pro
            100                 105                 110

Asn Val Ser Ile Val Leu Gly Thr Pro Glu Val Thr Ile Lys Thr Asp
        115                 120                 125

Gly Ala Asp Leu Pro Asp Asn Thr Tyr Thr Thr Glu Ala Ile Asn Asn
    130                 135                 140

Gly Asp Arg Glu Ser Glu Ile Thr Val Thr Tyr Ser Tyr Lys Lys Gly
145                 150                 155                 160

Tyr Ser Thr Ser Trp Lys Arg Thr Val Ser Gly Ser Phe Glu Val Ala
                165                 170                 175

Ala Ser Val Ser Val Asp Ile Pro Leu Val Ala Lys Ala Ser Ala Ser
            180                 185                 190
```

Thr Lys Val Val Val Gly Gly Asp Thr Thr Glu Gly Thr Glu Asn Ser
         195                 200                 205

Glu Glu Ile Thr Glu Thr Ser Ser Tyr Lys Thr Ile Val Pro Ala His
 210                 215                 220

Ser Lys Lys Thr Ile Ser Val Leu Thr Lys Leu Lys Gly Ser Ser Val
225                 230                 235                 240

Glu Tyr Phe Val Pro Met Lys Leu Lys Gly Arg Leu Gln Ala Asn Phe
                245                 250                 255

Pro Ser Pro Val Asp Gly His Tyr Tyr Trp Ala Phe Pro Ile Glu Ser
                260                 265                 270

Phe Pro Asp Phe Leu Ser Asn Ile His Gly Glu Ser Gly Ile Val Lys
            275                 280                 285

Ser Val Ser Asn Val Ser Val Thr Val Met Glu Ser Pro Ala Gln Arg
    290                 295                 300

Ile
305

<210> SEQ ID NO 17
<211> LENGTH: 990
<212> TYPE: DNA
<213> ORGANISM: Chryseobacterium sp.

<400> SEQUENCE: 17
atgatcaaaa aaatcaattc tatttgtatt ctcttactga tgttttcggt atcatgttca      60
agagatgaag tgagtactat gaatgatgat tcagaaaagg taaattattc tgaagtaaag     120
aaatcacaat tgactgaggc agagatgctt caacaaggct ggaaaattgt agatgagttt     180
aaattgccag gtagcaatag tttgggtgcg aactctactt cgcctgatga agaacgcgaa     240
atccctttca aggcaaatca cctgaaagat atgggatatg atgtaagtta ttcgggagaa     300
agaacaaggt tgaaaaacgt tttcgcttac tctggccaga ttccggatgg aattatattt     360
aatccagacc tttctgtaga tggagatgca cggaatatcg ctccaaaccc aaatgtttcc     420
attgttttgg gaactcctga ggtaactata aaaacagacg gtgcagatct accggacaat     480
gcctatacta cggaggcaat taacaatgga gacagagaaa gtgaaattac agtaacctat     540
tcttataaaa agggatattc tacgtcctgg aaacgtactg tatcgggctc atttgaagtg     600
gcagcttcag tatccgttga tattccactg gttgcaaaag cttcagcaag cacaaaagtt     660
gtggtgggag gagatacaac ggaaggtacg gaaaattctg aagaaattac cgaaaccagc     720
agctacaaga ccattgtgcc cgctcattct aaaaaaacaa tttctgtcct tacaaaattg     780
aagggatcat ccgttgaata ctttgtaccg atgaaattaa aggaagatt acaggcgaac      840 tttccttctc ccgtagatgg ccattattat tgggcttttc ctatcgaaag ctttccagat     900
tttcttacca atatacatgg agagtcagga atcgtaaaat ctgtcagcaa tgtaagtgtt     960
acggtaatgg aatcacctgc gcaaggatt                                       990

<210> SEQ ID NO 18
<211> LENGTH: 330
<212> TYPE: PRT
<213> ORGANISM: Chryseobacterium sp.

<400> SEQUENCE: 18

Met Ile Lys Lys Ile Asn Ser Ile Cys Ile Leu Leu Leu Met Phe Ser
1               5                   10                  15

Val Ser Cys Ser Arg Asp Glu Val Ser Thr Met Asn Asp Asp Ser Glu
            20                  25                  30

```
Lys Val Asn Tyr Ser Glu Val Lys Lys Ser Gln Leu Thr Glu Ala Glu
            35                  40                  45

Met Leu Gln Gln Gly Trp Lys Ile Val Asp Glu Phe Lys Leu Pro Gly
 50                  55                  60

Ser Asn Ser Leu Gly Ala Asn Ser Thr Ser Pro Asp Glu Glu Arg Glu
 65                  70                  75                  80

Ile Pro Phe Lys Ala Asn His Leu Lys Asp Met Gly Tyr Asp Val Ser
                 85                  90                  95

Tyr Ser Gly Glu Arg Thr Arg Leu Lys Asn Val Phe Ala Tyr Ser Gly
                100                 105                 110

Gln Ile Pro Asp Gly Ile Ile Phe Asn Pro Asp Leu Ser Val Asp Gly
                115                 120                 125

Asp Ala Arg Asn Ile Ala Pro Asn Pro Asn Val Ser Ile Val Leu Gly
130                 135                 140

Thr Pro Glu Val Thr Ile Lys Thr Asp Gly Ala Asp Leu Pro Asp Asn
145                 150                 155                 160

Ala Tyr Thr Thr Glu Ala Ile Asn Asn Gly Asp Arg Glu Ser Glu Ile
                165                 170                 175

Thr Val Thr Tyr Ser Tyr Lys Lys Gly Tyr Ser Thr Ser Trp Lys Arg
                180                 185                 190

Thr Val Ser Gly Ser Phe Glu Val Ala Ala Ser Val Ser Val Asp Ile
                195                 200                 205

Pro Leu Val Ala Lys Ala Ser Ala Ser Thr Lys Val Val Gly Gly
210                 215                 220

Asp Thr Thr Glu Gly Thr Glu Asn Ser Glu Glu Ile Thr Glu Thr Ser
225                 230                 235                 240

Ser Tyr Lys Thr Ile Val Pro Ala His Ser Lys Lys Thr Ile Ser Val
                245                 250                 255

Leu Thr Lys Leu Lys Gly Ser Ser Val Glu Tyr Phe Val Pro Met Lys
                260                 265                 270

Leu Lys Gly Arg Leu Gln Ala Asn Phe Pro Ser Pro Val Asp Gly His
                275                 280                 285

Tyr Tyr Trp Ala Phe Pro Ile Glu Ser Phe Pro Asp Phe Leu Thr Asn
                290                 295                 300

Ile His Gly Glu Ser Gly Ile Val Lys Ser Val Ser Asn Val Ser Val
305                 310                 315                 320

Thr Val Met Glu Ser Pro Ala Gln Arg Ile
                325                 330

<210> SEQ ID NO 19
<211> LENGTH: 930
<212> TYPE: DNA
<213> ORGANISM: Artificial Sequence
<220> FEATURE:
<223> OTHER INFORMATION: Synthetic polynucleotide

<400> SEQUENCE: 19
atggatgaag tgagtactat gaatgatgat tcagaaaagg taaattattc tgaagtaaag      60
aaatcacaat tgactgaggc agagatgctt caacaaggct ggaaaattgt agatgagttt     120
aaattgccag gtagcaatag tttgggtgcg aactctactt cgcctgatga agaacgcgaa     180
atccctttca aggcaaatca cctgaaagat atgggatatg atgtaagtta ttcgggagaa     240
agaacaaggt tgaaaaacgt tttcgcttac tctggccaga ttccggatgg aattatattt     300
aatccagacc tttctgtaga tggagatgca cggaatatcg ctccaaaccc aaatgttccc     360
```

```
attgttttgg gaactcctga ggtaactata aaaacagacg gtgcagatct accggacaat    420
gcctatacta cggaggcaat taacaatgga gacagagaaa gtgaaattac agtaacctat    480
tcttataaaa agggatattc tacgtcctgg aaacgtactg tatcgggctc atttgaagtg    540
gcagcttcag tatccgttga tattccactg gttgcaaaag cttcagcaag cacaaaagtt    600
gtggtgggag gagatacaac ggaaggtacg gaaaattctg aagaaattac cgaaaccagc    660
agctacaaga ccattgtgcc cgctcattct aaaaaaacaa tttctgtcct acaaaattg    720 aagggatcat ccgttgaata ctttgtaccg atgaaattaa aggaagatt acaggcgaac    780 tttccttctc ccgtagatgg ccattattat tgggcttttc ctatcgaaag ctttccagat    840
tttcttacca atatacatgg agagtcagga atcgtaaaat ctgtcagcaa tgtaagtgtt    900
acggtaatgg aatcacctgc gcaaaggatt                                    930
```

<210> SEQ ID NO 20
<211> LENGTH: 310
<212> TYPE: PRT
<213> ORGANISM: Artificial Sequence
<220> FEATURE:
<223> OTHER INFORMATION: Synthetic polypeptide

<400> SEQUENCE: 20

```
Met Asp Glu Val Ser Thr Met Asn Asp Asp Ser Glu Lys Val Asn Tyr
1               5                   10                  15

Ser Glu Val Lys Lys Ser Gln Leu Thr Glu Ala Glu Met Leu Gln Gln
            20                  25                  30

Gly Trp Lys Ile Val Asp Glu Phe Lys Leu Pro Gly Ser Asn Ser Leu
        35                  40                  45

Gly Ala Asn Ser Thr Ser Pro Asp Glu Glu Arg Glu Ile Pro Phe Lys
    50                  55                  60

Ala Asn His Leu Lys Asp Met Gly Tyr Asp Val Ser Tyr Ser Gly Glu
65                  70                  75                  80

Arg Thr Arg Leu Lys Asn Val Phe Ala Tyr Ser Gly Gln Ile Pro Asp
                85                  90                  95

Gly Ile Ile Phe Asn Pro Asp Leu Ser Val Asp Gly Asp Ala Arg Asn
            100                 105                 110

Ile Ala Pro Asn Pro Asn Val Ser Ile Val Leu Gly Thr Pro Glu Val
        115                 120                 125

Thr Ile Lys Thr Asp Gly Ala Asp Leu Pro Asp Asn Ala Tyr Thr Thr
    130                 135                 140

Glu Ala Ile Asn Asn Gly Asp Arg Glu Ser Glu Ile Thr Val Thr Tyr
145                 150                 155                 160

Ser Tyr Lys Lys Gly Tyr Ser Thr Ser Trp Lys Arg Thr Val Ser Gly
                165                 170                 175

Ser Phe Glu Val Ala Ala Ser Val Ser Val Asp Ile Pro Leu Val Ala
            180                 185                 190

Lys Ala Ser Ala Ser Thr Lys Val Val Val Gly Gly Asp Thr Thr Glu
        195                 200                 205

Gly Thr Glu Asn Ser Glu Glu Ile Thr Glu Thr Ser Ser Tyr Lys Thr
    210                 215                 220

Ile Val Pro Ala His Ser Lys Lys Thr Ile Ser Val Leu Thr Lys Leu
225                 230                 235                 240

Lys Gly Ser Ser Val Glu Tyr Phe Val Pro Met Lys Leu Lys Gly Arg
                245                 250                 255
```

Leu Gln Ala Asn Phe Pro Ser Pro Val Asp Gly His Tyr Tyr Trp Ala
                260                 265                 270

Phe Pro Ile Glu Ser Phe Pro Asp Phe Leu Thr Asn Ile His Gly Glu
            275                 280                 285

Ser Gly Ile Val Lys Ser Val Ser Asn Val Ser Val Thr Val Met Glu
        290                 295                 300

Ser Pro Ala Gln Arg Ile
305                 310

<210> SEQ ID NO 21
<211> LENGTH: 990
<212> TYPE: DNA
<213> ORGANISM: Chryseobacterium sp.

<400> SEQUENCE: 21

| | | |
|---|---|---|
| atgaataaaa aaatcaattc tgttttgatt cttttattag cattttcagt atcatgttca | 60 |
| agggatgaag tgagttctat gaatgatgat ccggaaaaaa taaattatgc tgatacaaag | 120 |
| agtgcacatt taacacaggc agagatgctt cagaaaggct ggaaagttgt agatgagttt | 180 |
| aaattgccag gcaataataa tctggggata aactatactt ctacccatga gagcgtgaa | 240 |
| attcctttca aacctaatca cctgaaagat atgggatatg atgttagttt ttccggagaa | 300 |
| agaacgagat tgaaaaatgt ttttgcctac gctggtcagg ttccggatgg aattatattt | 360 |
| aatcctgatc tttctgtaga cggagatgtc cggaatacgg ctcctaatcc taatgtttcc | 420 |
| attgttttag aacacctga ggtaaacata aaaacagacg agtagattt accggataat | 480 |
| tcctatacca cggaggccat taataatgga gatagaaaa gtgaaattac agtaacctat | 540 |
| tcctataaaa agggatattc tacttcctgg aagcgcactg tctcaggctc atttgaagtg | 600 |
| gcagcatccg tatctgttga tattccgtta gtggcaaaag cttctgccag cacaaaagtt | 660 |
| gttgtaggag gagatacaac ggaaggcaca gaaacctctg aagaaattac cgagaccagc | 720 |
| agctataaga ctatcgtgcc ggctcactct aaaaaaagta tttctattct gacgaaatta | 780 |
| aaagggtctt ctgttgaata ctttgtacct atgaaattga ccggaagatt acaggctaac | 840 |
| ttccttctc cggtagatgg gcattattat tgggcttttc ctattgaaaa cttccctgat | 900 |
| tttctttcca atatacacgg agagtcgggg attgtaaaat ctgtaagcaa tgtaagtgtt | 960 |
| actgttatgg aatcacctgc gcagaagata | 990 |

<210> SEQ ID NO 22
<211> LENGTH: 330
<212> TYPE: PRT
<213> ORGANISM: Chryseobacterium sp.

<400> SEQUENCE: 22

Met Asn Lys Lys Ile Asn Ser Val Leu Ile Leu Leu Ala Phe Ser
1               5                   10                  15

Val Ser Cys Ser Arg Asp Glu Val Ser Ser Met Asn Asp Asp Pro Glu
                20                  25                  30

Lys Ile Asn Tyr Ala Asp Thr Lys Ser Ala His Leu Thr Gln Ala Glu
            35                  40                  45

Met Leu Gln Lys Gly Trp Lys Val Val Asp Glu Phe Lys Leu Pro Gly
        50                  55                  60

Asn Asn Asn Leu Gly Ile Asn Tyr Thr Ser Thr His Glu Glu Arg Glu
65                  70                  75                  80

Ile Pro Phe Lys Pro Asn His Leu Lys Asp Met Gly Tyr Asp Val Ser
                85                  90                  95

```
Phe Ser Gly Glu Arg Thr Arg Leu Lys Asn Val Phe Ala Tyr Ala Gly
            100                 105                 110

Gln Val Pro Asp Gly Ile Ile Phe Asn Pro Asp Leu Ser Val Asp Gly
        115                 120                 125

Asp Val Arg Asn Thr Ala Pro Asn Pro Asn Val Ser Ile Val Leu Gly
130                 135                 140

Thr Pro Glu Val Asn Ile Lys Thr Asp Gly Val Asp Leu Pro Asp Asn
145                 150                 155                 160

Ser Tyr Thr Thr Glu Ala Ile Asn Asn Gly Asp Arg Glu Ser Glu Ile
                165                 170                 175

Thr Val Thr Tyr Ser Tyr Lys Lys Gly Tyr Ser Thr Ser Trp Lys Arg
            180                 185                 190

Thr Val Ser Gly Ser Phe Glu Val Ala Ala Ser Val Ser Val Asp Ile
        195                 200                 205

Pro Leu Val Ala Lys Ala Ser Ala Ser Thr Lys Val Val Val Gly Gly
    210                 215                 220

Asp Thr Thr Glu Gly Thr Glu Thr Ser Glu Glu Ile Thr Glu Thr Ser
225                 230                 235                 240

Ser Tyr Lys Thr Ile Val Pro Ala His Ser Lys Lys Ser Ile Ser Ile
                245                 250                 255

Leu Thr Lys Leu Lys Gly Ser Ser Val Glu Tyr Phe Val Pro Met Lys
            260                 265                 270

Leu Thr Gly Arg Leu Gln Ala Asn Phe Pro Ser Pro Val Asp Gly His
        275                 280                 285

Tyr Tyr Trp Ala Phe Pro Ile Glu Asn Phe Pro Asp Phe Leu Ser Asn
    290                 295                 300

Ile His Gly Glu Ser Gly Ile Val Lys Ser Val Ser Asn Val Ser Val
305                 310                 315                 320

Thr Val Met Glu Ser Pro Ala Gln Lys Ile
                325                 330

<210> SEQ ID NO 23
<211> LENGTH: 915
<212> TYPE: DNA
<213> ORGANISM: Artificial Sequence
<220> FEATURE:
<223> OTHER INFORMATION: Synthetic polynucleotide

<400> SEQUENCE: 23
atgatgaatg atgatccgga aaaaataaat tatgctgata caaagagtgc acatttaaca      60
caggcagaga tgcttcagaa aggctggaaa gttgtagatg agtttaaatt gccaggcaat     120
aataatctgg ggataaacta tacttctacc catgaagagc gtgaaattcc tttcaaacct     180
aatcacctga agatatgggg atatgatgtt agttttttccg gagaaagaac gagattgaaa     240
aatgttttgg cctacgctgg tcaggttccg gatggaatta tatttaatcc tgatctttct     300
gtagacggag atgtccggaa tacggctcct aatcctaatg tttccattgt tttaggaaca     360
cctgaggtaa acataaaaac agacggagta gatttaccgg ataattccta taccacggag     420
gccattaata tggagatag agaaagtgaa attacagtaa cctattccta taaaaaggga     480
tattctactt cctggaagcg cactgtctca ggctcatttg aagtggcagc atccgtatct     540
gttgatattc cgttagtggc aaaagcttct gccagcacaa agttgttgt aggaggagat     600 acaacggaag gcacagaaac ctctgaagaa attaccgaga ccagcagcta taagactatc     660
gtgccggctc actctaaaaa aagtatttct attctgacga aattaaaagg gtcttctgtt     720
```

```
gaatactttg tacctatgaa attgaccgga agattacagg ctaactttcc ttctccggta    780
gatgggcatt attattgggc ttttcctatt gaaaacttcc ctgattttct ttccaatata    840
cacggagagt cggggattgt aaaatctgta agcaatgtaa gtgttactgt tatggaatca    900
cctgcgcaga agata                                                    915
```

<210> SEQ ID NO 24
<211> LENGTH: 305
<212> TYPE: PRT
<213> ORGANISM: Artificial Sequence
<220> FEATURE:
<223> OTHER INFORMATION: Synthetic polypeptide

<400> SEQUENCE: 24

```
Met Met Asn Asp Asp Pro Glu Lys Ile Asn Tyr Ala Asp Thr Lys Ser
1               5                   10                  15

Ala His Leu Thr Gln Ala Glu Met Leu Gln Lys Gly Trp Lys Val Val
                20                  25                  30

Asp Glu Phe Lys Leu Pro Gly Asn Asn Asn Leu Gly Ile Asn Tyr Thr
            35                  40                  45

Ser Thr His Glu Glu Arg Glu Ile Pro Phe Lys Pro Asn His Leu Lys
        50                  55                  60

Asp Met Gly Tyr Asp Val Ser Phe Ser Gly Glu Arg Thr Arg Leu Lys
65                  70                  75                  80

Asn Val Phe Ala Tyr Ala Gly Gln Val Pro Asp Gly Ile Ile Phe Asn
                85                  90                  95

Pro Asp Leu Ser Val Asp Gly Asp Val Arg Asn Thr Ala Pro Asn Pro
            100                 105                 110

Asn Val Ser Ile Val Leu Gly Thr Pro Glu Val Asn Ile Lys Thr Asp
        115                 120                 125

Gly Val Asp Leu Pro Asp Asn Ser Tyr Thr Thr Glu Ala Ile Asn Asn
    130                 135                 140

Gly Asp Arg Glu Ser Glu Ile Thr Val Thr Tyr Ser Tyr Lys Lys Gly
145                 150                 155                 160

Tyr Ser Thr Ser Trp Lys Arg Thr Val Ser Gly Ser Phe Glu Val Ala
                165                 170                 175

Ala Ser Val Ser Val Asp Ile Pro Leu Val Ala Lys Ala Ser Ala Ser
            180                 185                 190

Thr Lys Val Val Val Gly Gly Asp Thr Thr Glu Gly Thr Glu Thr Ser
        195                 200                 205

Glu Glu Ile Thr Glu Thr Ser Ser Tyr Lys Thr Ile Val Pro Ala His
    210                 215                 220

Ser Lys Lys Ser Ile Ser Ile Leu Thr Lys Leu Lys Gly Ser Ser Val
225                 230                 235                 240

Glu Tyr Phe Val Pro Met Lys Leu Thr Gly Arg Leu Gln Ala Asn Phe
                245                 250                 255

Pro Ser Pro Val Asp Gly His Tyr Tyr Trp Ala Phe Pro Ile Glu Asn
            260                 265                 270

Phe Pro Asp Phe Leu Ser Asn Ile His Gly Glu Ser Gly Ile Val Lys
        275                 280                 285

Ser Val Ser Asn Val Ser Val Thr Val Met Glu Ser Pro Ala Gln Lys
    290                 295                 300

Ile
305
```

<210> SEQ ID NO 25
<211> LENGTH: 1215
<212> TYPE: DNA
<213> ORGANISM: Bacillus sp.

<400> SEQUENCE: 25

| | | | | | |
|---|---|---|---|---|---|
| gtgaagaaaa | tgtatacaaa | tcataaaatg | aagtgttgga | agaaaaaatt | agctaaagtt | 60 |
| gcaccaattt | gtgtgttaag | tacaggattt | ttagtgggcg | tagctaatcc | tgcttttgct | 120 |
| gctagtaaga | ctctcaaaac | tgttcacact | caagcgaaac | agtctaatttt | attgactacg | 180 |
| tctaatagta | acttagttca | tatcggtgat | gatttaaatc | aaagaatcta | tgatgctgtg | 240 |
| aaaaataagc | ctgatttatt | tgtatataga | caccttaaag | atggaactgg | tagagatgaa | 300 |
| cgaattagtg | atatggatca | aagtctacaa | aatggttaca | ttgttgtaat | gaatagctta | 360 |
| gcatacggaa | aagttacgat | taacaatgga | tatacgattg | attggaatca | aaaagaatat | 420 |
| gtcggtggag | atatcaaggt | aacgggtaaa | caagatacag | tagatggatt | gcatagtttt | 480 |
| acattaggaa | cttttcataa | tgaagaggat | attgaacaaa | ctgctactac | acaaaaagaa | 540 |
| acttatcaaa | cgacagatag | ttttacctat | tcaaatagtg | agggtgttaa | gttaggttta | 600 |
| acagaatcta | taaaagcaac | tgcgggcgta | ccttttgttg | tagaaggcga | agagacaaca | 660 |
| acactttcaa | gtgaattctc | atataatcat | acctcttcaa | atacctcgac | gaattcacac | 720 |
| acaattgaat | ttccatcgca | gactattaaa | gtcaaaccgc | atggaactac | aatttatacg | 780 |
| ggtgaggtaa | aacaaatgaa | ttttttctgga | gattactctg | ggacagcgaa | attatcaaca | 840 |
| aatgatattt | catttgctat | aacggattcg | ggaagtcatt | ggggagatgt | tatcgctgcg | 900 |
| ccgggtgaag | agggtcattt | tttatataat | atattcaaat | actccggtca | cataattcct | 960 |
| tcagatattc | gtttagatga | tgaaaataga | acggttgttg | ttgataattc | atctatttat | 1020 |
| tttacaggaa | aactagggtt | taacatggag | gcaacatgga | aattcatccc | tgatgatcct | 1080 |
| aaaaaaccaa | gtgttacaat | accaaatgat | gtatatttaa | aagaacaagc | ttctgggaat | 1140 |
| attagcaagt | acattgacca | attaatacaa | actaaaatgg | gttctagtgc | aaagaaagga | 1200 |
| tacagtccca | agaaa | | | | | 1215 |

<210> SEQ ID NO 26
<211> LENGTH: 405
<212> TYPE: PRT
<213> ORGANISM: Bacillus sp.

<400> SEQUENCE: 26

Val Lys Lys Met Tyr Thr Asn His Lys Met Lys Cys Trp Lys Lys Lys
1               5                   10                  15

Leu Ala Lys Val Ala Pro Ile Cys Val Leu Ser Thr Gly Phe Leu Val
            20                  25                  30

Gly Val Ala Asn Pro Ala Phe Ala Ala Ser Lys Thr Leu Lys Thr Val
        35                  40                  45

His Thr Gln Ala Lys Gln Ser Asn Leu Leu Thr Thr Ser Asn Ser Asn
    50                  55                  60

Leu Val His Ile Gly Asp Asp Leu Asn Gln Arg Ile Tyr Asp Ala Val
65                  70                  75                  80

Lys Asn Lys Pro Asp Leu Phe Val Tyr Arg His Leu Lys Asp Gly Thr
                85                  90                  95

Gly Arg Asp Glu Arg Ile Ser Asp Met Asp Gln Ser Leu Gln Asn Gly
            100                 105                 110

```
Tyr Ile Val Val Met Asn Ser Leu Ala Tyr Gly Lys Val Thr Ile Asn
            115                 120                 125

Asn Gly Tyr Thr Ile Asp Trp Asn Gln Lys Glu Tyr Val Gly Gly Asp
        130                 135                 140

Ile Lys Val Thr Gly Lys Gln Asp Thr Val Asp Gly Leu His Ser Phe
145                 150                 155                 160

Thr Leu Gly Thr Phe His Asn Glu Glu Asp Ile Glu Gln Thr Ala Thr
                165                 170                 175

Thr Gln Lys Glu Thr Tyr Gln Thr Thr Asp Ser Phe Thr Tyr Ser Asn
            180                 185                 190

Ser Glu Gly Val Lys Leu Gly Leu Thr Glu Ser Ile Lys Ala Thr Ala
        195                 200                 205

Gly Val Pro Phe Val Val Glu Gly Glu Thr Thr Thr Leu Ser Ser
    210                 215                 220

Glu Phe Ser Tyr Asn His Thr Ser Ser Asn Thr Ser Thr Asn Ser His
225                 230                 235                 240

Thr Ile Glu Phe Pro Ser Gln Thr Ile Lys Val Lys Pro His Gly Thr
                245                 250                 255

Thr Ile Tyr Thr Gly Glu Val Lys Gln Met Asn Phe Ser Gly Asp Tyr
            260                 265                 270

Ser Gly Thr Ala Lys Leu Ser Thr Asn Asp Ile Ser Phe Ala Ile Thr
        275                 280                 285

Asp Ser Gly Ser His Trp Gly Asp Val Ile Ala Ala Pro Gly Glu Glu
    290                 295                 300

Gly His Phe Leu Tyr Asn Ile Phe Lys Tyr Ser Gly His Ile Ile Pro
305                 310                 315                 320

Ser Asp Ile Arg Leu Asp Asp Glu Asn Arg Thr Val Val Asp Asn
                325                 330                 335

Ser Ser Ile Tyr Phe Thr Gly Lys Leu Gly Phe Asn Met Glu Ala Thr
            340                 345                 350

Trp Lys Phe Ile Pro Asp Asp Pro Lys Lys Pro Ser Val Thr Ile Pro
        355                 360                 365

Asn Asp Val Tyr Leu Lys Glu Gln Ala Ser Gly Asn Ile Ser Lys Tyr
370                 375                 380

Ile Asp Gln Leu Ile Gln Thr Lys Met Gly Ser Ser Ala Lys Lys Gly
385                 390                 395                 400

Tyr Ser Pro Lys Lys
            405

<210> SEQ ID NO 27
<211> LENGTH: 1098
<212> TYPE: DNA
<213> ORGANISM: Artificial Sequence
<220> FEATURE:
<223> OTHER INFORMATION: Synthetic polynucleotide

<400> SEQUENCE: 27
atggctagta agactctcaa aactgttcac actcaagcga acagtctaa tttattgact      60 acgtctaata gtaacttagt tcatatcggt gatgatttaa atcaaagaat ctatgatgct    120
gtgaaaaata gcctgatttt atttgtatat agacaccta aagatggaac tggtagagat    180
gaacgaatta gtgatatgga tcaaagtcta caaaatggtt acattgttgt aatgaatagc    240
ttagcatacg gaaagttac gattaacaat ggatatacga ttgattggaa tcaaaaagaa    300
tatgtcggtg gagatatcaa ggtaacgggt aaacaagata cagtagatgg attgcatagt    360
```

```
tttacattag gaacttttca taatgaagag gatattgaac aaactgctac tacacaaaaa    420
gaaacttatc aaacgacaga tagttttacc tattcaaata gtgagggtgt taagttaggt    480
ttaacagaat ctataaaagc aactgcgggc gtaccttttg ttgtagaagg cgaagagaca    540
acaacacttt caagtgaatt ctcatataat catacctctt caaataccte gacgaattca    600 cacacaattg aatttccatc gcagactatt aaagtcaaac cgcatggaac tacaatttat    660
acgggtgagg taaacaaat gaattttct ggagattact ctgggacagc gaaattatca     720
acaaatgata tttcatttgc tataacggat tcgggaagtc attggggaga tgttatcgct    780
gcgccgggtg aagagggtca ttttttatat aatatattca aatactccgg tcacataatt    840
ccttcagata ttcgtttaga tgatgaaaat agaacggttg ttgttgataa ttcatctatt    900
tattttacag gaaactagg gtttaacatg gaggcaacat ggaaattcat ccctgatgat     960
cctaaaaaac caagtgttac aataccaaat gatgtatatt taaaagaaca agcttctggg   1020
aatattagca agtacattga ccaattaata caaactaaaa tgggttctag tgcaagaaa    1080 ggatacagtc ccaagaaa                                                  1098
```

<210> SEQ ID NO 28
<211> LENGTH: 366
<212> TYPE: PRT
<213> ORGANISM: Artificial Sequence
<220> FEATURE:
<223> OTHER INFORMATION: Synthetic polypeptide

<400> SEQUENCE: 28

```
Met Ala Ser Lys Thr Leu Lys Thr Val His Thr Gln Ala Lys Gln Ser
1               5                   10                  15

Asn Leu Leu Thr Thr Ser Asn Ser Asn Leu Val His Ile Gly Asp Asp
            20                  25                  30

Leu Asn Gln Arg Ile Tyr Asp Ala Val Lys Asn Lys Pro Asp Leu Phe
        35                  40                  45

Val Tyr Arg His Leu Lys Asp Gly Thr Gly Arg Asp Glu Arg Ile Ser
    50                  55                  60

Asp Met Asp Gln Ser Leu Gln Asn Gly Tyr Ile Val Val Met Asn Ser
65                  70                  75                  80

Leu Ala Tyr Gly Lys Val Thr Ile Asn Asn Gly Tyr Thr Ile Asp Trp
                85                  90                  95

Asn Gln Lys Glu Tyr Val Gly Gly Asp Ile Lys Val Thr Gly Lys Gln
            100                 105                 110

Asp Thr Val Asp Gly Leu His Ser Phe Thr Leu Gly Thr Phe His Asn
        115                 120                 125

Glu Glu Asp Ile Glu Gln Thr Ala Thr Thr Gln Lys Glu Thr Tyr Gln
    130                 135                 140

Thr Thr Asp Ser Phe Thr Tyr Ser Asn Ser Glu Gly Val Lys Leu Gly
145                 150                 155                 160

Leu Thr Glu Ser Ile Lys Ala Thr Ala Gly Val Pro Phe Val Val Glu
                165                 170                 175

Gly Glu Glu Thr Thr Thr Leu Ser Ser Glu Phe Ser Tyr Asn His Thr
            180                 185                 190

Ser Ser Asn Thr Ser Thr Asn Ser His Thr Ile Glu Phe Pro Ser Gln
        195                 200                 205

Thr Ile Lys Val Lys Pro His Gly Thr Thr Ile Tyr Thr Gly Glu Val
    210                 215                 220

Lys Gln Met Asn Phe Ser Gly Asp Tyr Ser Gly Thr Ala Lys Leu Ser
```

```
                 225                 230                 235                 240
Thr Asn Asp Ile Ser Phe Ala Ile Thr Asp Ser Gly Ser His Trp Gly
                245                 250                 255
Asp Val Ile Ala Ala Pro Gly Glu Glu Gly His Phe Leu Tyr Asn Ile
                260                 265                 270
Phe Lys Tyr Ser Gly His Ile Ile Pro Ser Asp Ile Arg Leu Asp Asp
                275                 280                 285
Glu Asn Arg Thr Val Val Val Asp Asn Ser Ser Ile Tyr Phe Thr Gly
                290                 295                 300
Lys Leu Gly Phe Asn Met Glu Ala Thr Trp Lys Phe Ile Pro Asp Asp
305                 310                 315                 320
Pro Lys Lys Pro Ser Val Thr Ile Pro Asn Asp Val Tyr Leu Lys Glu
                325                 330                 335
Gln Ala Ser Gly Asn Ile Ser Lys Tyr Ile Asp Gln Leu Ile Gln Thr
                340                 345                 350
Lys Met Gly Ser Ser Ala Lys Lys Gly Tyr Ser Pro Lys Lys
                355                 360                 365
```

<210> SEQ ID NO 29
<211> LENGTH: 1206
<212> TYPE: DNA
<213> ORGANISM: Artificial Sequence
<220> FEATURE:
<223> OTHER INFORMATION: Synthetic polynucleotide

<400> SEQUENCE: 29

```
atgtatacaa atcataaaat gaagtgttgg aagaaaaaat tagctaaagt tgcaccaatt      60
tgtgtgttaa gtacaggatt tttagtgggc gtagctaatc ctgcttttgc tgctagtaag     120
actctcaaaa ctgttcacac tcaagcgaaa cagtctaatt tattgactac gtctaatagt     180
aacttagttc atatcggtga tgatttaaat caaagaatct atgatgctgt gaaaaataag     240
cctgatttat ttgtatatag acaccttaaa gatggaactg gtagagatga acgaattagt     300
gatatggatc aaagtctaca aatggttac attgttgtaa tgaatagctt agcatacgga      360
aaagttacga ttaacaatgg atatacgatt gattggaatc aaaaagaata tgtcggtgga     420
gatatcaagg taacgggtaa acaagataca gtagatggat tgcatagttt tacattagga     480
acttttcata tgaagagga tattgaacaa actgctacta cacaaaaaga aacttatcaa      540
acgacagata gttttaccta ttcaaatagt gagggtgtta agttaggttt aacagaatct     600
ataaaagcaa ctgcgggcgt accttttgtt gtagaaggcg aagagacaac aacactttca     660
agtgaattct catataatca tacctcttca aatacctcga cgaattcaca cacaattgaa     720
tttccatcgc agactattaa agtcaaaccg catggaacta caattttatac gggtgaggta     780
aaacaaatga attttctgg agattactct gggacagcga attatcaac aaatgatatt       840
tcatttgcta taacggattc gggaagtcat tggggagatg ttatcgctgc gccgggtgaa     900
gagggtcatt ttttatataa tatattcaaa tactccggtc acataattcc ttcagatatt     960
cgtttagatg atgaaaatag aacggttgtt gttgataatt catctattta ttttacagga    1020
aaactagggt ttaacatgga ggcaacatgg aaattcatcc ctgatgatcc taaaaaacca    1080
agtgttacaa taccaaatga tgtatattta aagaacaag cttctgggaa tattagcaag     1140
tacattgacc aattaataca aactaaaatg ggttctagtg caaagaaagg atacagtccc    1200
aagaaa                                                                1206
```

```
<210> SEQ ID NO 30
<211> LENGTH: 402
<212> TYPE: PRT
<213> ORGANISM: Artificial Sequence
<220> FEATURE:
<223> OTHER INFORMATION: Synthetic polypeptide

<400> SEQUENCE: 30

Met Tyr Thr Asn His Lys Met Lys Cys Trp Lys Lys Leu Ala Lys
1               5                   10                  15

Val Ala Pro Ile Cys Val Leu Ser Thr Gly Phe Leu Val Gly Val Ala
                20                  25                  30

Asn Pro Ala Phe Ala Ala Ser Lys Thr Leu Lys Thr Val His Thr Gln
            35                  40                  45

Ala Lys Gln Ser Asn Leu Leu Thr Thr Ser Asn Ser Asn Leu Val His
    50                  55                  60

Ile Gly Asp Asp Leu Asn Gln Arg Ile Tyr Asp Ala Val Lys Asn Lys
65                  70                  75                  80

Pro Asp Leu Phe Val Tyr Arg His Leu Lys Asp Gly Thr Gly Arg Asp
                85                  90                  95

Glu Arg Ile Ser Asp Met Asp Gln Ser Leu Gln Asn Gly Tyr Ile Val
            100                 105                 110

Val Met Asn Ser Leu Ala Tyr Gly Lys Val Thr Ile Asn Asn Gly Tyr
    115                 120                 125

Thr Ile Asp Trp Asn Gln Lys Glu Tyr Val Gly Gly Asp Ile Lys Val
130                 135                 140

Thr Gly Lys Gln Asp Thr Val Asp Gly Leu His Ser Phe Thr Leu Gly
145                 150                 155                 160

Thr Phe His Asn Glu Glu Asp Ile Glu Gln Thr Ala Thr Thr Gln Lys
                165                 170                 175

Glu Thr Tyr Gln Thr Thr Asp Ser Phe Thr Tyr Ser Asn Ser Glu Gly
            180                 185                 190

Val Lys Leu Gly Leu Thr Glu Ser Ile Lys Ala Thr Ala Gly Val Pro
    195                 200                 205

Phe Val Val Glu Gly Glu Glu Thr Thr Thr Leu Ser Ser Glu Phe Ser
210                 215                 220

Tyr Asn His Thr Ser Ser Asn Thr Ser Thr Asn Ser His Thr Ile Glu
225                 230                 235                 240

Phe Pro Ser Gln Thr Ile Lys Val Lys Pro His Gly Thr Thr Ile Tyr
                245                 250                 255

Thr Gly Glu Val Lys Gln Met Asn Phe Ser Gly Asp Tyr Ser Gly Thr
            260                 265                 270

Ala Lys Leu Ser Thr Asn Asp Ile Ser Phe Ala Ile Thr Asp Ser Gly
    275                 280                 285

Ser His Trp Gly Asp Val Ile Ala Ala Pro Gly Glu Glu Gly His Phe
290                 295                 300

Leu Tyr Asn Ile Phe Lys Tyr Ser Gly His Ile Ile Pro Ser Asp Ile
305                 310                 315                 320

Arg Leu Asp Asp Glu Asn Arg Thr Val Val Val Asp Asn Ser Ser Ile
                325                 330                 335

Tyr Phe Thr Gly Lys Leu Gly Phe Asn Met Glu Ala Thr Trp Lys Phe
            340                 345                 350

Ile Pro Asp Asp Pro Lys Lys Pro Ser Val Thr Ile Pro Asn Asp Val
    355                 360                 365

Tyr Leu Lys Glu Gln Ala Ser Gly Asn Ile Ser Lys Tyr Ile Asp Gln
```

```
                 370                 375                 380
Leu Ile Gln Thr Lys Met Gly Ser Ser Ala Lys Lys Gly Tyr Ser Pro
385                 390                 395                 400

Lys Lys

<210> SEQ ID NO 31
<211> LENGTH: 1206
<212> TYPE: DNA
<213> ORGANISM: Bacillus sp.

<400> SEQUENCE: 31
gtgagaaaaa tgaatgaaaa taataaaatg aagtgctgga agaaaaaagt agctaaaatt      60
gtaccgattt ctgtgttaag tacaggattt ttagtggggg gaggaaatcc agcttttgca     120
gctagtaagg aatcaaagat gcccccaaa accgttcacg ctcaagcgaa acaatctaat     180
ttatcgacta agtctaatag taacttatat cttatcggag attatttaaa tcaaagaatc     240
tatgatgctg taaaaaatag accagattta tttgtttaca aacacattgg agatcaatct     300
ggtagaactg aacggattag tgacatggat caaagtctac aaaatggtta tatcgaagta     360
atgaatgcct aaaataccc aggagttacg attaacaatg gaataatat agattggaat      420 caaagagaat atgttggtgg agatatcaag gtaacaggta acaagataa agtagatgga      480 ttgcatagtt tcacattagg aacttttcat aatacagggg atattgaaca aactgctact     540
acgcaaaaag aaacttatca aacgacagat agttttacct attcaaatag tgagggtgtt     600
aagttaggat aacagaatc tataaaagca actgcgggcg tacctttgt tatagaaggc      660 gaagagacaa caacaatttc aagtgaattt tcatataatc atacctcttc aaatacctcg     720
acgaattcac acacaattga atttccatca caaactatta agtcaaacc ccatggaact      780 acaatttaca ctggagaggt aaaacaaatg aatttttccg gagattactc tggtacagct     840
aaattaacaa caaggatgt ttcttttgct gcagtagata cttacgggca tattggagat      900
gttattgcag caccgggaga ggaagaacat ttttatata atattttaa atattcaggc      960 caatcaatcc cttcggatat tcgtttagat gatgaaaata aatggttgt tgttgataat     1020 tcatccattc atttacagg gaaattaggt tttaacatgg aagccacatg gaaattcatc     1080
cctgatgatc ctaaaaaacc aagtgttaca ataccaaatg atgtatattt aaaagaacag     1140
gcttctggga acattagcaa gtacattgac ggattaatac aaactaaaat gaaatctatg     1200
catcaa                                                              1206

<210> SEQ ID NO 32
<211> LENGTH: 402
<212> TYPE: PRT
<213> ORGANISM: Bacillus sp.

<400> SEQUENCE: 32

Val Arg Lys Met Asn Glu Asn Asn Lys Met Lys Cys Trp Lys Lys Lys
1               5                  10                  15

Val Ala Lys Ile Val Pro Ile Ser Val Leu Ser Thr Gly Phe Leu Val
               20                  25                  30

Gly Gly Gly Asn Pro Ala Phe Ala Ala Ser Lys Glu Ser Lys Met Pro
           35                  40                  45

Pro Lys Thr Val His Ala Gln Ala Lys Gln Ser Asn Leu Ser Thr Lys
       50                  55                  60

Ser Asn Ser Asn Leu Tyr Leu Ile Gly Asp Tyr Leu Asn Gln Arg Ile
65                  70                  75                  80
```

Tyr Asp Ala Val Lys Asn Arg Pro Asp Leu Phe Val Tyr Lys His Ile
                 85                  90                  95
Gly Asp Gln Ser Gly Arg Thr Glu Arg Ile Ser Asp Met Asp Gln Ser
            100                 105                 110
Leu Gln Asn Gly Tyr Ile Glu Val Met Asn Ala Leu Lys Tyr Pro Gly
        115                 120                 125
Val Thr Ile Asn Asn Gly Asn Asn Ile Asp Trp Asn Gln Arg Glu Tyr
    130                 135                 140
Val Gly Gly Asp Ile Lys Val Thr Gly Lys Gln Asp Lys Val Asp Gly
145                 150                 155                 160
Leu His Ser Phe Thr Leu Gly Thr Phe His Asn Thr Gly Asp Ile Glu
                165                 170                 175
Gln Thr Ala Thr Thr Gln Lys Glu Thr Tyr Gln Thr Thr Asp Ser Phe
            180                 185                 190
Thr Tyr Ser Asn Ser Glu Gly Val Lys Leu Gly Leu Thr Glu Ser Ile
        195                 200                 205
Lys Ala Thr Ala Gly Val Pro Phe Val Ile Glu Gly Glu Thr Thr
    210                 215                 220
Thr Ile Ser Ser Glu Phe Ser Tyr Asn His Thr Ser Ser Asn Thr Ser
225                 230                 235                 240
Thr Asn Ser His Thr Ile Glu Phe Pro Ser Gln Thr Ile Lys Val Lys
                245                 250                 255
Pro His Gly Thr Thr Ile Tyr Thr Gly Glu Val Lys Gln Met Asn Phe
            260                 265                 270
Ser Gly Asp Tyr Ser Gly Thr Ala Lys Leu Thr Thr Lys Asp Val Ser
        275                 280                 285
Phe Ala Ala Val Asp Thr Tyr Gly His Ile Gly Asp Val Ile Ala Ala
    290                 295                 300
Pro Gly Glu Glu Glu His Phe Leu Tyr Asn Ile Phe Lys Tyr Ser Gly
305                 310                 315                 320
Gln Ser Ile Pro Ser Asp Ile Arg Leu Asp Asp Glu Asn Arg Met Val
                325                 330                 335
Val Val Asp Asn Ser Ser Ile His Phe Thr Gly Lys Leu Gly Phe Asn
            340                 345                 350
Met Glu Ala Thr Trp Lys Phe Ile Pro Asp Asp Pro Lys Lys Pro Ser
        355                 360                 365
Val Thr Ile Pro Asn Asp Val Tyr Leu Lys Glu Gln Ala Ser Gly Asn
    370                 375                 380
Ile Ser Lys Tyr Ile Asp Gly Leu Ile Gln Thr Lys Met Lys Ser Met
385                 390                 395                 400
His Gln

<210> SEQ ID NO 33
<211> LENGTH: 1197
<212> TYPE: DNA
<213> ORGANISM: Artificial Sequence
<220> FEATURE:
<223> OTHER INFORMATION: Synthetic polynucleotide

<400> SEQUENCE: 33
atgaatgaaa ataataaaat gaagtgctgg aagaaaaaag tagctaaaat tgtaccgatt      60
tctgtgttaa gtacaggatt tttagtgggg ggaggaaatc cagcttttgc agctagtaag     120
gaatcaaaga tgcccccccaa aaccgttcac gctcaagcga acaatctaa tttatcgact     180

```
aagtctaata gtaacttata tcttatcgga gattatttaa atcaaagaat ctatgatgct      240
gtaaaaaata gaccagattt atttgtttac aaacacattg gagatcaatc tggtagaact      300
gaacggatta gtgacatgga tcaaagtcta caaaatggtt atatcgaagt aatgaatgcc      360
ttaaaatacc caggagttac gattaacaat ggaataata tagattggaa tcaaagagaa       420
tatgttggtg gagatatcaa ggtaacaggt aaacaagata aagtagatgg attgcatagt      480
ttcacattag gaacttttca taatacaggg gatattgaac aaactgctac tacgcaaaaa      540
gaaacttatc aaacgacaga tagttttacc tattcaaata gtgagggtgt aagttagga       600 ttaacagaat ctataaaagc aactgcgggc gtacctttg ttatagaagg cgaagagaca       660
acaacaattt caagtgaatt ttcatataat catacctctt caaataccte gacgaattca      720 cacacaattg aatttccatc acaaactatt aaagtcaaac cccatggaac tacaatttac      780
actggagagg taaacaaat gaattttttcc ggagattact ctggtacagc taaattaaca      840
acaaaggatg tttcttttgc tgcagtagat acttacgggc atattggaga tgttattgca      900
gcaccgggag aggaagaaca ttttttatat aatatttttta aatattcagg ccaatcaatc     960
ccttcggata ttcgtttaga tgatgaaaat agaatggttg ttgttgataa ttcatccatt    1020
cattttacag ggaaattagg ttttaacatg gaagccacat ggaaattcat ccctgatgat    1080
cctaaaaaac caagtgttac aataccaaat gatgtatatt taaaagaaca ggcttctggg    1140
aacattagca agtacattga cggattaata caaactaaaa tgaaatctat gcatcaa       1197
```

<210> SEQ ID NO 34
<211> LENGTH: 399
<212> TYPE: PRT
<213> ORGANISM: Artificial Sequence
<220> FEATURE:
<223> OTHER INFORMATION: Artificial polypeptide

<400> SEQUENCE: 34

```
Met Asn Glu Asn Asn Lys Met Lys Cys Trp Lys Lys Lys Val Ala Lys
1               5                   10                  15

Ile Val Pro Ile Ser Val Leu Ser Thr Gly Phe Leu Val Gly Gly Gly
                20                  25                  30

Asn Pro Ala Phe Ala Ala Ser Lys Glu Ser Lys Met Pro Pro Lys Thr
            35                  40                  45

Val His Ala Gln Ala Lys Gln Ser Asn Leu Ser Thr Lys Ser Asn Ser
        50                  55                  60

Asn Leu Tyr Leu Ile Gly Asp Tyr Leu Asn Gln Arg Ile Tyr Asp Ala
65                  70                  75                  80

Val Lys Asn Arg Pro Asp Leu Phe Val Tyr Lys His Ile Gly Asp Gln
                85                  90                  95

Ser Gly Arg Thr Glu Arg Ile Ser Asp Met Asp Gln Ser Leu Gln Asn
            100                 105                 110

Gly Tyr Ile Glu Val Met Asn Ala Leu Lys Tyr Pro Gly Val Thr Ile
        115                 120                 125

Asn Asn Gly Asn Asn Ile Asp Trp Asn Gln Arg Glu Tyr Val Gly Gly
    130                 135                 140

Asp Ile Lys Val Thr Gly Lys Gln Asp Lys Val Asp Gly Leu His Ser
145                 150                 155                 160

Phe Thr Leu Gly Thr Phe His Asn Thr Gly Asp Ile Glu Gln Thr Ala
                165                 170                 175

Thr Thr Gln Lys Glu Thr Tyr Gln Thr Thr Asp Ser Phe Thr Tyr Ser
            180                 185                 190
```

```
Asn Ser Glu Gly Val Lys Leu Gly Leu Thr Glu Ser Ile Lys Ala Thr
        195                 200                 205

Ala Gly Val Pro Phe Val Ile Glu Gly Glu Glu Thr Thr Thr Ile Ser
    210                 215                 220

Ser Glu Phe Ser Tyr Asn His Thr Ser Ser Asn Thr Ser Thr Asn Ser
225                 230                 235                 240

His Thr Ile Glu Phe Pro Ser Gln Thr Ile Lys Val Lys Pro His Gly
                245                 250                 255

Thr Thr Ile Tyr Thr Gly Glu Val Lys Gln Met Asn Phe Ser Gly Asp
                260                 265                 270

Tyr Ser Gly Thr Ala Lys Leu Thr Thr Lys Asp Val Ser Phe Ala Ala
            275                 280                 285

Val Asp Thr Tyr Gly His Ile Gly Asp Val Ile Ala Ala Pro Gly Glu
        290                 295                 300

Glu Glu His Phe Leu Tyr Asn Ile Phe Lys Tyr Ser Gly Gln Ser Ile
305                 310                 315                 320

Pro Ser Asp Ile Arg Leu Asp Glu Asn Arg Met Val Val Val Asp
                325                 330                 335

Asn Ser Ser Ile His Phe Thr Gly Lys Leu Gly Phe Asn Met Glu Ala
            340                 345                 350

Thr Trp Lys Phe Ile Pro Asp Asp Pro Lys Lys Pro Ser Val Thr Ile
            355                 360                 365

Pro Asn Asp Val Tyr Leu Lys Glu Gln Ala Ser Gly Asn Ile Ser Lys
        370                 375                 380

Tyr Ile Asp Gly Leu Ile Gln Thr Lys Met Lys Ser Met His Gln
385                 390                 395
```

<210> SEQ ID NO 35
<211> LENGTH: 1089
<212> TYPE: DNA
<213> ORGANISM: Artificial Sequence
<220> FEATURE:
<223> OTHER INFORMATION: Synthetic polynucleotide

<400> SEQUENCE: 35

```
atggctagta aggaatcaaa gatgcccccc aaaaccgttc acgctcaagc gaaacaatct      60
aatttatcga ctaagtctaa tagtaactta tatcttatcg agattatttt aaatcaaaga     120
atctatgatg ctgtaaaaaa tagaccagat ttatttgttt acaaacacat tggagatcaa     180
tctggtagaa ctgaacggat tagtgacatg gatcaaagtc tacaaaatgg ttatatcgaa     240
gtaatgaatg ccttaaaata cccaggagtt acgattaaca atggaaataa tatagattgg     300
aatcaaagag aatatgttgg tggagatatc aaggtaacag gtaaacaaga taagtagat      360 ggattgcata gtttcacatt aggaactttt cataatacag gggatattga acaaactgct     420
actacgcaaa aagaaactta tcaaacgaca gatagtttta cctattcaaa tagtgagggt     480
gttaagttag gattaacaga atctataaaa gcaactgcgg gcgtaccttt tgttatagaa     540
ggcgaagaga caacaacaat ttcaagtgaa ttttcatata atcataccte ttcaaatacc     600 tcgacgaatt cacacacaat tgaatttcca tcacaaacta ttaaagtcaa acccatgga      660 actacaattt acactggaga ggtaaaacaa atgaattttt ccggagatta ctctggtaca     720
gctaaattaa caacaaagga tgtttctttt gctgcagtag atacttacgg gcatattgga     780
gatgttattg cagcaccggg agaggaagaa cattttttat ataatatttt taaatattca     840
ggccaatcaa tcccttcgga tattcgttta gatgatgaaa atagaatggt tgttgttgat     900
```

```
aattcatcca ttcattttac agggaaatta ggttttaaca tggaagccac atggaaattc    960
atccctgatg atcctaaaaa accaagtgtt acaataccaa atgatgtata tttaaaagaa   1020
caggcttctg ggaacattag caagtacatt gacggattaa tacaaactaa aatgaaatct   1080
atgcatcaa                                                           1089
```

<210> SEQ ID NO 36
<211> LENGTH: 363
<212> TYPE: PRT
<213> ORGANISM: Artificial Sequence
<220> FEATURE:
<223> OTHER INFORMATION: Synthetic polypeptide

<400> SEQUENCE: 36

```
Met Ala Ser Lys Glu Ser Lys Met Pro Pro Lys Thr Val His Ala Gln
1               5                   10                  15

Ala Lys Gln Ser Asn Leu Ser Thr Lys Ser Asn Ser Asn Leu Tyr Leu
            20                  25                  30

Ile Gly Asp Tyr Leu Asn Gln Arg Ile Tyr Asp Ala Val Lys Asn Arg
        35                  40                  45

Pro Asp Leu Phe Val Tyr Lys His Ile Gly Asp Gln Ser Gly Arg Thr
    50                  55                  60

Glu Arg Ile Ser Asp Met Asp Gln Ser Leu Gln Asn Gly Tyr Ile Glu
65                  70                  75                  80

Val Met Asn Ala Leu Lys Tyr Pro Gly Val Thr Ile Asn Asn Gly Asn
                85                  90                  95

Asn Ile Asp Trp Asn Gln Arg Glu Tyr Val Gly Gly Asp Ile Lys Val
            100                 105                 110

Thr Gly Lys Gln Asp Lys Val Asp Gly Leu His Ser Phe Thr Leu Gly
        115                 120                 125

Thr Phe His Asn Thr Gly Asp Ile Glu Gln Thr Ala Thr Thr Gln Lys
    130                 135                 140

Glu Thr Tyr Gln Thr Thr Asp Ser Phe Thr Tyr Ser Asn Ser Glu Gly
145                 150                 155                 160

Val Lys Leu Gly Leu Thr Glu Ser Ile Lys Ala Thr Ala Gly Val Pro
                165                 170                 175

Phe Val Ile Glu Gly Glu Glu Thr Thr Thr Ile Ser Ser Glu Phe Ser
            180                 185                 190

Tyr Asn His Thr Ser Ser Asn Thr Ser Thr Asn Ser His Thr Ile Glu
        195                 200                 205

Phe Pro Ser Gln Thr Ile Lys Val Lys Pro His Gly Thr Thr Ile Tyr
    210                 215                 220

Thr Gly Glu Val Lys Gln Met Asn Phe Ser Gly Asp Tyr Ser Gly Thr
225                 230                 235                 240

Ala Lys Leu Thr Thr Lys Asp Val Ser Phe Ala Ala Val Asp Thr Tyr
                245                 250                 255

Gly His Ile Gly Asp Val Ile Ala Ala Pro Gly Glu Glu His Phe
            260                 265                 270

Leu Tyr Asn Ile Phe Lys Tyr Ser Gly Gln Ser Ile Pro Ser Asp Ile
        275                 280                 285

Arg Leu Asp Asp Glu Asn Arg Met Val Val Val Asp Asn Ser Ser Ile
    290                 295                 300

His Phe Thr Gly Lys Leu Gly Phe Asn Met Glu Ala Thr Trp Lys Phe
305                 310                 315                 320
```

```
Ile Pro Asp Asp Pro Lys Lys Pro Ser Val Thr Ile Pro Asn Asp Val
            325                 330                 335

Tyr Leu Lys Glu Gln Ala Ser Gly Asn Ile Ser Lys Tyr Ile Asp Gly
        340                 345                 350

Leu Ile Gln Thr Lys Met Lys Ser Met His Gln
        355                 360

<210> SEQ ID NO 37
<211> LENGTH: 1182
<212> TYPE: DNA
<213> ORGANISM: Bacillus sp.

<400> SEQUENCE: 37
atgaagtgct ggaagaaaaa aatagctcaa gttgcaccaa tttgtgtatt aagtacagga      60
tttttagtgg gggtaggaaa tcccgctttt gcagctagta aggaatcaaa gatgagtccc     120
caaaccgttt atgctcaagc gacacaatct gatttatcga ctacgtctaa tagtaactta     180
tctcatatcg gggatgattt aaatcaaaga atccatgacg ctgtggaaaa taggcctgat     240
ttatttatat atagatatct tagggatgat aggggtagaa cgaacgtacg gatgagtgat     300
atgcctcaaa gtgacaacag tggttataac tttgtaatga atagcttaca atacggaaaa     360
gttacgatta acaatggata taatatcgat tggaatcaaa gagaatatgt cggtggagat     420
atcaaggtaa cgggtaaaca agacagcata ggtgggttgc atagttttac actaggaact     480
tttcataaca ctgaagatat tgaacaaaca gctactacgc aaaaagaaac ttatcaaaca     540
acagatagtt ttacctattc aaatagtgag ggtgtcaaat taggattgac agaatctata     600
aaagcaactg ctggtgtacc ttttgttata gcaggcgacg agacaaccac actctcaagt     660
gagttttcat ataatcatac ctcttcaaat acatcgacga actcacatac aattgaattt     720
ccatcacaga ctattaaagt caaaccgcat ggaactacaa tttacatggg tgaggtaaaa     780
caaatgaatt tttctggaga ttactctggg acagcgaaat tatcaacaaa ggatgttttct    840 ttttcaataa cggattcggg aggccattgg ggagatgtta tcgctgcgcc gggtgaagat     900
gagtattttt tatataatat attcaaatac tccggtcatc caattccttc agatattcgt     960
ttagatgatg aaaataaaac ggttgttgtt gttaattcat ccattcattt tacagggaaa    1020
ctaggtttta acatggaggc cacatggaga ttcatccctg atgatcctaa aaaaccaatt    1080
gttacaatac aaatgatgt atatttaaaa gaacaagctt ctgggaatat tagcaagtac     1140
attgaccaat taatacaaac taaaatgaaa tctatgcatc aa                       1182

<210> SEQ ID NO 38
<211> LENGTH: 394
<212> TYPE: PRT
<213> ORGANISM: Bacillus sp.

<400> SEQUENCE: 38

Met Lys Cys Trp Lys Lys Lys Ile Ala Gln Val Ala Pro Ile Cys Val
1               5                  10                  15

Leu Ser Thr Gly Phe Leu Val Gly Val Gly Asn Pro Ala Phe Ala Ala
            20                  25                  30

Ser Lys Glu Ser Lys Met Ser Pro Gln Thr Val Tyr Ala Gln Ala Thr
        35                  40                  45

Gln Ser Asp Leu Ser Thr Thr Ser Asn Ser Asn Leu Ser His Ile Gly
    50                  55                  60

Asp Asp Leu Asn Gln Arg Ile His Asp Ala Val Glu Asn Arg Pro Asp
65                  70                  75                  80
```

Leu Phe Ile Tyr Arg Tyr Leu Arg Asp Asp Arg Gly Arg Thr Asn Val
                85                  90                  95

Arg Met Ser Asp Met Pro Gln Ser Asp Asn Ser Gly Tyr Asn Phe Val
            100                 105                 110

Met Asn Ser Leu Gln Tyr Gly Lys Val Thr Ile Asn Asn Gly Tyr Asn
        115                 120                 125

Ile Asp Trp Asn Gln Arg Glu Tyr Val Gly Gly Asp Ile Lys Val Thr
    130                 135                 140

Gly Lys Gln Asp Ser Ile Gly Gly Leu His Ser Phe Thr Leu Gly Thr
145                 150                 155                 160

Phe His Asn Thr Glu Asp Ile Glu Gln Thr Ala Thr Thr Gln Lys Glu
                165                 170                 175

Thr Tyr Gln Thr Thr Asp Ser Phe Thr Tyr Ser Asn Ser Glu Gly Val
            180                 185                 190

Lys Leu Gly Leu Thr Glu Ser Ile Lys Ala Thr Ala Gly Val Pro Phe
        195                 200                 205

Val Ile Ala Gly Asp Glu Thr Thr Thr Leu Ser Ser Glu Phe Ser Tyr
    210                 215                 220

Asn His Thr Ser Ser Asn Thr Ser Thr Asn Ser His Thr Ile Glu Phe
225                 230                 235                 240

Pro Ser Gln Thr Ile Lys Val Lys Pro His Gly Thr Thr Ile Tyr Met
                245                 250                 255

Gly Glu Val Lys Gln Met Asn Phe Ser Gly Asp Tyr Ser Gly Thr Ala
            260                 265                 270

Lys Leu Ser Thr Lys Asp Val Ser Phe Ser Ile Thr Asp Ser Gly Gly
        275                 280                 285

His Trp Gly Asp Val Ile Ala Ala Pro Gly Glu Asp Glu Tyr Phe Leu
    290                 295                 300

Tyr Asn Ile Phe Lys Tyr Ser Gly His Pro Ile Pro Ser Asp Ile Arg
305                 310                 315                 320

Leu Asp Asp Glu Asn Lys Thr Val Val Val Asn Ser Ser Ile His
                325                 330                 335

Phe Thr Gly Lys Leu Gly Phe Asn Met Glu Ala Thr Trp Arg Phe Ile
            340                 345                 350

Pro Asp Asp Pro Lys Lys Pro Ile Val Thr Ile Pro Asn Asp Val Tyr
        355                 360                 365

Leu Lys Glu Gln Ala Ser Gly Asn Ile Ser Lys Tyr Ile Asp Gln Leu
    370                 375                 380

Ile Gln Thr Lys Met Lys Ser Met His Gln
385                 390

<210> SEQ ID NO 39
<211> LENGTH: 1092
<212> TYPE: DNA
<213> ORGANISM: Artificial Sequence
<220> FEATURE:
<223> OTHER INFORMATION: Synthetic polynucleotide

<400> SEQUENCE: 39
atggctagta aggaatcaaa gatgagtccc caaaccgttt atgctcaagc gacacaatct    60
gatttatcga ctacgtctaa tagtaactta tctcatatcg ggatgatttt aaatcaaaga   120
atccatgacg ctgtggaaaa taggcctgat ttatttatat atagatatct tagggatgat   180
aggggtagaa cgaacgtacg gatgagtgat atgcctcaaa gtgacaacag tggttataac   240

| | |
|---|---:|
| tttgtaatga atagcttaca atacggaaaa gttacgatta acaatggata taatatcgat | 300 |
| tggaatcaaa gagaatatgt cggtggagat atcaaggtaa cgggtaaaca agacagcata | 360 |
| ggtgggttgc atagttttac actaggaact tttcataaca ctgaagatat tgaacaaaca | 420 |
| gctactacgc aaaaagaaac ttatcaaaca acagatagtt ttacctattc aaatagtgag | 480 |
| ggtgtcaaat taggattgac agaatctata aaagcaactg ctggtgtacc ttttgttata | 540 |
| gcaggcgacg agacaaccac actctcaagt gagttttcat ataatcatac ctcttcaaat | 600 |
| acatcgacga actcacatac aattgaattt ccatcacaga ctattaaagt caaaccgcat | 660 |
| ggaactacaa tttacatggg tgaggtaaaa caaatgaatt tttctggaga ttactctggg | 720 |
| acagcgaaat tatcaacaaa ggatgtttct ttttcaataa cggattcggg aggccattgg | 780 |
| ggagatgtta tcgctgcgcc gggtgaagat gagtattttt tatataatat attcaaatac | 840 |
| tccggtcatc caattccttc agatattcgt ttagatgatg aaaataaaac ggttgttgtt | 900 |
| gttaattcat ccattcattt tacagggaaa ctaggtttta acatggaggc cacatggaga | 960 |
| ttcatccctg atgatcctaa aaaaccaatt gttacaatac caatgatgt atatttaaaa | 1020 |
| gaacaagctt ctgggaatat tagcaagtac attgaccaat taatacaaac taaaatgaaa | 1080 |
| tctatgcatc aa | 1092 |

<210> SEQ ID NO 40
<211> LENGTH: 364
<212> TYPE: PRT
<213> ORGANISM: Artificial Sequence
<220> FEATURE:
<223> OTHER INFORMATION: Synthetic polypeptide

<400> SEQUENCE: 40

Met Ala Ser Lys Glu Ser Lys Met Ser Pro Gln Thr Val Tyr Ala Gln
1               5                   10                  15

Ala Thr Gln Ser Asp Leu Ser Thr Thr Ser Asn Ser Asn Leu Ser His
            20                  25                  30

Ile Gly Asp Asp Leu Asn Gln Arg Ile His Asp Ala Val Glu Asn Arg
        35                  40                  45

Pro Asp Leu Phe Ile Tyr Arg Tyr Leu Arg Asp Arg Gly Arg Thr
    50                  55                  60

Asn Val Arg Met Ser Asp Met Pro Gln Ser Asp Asn Ser Gly Tyr Asn
65                  70                  75                  80

Phe Val Met Asn Ser Leu Gln Tyr Gly Lys Val Thr Ile Asn Asn Gly
                85                  90                  95

Tyr Asn Ile Asp Trp Asn Gln Arg Glu Tyr Val Gly Gly Asp Ile Lys
            100                 105                 110

Val Thr Gly Lys Gln Asp Ser Ile Gly Gly Leu His Ser Phe Thr Leu
        115                 120                 125

Gly Thr Phe His Asn Thr Glu Asp Ile Glu Gln Thr Ala Thr Thr Gln
    130                 135                 140

Lys Glu Thr Tyr Gln Thr Thr Asp Ser Phe Thr Tyr Ser Asn Ser Glu
145                 150                 155                 160

Gly Val Lys Leu Gly Leu Thr Glu Ser Ile Lys Ala Thr Ala Gly Val
                165                 170                 175

Pro Phe Val Ile Ala Gly Asp Glu Thr Thr Thr Leu Ser Ser Glu Phe
            180                 185                 190

Ser Tyr Asn His Thr Ser Ser Asn Thr Ser Thr Asn Ser His Thr Ile
        195                 200                 205

-continued

```
Glu Phe Pro Ser Gln Thr Ile Lys Val Lys Pro His Gly Thr Thr Ile
    210             215                 220
Tyr Met Gly Glu Val Lys Gln Met Asn Phe Ser Gly Asp Tyr Ser Gly
225             230                 235                 240
Thr Ala Lys Leu Ser Thr Lys Asp Val Ser Phe Ser Ile Thr Asp Ser
                245                 250                 255
Gly Gly His Trp Gly Asp Val Ile Ala Ala Pro Gly Glu Asp Glu Tyr
            260                 265                 270
Phe Leu Tyr Asn Ile Phe Lys Tyr Ser Gly His Pro Ile Pro Ser Asp
        275                 280                 285
Ile Arg Leu Asp Asp Glu Asn Lys Thr Val Val Val Val Asn Ser Ser
    290                 295                 300
Ile His Phe Thr Gly Lys Leu Gly Phe Asn Met Glu Ala Thr Trp Arg
305             310                 315                 320
Phe Ile Pro Asp Asp Pro Lys Lys Pro Ile Val Thr Ile Pro Asn Asp
                325                 330                 335
Val Tyr Leu Lys Glu Gln Ala Ser Gly Asn Ile Ser Lys Tyr Ile Asp
            340                 345                 350
Gln Leu Ile Gln Thr Lys Met Lys Ser Met His Gln
        355                 360
```

PESTICIDAL GENES AND METHODS OF USE

CROSS-REFERENCE TO RELATED APPLICATIONS

This application claims priority to U.S. Provisional Application Nos. 63/117,797, filed Nov. 24, 2020, and 63/140,058, filed Jan. 21, 2021, each of which is incorporated by reference herein in its entirety.

STATEMENT REGARDING THE SEQUENCE LISTING

The Sequence Listing associated with this application is provided in ASCII format in lieu of a paper copy, and is hereby incorporated by reference into the specification. The ASCII copy named A101100_1660US_1_0547_7_SL is 93,134 bytes in size, was created on Nov. 24, 2021, and is being submitted electronically via EFS-Web.

FIELD OF THE INVENTION

The invention is drawn to methods and compositions for controlling pests, particularly plant pests.

BACKGROUND

Pests, plant diseases, and weeds can be serious threats to crops. Losses due to pests and diseases have been estimated at 37% of the agricultural production worldwide, with 13% due to insects, bacteria and other organisms.

Toxins are virulence determinants that play an important role in microbial pathogenicity and/or evasion of the host immune response. Toxins from the gram-positive bacterium *Bacillus*, particularly *Bacillus thuringiensis*, have been used as insecticidal proteins. Current strategies use the genes expressing these toxins to produce transgenic crops. Transgenic crops expressing insecticidal protein toxins are used to combat crop damage from insects.

While the use of *Bacillus* toxins has been successful in controlling insects, resistance to Bt toxins has developed in some target pests in many parts of the world where such toxins have been used intensively. One way of solving this problem is sowing Bt crops with alternating rows of regular non Bt crops (refuge). An alternative method to avoid or slow down development of insect resistance is stacking insecticidal genes with different modes of action against insects in transgenic plants. The current strategy of using transgenic crops expressing insecticidal protein toxins is placing increasing emphasis on the discovery of novel toxins, beyond those already derived from the bacterium *Bacillus thuringiensis*. These toxins may prove useful as alternatives to those derived from *B. thuringiensis* for deployment in insect- and pest-resistant transgenic plants. Thus, new toxin proteins are needed.

SUMMARY

Compositions having pesticidal activity and methods for their use are provided. Compositions include polypeptide sequences including isolated and recombinant polypeptide sequences having pesticidal activity, nucleic acid molecules including isolated, recombinant, and synthetic nucleic acid molecules encoding the pesticidal polypeptides, DNA constructs comprising the nucleic acid molecules, vectors comprising the nucleic acid molecules, host cells comprising the DNA constructs or vectors, and antibodies to the pesticidal polypeptides. Nucleotide sequences encoding the polypeptides provided herein can be used in DNA constructs or expression cassettes for transformation and expression in organisms of interest, including microorganisms and plants.

The compositions and methods provided herein are useful for the production of organisms with enhanced pest resistance or tolerance. These organisms and compositions comprising the organisms are desirable for agricultural purposes. Transgenic plants and seeds comprising a nucleotide sequence that encodes a pesticidal protein of the invention are also provided. Such plants are resistant to insects and other pests.

Methods are provided for producing the various polypeptides disclosed herein, and for using those polypeptides for controlling or killing a pest. Methods and kits for detecting polypeptides of the invention in a sample are also included.

DETAILED DESCRIPTION OF THE INVENTION

The present inventions now will be described more fully hereinafter, in which some, but not all embodiments of the inventions are described. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Polynucleotides and Polypeptides

Compositions and method for conferring pesticidal activity to an organism are provided. The modified organism exhibits pesticidal resistance or tolerance. Recombinant pesticidal proteins, or polypeptides and fragments and variants thereof that retain pesticidal activity, are provided and include those set forth in SEQ ID NOs: 2, 4, 6, 8, 10, 12, 14, 16, 18, 20, 22, 24, 26, 28, 30, 32, 34, 36, 38, and/or 40. The pesticidal proteins are biologically active (e.g., pesticidal) against pests including insects, fungi, nematodes, and the like. Nucleotide sequences encoding the pesticidal polypeptides are provided and include those set forth in SEQ ID NOs: 1, 3, 5, 7, 9, 11, 13, 15, 17, 19, 21, 23, 25, 27, 29, 31, 33, 35, 37, and/or 39. Nucleotide sequences encoding the pesticidal polypeptides, including for example, SEQ ID NOs: 2, 4, 6, 8, 10, 12, 14, 16, 18, 20, 22, 24, 26, 28, 30, 32, 34, 36, 38, and/or 40, or active fragments or variants thereof, can be used to produce transgenic organisms, such as plants and microorganisms. The pesticidal proteins are biologically active (for example, are pesticidal) against pests including insects, fungi, nematodes, and the like. In specific embodiments, the pesticidal polypeptides and the active variant and fragments thereof have an improved pesticidal activity when compared to other polypeptides in the art. Polynucleotides encoding the pesticidal polypeptides, including for example, SEQ ID NOs: 2, 4, 6, 8, 10, 12, 14, 16, 18, 20, 22, 24, 26, 28, 30, 32, 34, 36, 38, and/or 40, or active fragments or variants thereof, can be used to produce transgenic organisms, such as plants and microorganisms. The transformed organisms are characterized by genomes that comprise at least one stably incorporated DNA construct comprising a coding sequence for a pesticidal protein disclosed herein. In some embodiments, the coding sequence is operably linked to a promoter that drives expression of the encoded pesticidal polypeptide. Accordingly, transformed microorganisms, plant cells, plant tissues, plants, seeds, and plant parts are provided. A summary of various polypeptides, active variants and fragments thereof, and polynucleotides encoding the same are set forth below in Table 1. As noted in Table 1, various forms of polypeptides are provided. Full length pesticidal polypeptides, as well as, modified versions of the original full-length sequence (i.e., variants) are provided.

TABLE 1

Summary of SEQ ID NOs, Gene Class, and Variants thereof

| Gene Name | Full-Length AA Seq ID NO: | Modified Seq ID NO(s): (AA) | Full-Length NT Seq ID NO: | Modified Seq ID NO(s): (NT) | Gene Class | Polypeptides of the invention (and polynucleotides encoding the same) include those having the % sequence identity listed below | Polypeptides of the invention (and polynucleotides encoding the same) include those having the similarity set forth below | Homologs |
|---|---|---|---|---|---|---|---|---|
| APG06396.0 | 2 | | 1 | | None | 96, 97, 98, 99 | 98, 99 | US_10563221_B2-18 (89.1% identity, 95.5% similarity) ASU02572.1 (95.9% identity, 97.7% similarity) WP_032687670.1 (89.8% identity, 96.2% similarity) WP_104897205.1 (89.5% identity, 95.9% similarity) WP_004862099.1 (89.1% identity, 95.5% similarity) WP_099843532.1 (89.1% identity, 95.5% similarity) WP_143958929.1 (88.7% identity, 95.5% similarity) WP_06590652.1 (88.7% identity, 95.1% similarity) WP_086816612.1 (88.7% identity, 95.1% similarity) WP_126509679.1 (88.7% identity, 95.1% similarity) VTNO5288.1 (85.3% identity, 91.6% similarity) WP_127156625.1 (61.3% identity, 77.1% similarity) |
| APG03083.0 | 4 | 6 | 3 | 5 | MTX | 5, 10, 15, 20, 25, 30, 35, 40, 45, 50, 55, 60, 65, 70, 75, 80, 85, 90, 91, 92, 93, 94, 95, 96, 97, 98, 99, 100 | 5, 10, 15, 20, 25, 30, 35, 40, 45, 50, 55, 60, 65, 70, 75, 80, 85, 90, 91, 92, 93, 94, 95, 96, 97, 98, 99, 100 | WP_115617104.1 (99.3% identity, 99.5% similarity) WP_082107019.1 (99.1% identity, 99.5% similarity) WP_083340378.1 (99.1% identity, 99.5% similarity) WP_082113612.1 (99.1% identity, 99.3% similarity) WP_104947115.1 (97.7% identity, 99.3% similarity) WP_021478451.1 (96.6% identity, 98.6% similarity) AOZ48749.1 (96.3% identity, 96.8% similarity) WP_166440583.1 (94.1% identity, 94.1% similarity) WP_158300673.1 (93% identity, 97% similarity) WP_149295541.1 (92.2% identity, 96.8% similarity) AUH50741.1 (91.8% identity, 95.9% similarity) WP_083340813.1 (90.6% identity, 97.7% similarity) WP_106076690.1 (90.4% identity, 96.8% similarity) OHX17593.1 (90.4% identity, 97.7% similarity) WP_103321067.1 (90.2% identity, 96.1% similarity) |
| APG05736.0 | 8 | 10, 12 | 7 | 9, 11 | MTX | 93, 94, 95, 96, 97, 98, 99, 100 | 97, 98, 99, 100 | WP_105700415.1 (93.3% identity, 96.7% similarity) WP_077413348.1 (93% identity, 96.4% similarity) |

TABLE 1-continued

Summary of SEQ ID NOs, Gene Class, and Variants thereof

| Gene Name | Full-Length AA Seq ID NO: | Modified Seq ID NO(s): (AA) | Full-Length NT Seq ID NO: | Modified Seq ID NO(s): (NT) | Gene Class | Polypeptides of the invention (and polynucleotides encoding the same) include those having the % sequence identity listed below | Polypeptides of the invention (and polynucleotides encoding the same) include those having the similarity set forth below | Homologs |
|---|---|---|---|---|---|---|---|---|
| APG02668.0 | 14 | 16 | 13 | 15 | MTX | 95, 96, 97, 98, 99, 100 | 98, 99, 100 | US_2018_0066277_A1-252 (ABI) (92.1% identity, 95.4% similarity) US_2018_0066277_A1-71 (ABI) (92.1% identity, 95.7% similarity) PTT42759.1 (92.1% identity, 95.4% similarity) WP_152289117.1 (91.5% identity, 95.4% similarity) WP_124532695.1 (91.2% identity, 95.4% similarity) WP_103234958.1 (90.6% identity, 94.8% similarity) WP_110009090.1 (96.7% identity, 98.5% similarity) QBA23031.1 (96.4% identity, 98.8% similarity) WP_142018293.1 (95.2% identity, 97.6% similarity) WP_047426867.1 (94.8% identity, 97.3% similarity) US_2018_0291068_A1-74 (ABI) (94.5% identity, 97% similarity) WP_114819731.1 (93.9% identity, 97% similarity) US_2018_0291068_A1-409 (ABI) (93.6% identity, 97.9% similarity) WP_062673074.1 (93.6% identity, 97.6% similarity) WP_120232414.1 (93.6% identity, 97.9% similarity) WP_123278643.1 (93.6% identity, 97.6% similarity) WP_079243808.1 (93.3% identity, 97.6% similarity) TXI91014.1 (93% identity, 97.3% similarity) WP_136522012.1 (92.4% identity, 95.2% similarity) WP_076596488.1 (92.1% identity, 94.8% similarity) WP_110366584.1 (92.1% identity, 95.2% similarity) |
| APG06377.0 | 18 | 20 | 17 | 19 | MTX | 95, 96, 97, 98, 99, 100 | 99, 100 | WP_114819731.1 (97.6% identity, 98.8% similarity) WP_110009090.1 (96.4% identity, 98.5% similarity) QBA23031.1 (95.5% identity, 98.8% similarity) WP_123278643.1 (94.8% identity, 98.2% similarity) US_2018_0291068_A1-411 (ABI) (94.7% identity, 98.4% similarity) US_2018_0291068_A1-410 (ABI) (94.7% identity, 98.4% similarity) US_2018_0291068_A1-409 (ABI) (94.5% identity, 98.2% similarity) WP_062673074.1 (94.5% identity, 97.9% similarity) WP_120232414.1 (94.5% identity, 98.2% similarity) TXI91014.1 (93.9% identity, 97.6% similarity) WP_142018293.1 (92.7% identity, 97% similarity) WP_047426867.1 (92.4% identity, 96.7% similarity) WP_136522012.1 (92.4% identity, 95.2% similarity) US_2018_0291068_A1-74 (ABI) (92.1% identity, 96.4% similarity) |

TABLE 1-continued

Summary of SEQ ID NOs, Gene Class, and Variants thereof

| Gene Name | Full-Length AA Seq ID NO: | Modified Seq ID NO(s): (AA) | Full-Length NT Seq ID NO: | Modified Seq ID NO(s): (NT) | Gene Class | Polypeptides of the invention (and polynucleotides encoding the same) include those having the % sequence identity listed below | Polypeptides of the invention (and polynucleotides encoding the same) include those having the similarity set forth below | Homologs |
|---|---|---|---|---|---|---|---|---|
| APG08037.0 | 22 | 24 | 21 | 23 | MTX | 90, 91, 92, 93, 94, 95, 96, 97, 98, 99, 100 | 96, 97, 98, 99, 100 | WP_076596488.1 (92.1% identity, 94.8% similarity) WP_110366584.1 (92.1% identity, 95.2% similarity) WP_079243808.1 (91.2% identity, 96.4% similarity) WP_105683074.1 (98.2% identity, 99.7% similarity) WP_114819731.1 (89.7% identity, 95.5% similarity) WP_142018293.1 (89.4% identity, 95.8% similarity) US_2018_0291068_A1-74 (ABI) (89.4% identity, 95.8% similarity) WP_047426867.1 (89.1% identity, 95.5% similarity) QBA23031.1 (88.5% identity, 95.2% similarity) WP_136522012.1 (88.5% identity, 95.5% similarity) WP_076596488.1 (88.2% identity, 95.2% similarity) WP_110366584.1 (88.2% identity, 95.5% similarity) WP_110009090.1 (87.9% identity, 94.8% similarity) US_2018_0291068_A1-411 (ABI) (87.8% identity, 95.4% similarity) US_2018_0291068_A1-410 (ABI) (87.8% identity, 95.4% similarity) WP_062673074.1 (87.6% identity, 94.5% similarity) WP_120232414.1 (87.6% identity, 94.8% similarity) WP_123278643.1 (87.6% identity, 94.5% similarity) US_2018_0291068_A1-409 (ABI) (87.6% identity, 94.8% similarity) TXI91014.1 (87% identity, 94.2% similarity) WP_079243808.1 (87% identity, 95.2% similarity) WP_129038837.1 (86.2% identity, 93.1% similarity) WP_077413348.1 (86.1% identity, 92.1% similarity) PTT42759.1 (85.8% identity, 92.7% similarity) WP_105700415.1 (85.8% identity, 92.7% similarity) US_2018_0066277_A1-252 (ABI) (85.8% identity, 92.7% similarity) US_2018_0066277_A1-71 (ABI) (85.5% identity, 91.8% similarity) WP_152289117.1 (85.2% identity, 92.4% similarity) |
| APG03548.0 | 26 | 28, 30 | 25 | 27, 29 | MTX | 90, 91, 92, 93, 94, 95, 96, 97, 98, 99, 100 | 92, 93, 94, 95, 96, 97, 98, 99, 100 | US_2016_0355842_A1-150 (ABI) (88.9% identity, 91.6% similarity) US_2017_0137842_A1-1 (87.1% identity, 92.1% similarity) US_2017_0137842_A1-2 (87.1% identity, 92.1% similarity) US_2017_0137842_A1-25 (86.9% identity, 92.3% similarity) US_2017_0137842_A1-26 (86.9% identity, 92.3% similarity) US_2016_0355842_A1-176 (ABI) (86.9% identity, 92.4% similarity) WP_098259338.1 (86.8% identity, 92.3% similarity) |

TABLE 1-continued

Summary of SEQ ID NOs, Gene Class, and Variants thereof

| Gene Name | Full-Length AA Seq ID NO: | Modified Seq ID NO(s): (AA) | Full-Length NT Seq ID NO: | Modified Seq ID NO(s): (NT) | Gene Class | Polypeptides of the invention (and polynucleotides encoding the same) include those having the % sequence identity listed below | Polypeptides of the invention (and polynucleotides encoding the same) include those having the similarity set forth below | Homologs |
|---|---|---|---|---|---|---|---|---|
| APG04564.0 | 32 | 34, 36 | 31 | 33, 35 | MTX | 90, 91, 92, 93, 94, 95, 96, 97, 98, 99, 100 | 90, 91, 92, 93, 94, 95, 96, 97, 98, 99, 100 | WP_098873554.1 (86.8% identity, 92.1% similarity) WP_087094398.1 (83.2% identity, 89.1% similarity) WP_087094398.1 (89.2% identity, 93.3% similarity) SCN30318.1 (88% identity, 91% similarity) US_2016_0355842_A1-150 (ABI) (85.3% identity, 88.6% similarity) US_2017_0137842_A1-1 (84.5% identity, 89.8% similarity) US_2017_0137842_A1-2 (84.5% identity, 89.8% similarity) WP_098259338.1 (84.2% identity, 90% similarity) WP_098873554.1 (84.2% identity, 89.8% similarity) US_2016_0355842_A1-176 (ABI) (84.1% identity, 90.1% similarity) US_2017_0137842_A1-25 (82.8% identity, 88% similarity) US_2017_0137842_A1-26 (82.8% identity, 88% similarity) |
| APG03088.0 | 38 | 40 | 37 | 39 | MTX | 93, 94, 95, 96, 97, 98, 99, 100 | 98, 99, 100 | US_2017_0137842_A1-1 (92.6% identity, 97.2% similarity) US_2017_0137842_A1-2 (92.6% identity, 97.2% similarity) US_2016_0355842_A1-176 (ABI) (92.4% identity, 97.5% similarity) WP_098259338.1 (92.4% identity, 97.5% similarity) WP_098873554.1 (92.4% identity, 97.2% similarity) US_2017_0137842_A1-25 (90.8% identity, 95.3% similarity) US_2017_0137842_A1-26 (90.8% identity, 95.3% similarity) | i. Classes of Pesticidal Proteins

The pesticidal proteins provided herein and the nucleotide sequences encoding them are useful in methods for impacting pests. That is, the compositions and methods of the invention find use in agriculture for controlling or killing pests, including pests of many crop plants. The pesticidal proteins provided herein are toxin proteins from bacteria and exhibit activity against certain pests. The pesticidal proteins are from several classes of toxins including Cry, Cyt, BIN, and Mtx toxins. See, for example, Table 1 for the specific protein classifications of the various SEQ ID NOs provided herein. In addition, reference is made throughout this disclosure to Pfam database entries. The Pfam database is a database of protein families, each represented by multiple sequence alignments and a profile hidden Markov model. Finn et al. (2014) *Nucl. Acid Res.* Database Issue 42:D222-D230.

*Bacillus thuringiensis* (Bt) is a gram-positive bacterium that produces insecticidal proteins as crystal inclusions during its sporulation phase of growth. The proteinaceous inclusions of *Bacillus thuringiensis* (Bt) are called crystal proteins or S-endotoxins (or Cry proteins), which are toxic to members of the class Insecta and other invertebrates. Similarly, Cyt proteins are parasporal inclusion proteins from Bt that exhibit hemolytic (cytolytic) activity or have obvious sequence similarity to a known Cyt protein. These toxins are highly specific to their target organism, but are innocuous to humans, vertebrates, and plants.

The structure of the Cry toxins reveals five conserved amino acid blocks, concentrated mainly in the center of the domain or at the junction between the domains. The Cry toxin consists of three domains, each with a specific function. Domain I is a seven α-helix bundle in which a central helix is completely surrounded by six outer helices. This domain is implicated in channel formation in the membrane. Domain II appears as a triangular column of three antiparallel β-sheets, which are similar to antigen-binding regions of immunoglobulins. Domain III contains antiparallel β-strands in a R sandwich form. The N-terminal part of the toxin protein is responsible for its toxicity and specificity and contains five conserved regions. The C-terminal part is usually highly conserved and probably responsible for crystal formation. See, for example, U.S. Pat. No. 8,878,007.

Strains of *B. thuringiensis* show a wide range of specificity against different insect orders (Lepidoptera, Diptera, Coleoptera, Hymenoptera, Homoptera, Phthiraptera or Mallophaga, and Acari) and other invertebrates (Nemathelminthes, Platyhelminthes, and Sarocomastebrates). The Cry proteins have been classified into groups based on toxicity to various insect and invertebrate groups. Generally, Cry I demonstrates toxicity to lepidopterans, Cry II to lepidopterans and dipterans, CryIII to coleopterans, Cry IV to dipterans, and Cry V and Cry VI to nematodes. New Cry proteins can be identified and assigned to a Cry group based on amino acid identity. See, for example, Bravo, A. (1997) *J. of Bacteriol.* 179:2793-2801; Bravo et al. (2013) *Microb. Biotechnol.* 6:17-26, herein incorporated by reference.

Over 750 different cry gene sequences have been classified into 73 groups (Cry1-Cry73), with new members of this gene family continuing to be discovered (Crickmore et al. (2014) www.btnomenclature.info/). The cry gene family consists of several phylogenetically non-related protein families that may have different modes of action: the family of three-domain Cry toxins, the family of mosquitocidal Cry toxins, the family of the binary-like toxins, and the Cyt family of toxins (Bravo et al., 2005). Some Bt strains produce additional insecticidal toxins, the VIP toxins. See, also, Cohen et al. (2011) *J. Mol. Biol.* 413:4-814; Crickmore et al. (2014) *Bacillus thuringiensis* toxin nomenclature, found on the world wide web at lifesci.sussex.ac.uk/home/Neil_Crickmore/Bt/; Crickmore et al. (1988) *Microbiol. Mol. Biol. Rev.* 62: 807-813; Gill et al. (1992) *Ann. Rev. Entomol.* 37: 807-636; Goldbert et al. (1997) *Appl. Environ. Microbiol.* 63:2716-2712; Knowles et al. (1992) *Proc. R. Soc. Ser. B.* 248: 1-7; Koni et al. (1994) *Microbiology* 140: 1869-1880; Lailak et al. (2013) *Biochem. Biophys. Res. Commun.* 435: 216-221; Lopez-Diaz et al. (2013) *Environ. Microbiol.* 15: 3030-3039; Perez et al. (2007) *Cell. Microbiol.* 9: 2931-2937; Promdonkoy et al. (2003) *Biochem. J.* 374: 255-259; Rigden (2009) *FEBS Lett.* 583: 1555-1560; Schnepf et al. (1998) *Microbiol. Mol. Biol. Rev.* 62: 775-806; Soberon et al. (2013) *Peptides* 41: 87-93; Thiery et al. (1998) *J. Am. Mosq. Control Assoc.* 14: 472-476; Thomas et al. (1983) *FEBS Lett.* 154: 362-368; Wirth et al. (1997) *Proc. Natl. Acad. Sci. U.S.A.* 94: 10536-10540; Wirth et al (2005) *Appl. Environ. Microbiol.* 71: 185-189; and, Zhang et al. (2006) *Biosci. Biotechnol. Biochem.* 70: 2199-2204; each of which is herein incorporated by reference in their entirety.

Cyt designates a parasporal crystal inclusion protein from *Bacillus thuringiensis* with cytolytic activity, or a protein with sequence similarity to a known Cyt protein. (Crickmore et al. (1998) *Microbiol. Mol. Biol. Rev.* 62: 807-813). The gene is denoted by cyt. These proteins are different in structure and activity from Cry proteins (Gill et al. (1992) *Annu. Rev. Entomol.* 37: 615-636). The Cyt toxins were first discovered in *B. thuringiensis* subspecies *israelensis* (Goldberg et al. (1977) *Mosq. News.* 37: 355-358). There are 3 Cyt toxin families including 11 holotype toxins in the current nomenclature (Crickmore et al. (2014) *Bacillus thuringiensis* toxin nomenclature found on the world wide web at lifesci.sussex.ac.uk/home/Neil_Crickmore/Bt/). The majority of the *B. thuringiensis* isolates with cyt genes show activity against dipteran insects (particularly mosquitoes and black flies), but there are also cyt genes that have been described in *B. thuringiensis* strains targeting lepidopteran or coleopteran insects (Guerchicoff et al. (1997) *Appl. Environ. Microbiol.* 63: 2716-2721).

The structure of Cyt2A, solved by X-ray crystallography, shows a single domain where two outer layers of α-helix wrap around a mixed β-sheet. Further available crystal structures of Cyt toxins support a conserved α-β structural model with two α-helix hairpins flanking a β-sheet core containing seven to eight β-strands. (Cohen et al. (2011) *J. Mol. Biol.* 413: 80 4-814) Mutagenic studies identified β-sheet residues as critical for toxicity, while mutations in the helical domains did not affect toxicity (Adang et al.; Diversity of *Bacillus thuringiensis* Crystal Toxins and Mechanism of Action. In: T. S. Dhadialla and S. S. Gill, eds, *Advances in Insect Physiology, Vol.* 47, Oxford: Academic Press, 2014, pp. 39-87.) The representative domain of the Cyt toxin is a 6-endotoxin, Bac_thur_toxin (Pfam PF01338).

There are multiple proposed models for the mode of action of Cyt toxins, and it is still an area of active investigation. Some Cyt proteins (Cyt1A) have been shown to require the presence of accessory proteins for crystallization. Cyt1A and Cyt2A protoxins are processed by digestive proteases at the same sites in the N- and C-termini to a stable toxin core. Cyt toxins then interact with non-saturated membrane lipids, such as phosphatidylcholine, phosphatidylethanolamine, and sphingomyelin. For Cyt toxins, pore-formation and detergent-like membrane disruption have been proposed as non-exclusive mechanisms; and it is generally accepted that both may occur depending on toxin concentration, with lower concentrations favoring oligomeric pores and higher concentrations leading to membrane breaks. (Butko (2003) *Appl. Environ. Microbiol.* 69: 2415-2422) In the pore-formation model, the Cyt toxin binds to the cell membrane, inducing the formation of cation-selective channels in the membrane vesicles leading to colloid-osmotic lysis of the cell. (Knowles et al. (1989) *FEBS Lett.* 244: 259-262; Knowles et al. (1992) *Proc. R. Soc. Ser. B.* 248: 1-7 and Promdonkoy et al. (2003) *Biochem. J.* 374: 255-259). In the detergent model, there is a nonspecific aggregation of the toxin on the surface of the lipid bilayer leading to membrane disassembly and cell death. (Butko (2003) supra; Manceva et al. (2005) *Biochem.* 44: 589-597).

Multiple studies have shown synergistic activity between Cyt toxins and other *B. thuringiensis* toxins, particularly the Cry, Bin, and Mtx toxins. This synergism has even been shown to overcome an insect's resistance to the other toxin. (Wirth 1997, Wirth 2005, Thiery 1998, Zhang 2006) The Cyt synergistic effect for Cry toxins is proposed to involve Cyt1A binding to domain II of Cry toxins in solution or on the membrane plane to promote formation of a Cry toxin pre-pore oligomer. Formation of this oligomer is independent of the Cyt oligomerization, binding or insertion. (Lailak 2013, Perez 2007, Lopez-Diaz 2013)

A number of pesticidal proteins unrelated to the Cry proteins are produced by some strains of *B. thuringiensis* and *B. cereus* during vegetative growth (Estruch et al. (1996) *Proc Natl Acad Sci USA* 93:5389-5394; Warren et al. (1994) WO 94/21795). These vegetative insecticidal proteins, or Vips, do not form parasporal crystal proteins and are apparently secreted from the cell. The Vips are presently excluded from the Cry protein nomenclature because they are not crystal-forming proteins. The term VIP is a misnomer in the sense that some *B. thuringiensis* Cry proteins are also produced during vegetative growth as well as during the stationary and sporulation phases, most notably Cry3Aa. The location of the Vip genes in the *B. thuringiensis* genome has been reported to reside on large plasmids that also encode cry genes (Mesrati et al. (2005) *FEMS Microbiol. Lett.* 244(2):353-8). A web-site for the nomenclature of Bt toxins can be found on the world wide web at lifesci.sussex.ac.uk with the path "/home/Neil_Crickmore/Bt/" and at: "btnomenclature.info/". See also, Schnepf et al. (1998) *Microbiol. Mol. Biol. Rev.* 62(3):775-806. Such references are herein incorporated by reference.

Vip genes can be classified into 4 categories. Some Vip genes form binary two-component protein complexes; an "A" component is usually the "active" portion, and a "B"

component is usually the "binding" portion. (Pfam pfam.xfam.org/family/PF03495). The Vip1 and Vip4 proteins generally contain binary toxin B protein domains. Vip2 proteins generally contain binary toxin A protein domains.

The Vip1 and Vip2 proteins are the two components of a binary toxin that exhibits toxicity to coleopterans. Vip1Aa1 and Vip2Aa1 are very active against corn rootworms, particularly *Diabrotica virgifera* and *Diabrotica longicornis* (Han et al. (1999) *Nat. Struct. Biol.* 6:932-936; Warren G W (1997) "Vegetative insecticidal proteins: novel proteins for control of corn pests" In: Carozzi N B, Koziel M (eds) *Advances in insect control, the role of transgenic plants*; Taylor & Francis Ltd, London, pp 109-21). The membrane-binding 95 kDa Vip1 multimer provides a pathway for the 52 kDa vip2 ADP-ribosylase to enter the cytoplasm of target western corn rootworm cells (Warren (1997) supra). The NAD-dependent ADP-ribosyltransferase Vip2 likely modifies monomeric actin at Arg177 to block polymerization, leading to loss of the actin cytoskeleton and eventual cell death due to the rapid subunit exchange within actin filaments in vivo (Carlier M. F. (1990) *Adv. Biophys.* 26:51-73).

Like Cry toxins, activated Vip3A toxins are pore-forming proteins capable of making stable ion channels in the membrane (Lee et al. (2003) *Appl. Environ. Microbiol.* 69:4648-4657). Vip3 proteins are active against several major lepidopteran pests (Rang et al. (2005) *Appl. Environ. Microbiol.* 71(10):6276-6281; Bhalla et al. (2005) *FEMS Microbiol. Lett.* 243:467-472; Estruch et al. (1998) WO 9844137; Estruch et al. (1996) *Proc Natl Acad Sci USA* 93:5389-5394; Selvapandiyan et al. (2001) *Appl. Environ Microbiol.* 67:5855-5858; Yu et al. (1997) *Appl. Environ Microbiol.* 63:532-536). Vip3A is active against *Agrotis ipsilon, Spodoptera frugiperda, Spodoptera exigua, Heliothis virescens*, and *Helicoverpa zea* (Warren et al. (1996) WO 96/10083; Estruch et al. (1996) *Proc Natl Acad Sci USA* 93:5389-5394). Like Cry toxins, Vip3A proteins must be activated by proteases prior to recognition at the surface of the midgut epithelium of specific membrane proteins different from those recognized by Cry toxins.

The MTX family of toxin proteins is characterized by the presence of a conserved domain, ETX_MTX2 (pfam 03318). Members of this family share sequence homology with the mosquitocidal toxins Mtx2 and Mtx3 from *Bacillus sphaericus*, as well as with the epsilon toxin ETX from *Clostridium perfringens* (Cole et al. (2004) *Nat. Struct. Mol. Biol.* 11: 797-8; Thanabalu et al. (1996) *Gene* 170:85-9). The MTX-like proteins are structurally distinct from the three-domain Cry toxins, as they have an elongated and predominately j-sheet-based structure. However, similar to the three-domain toxins, the MTX-like proteins are thought to form pores in the membranes of target cells (Adang et al. (2014) supra). Unlike the three-domain Cry proteins, the MTX-like proteins are much smaller in length, ranging from 267 amino acids (Cry23) to 340 amino acids (Cry15A.

The protein family of MTX-like toxins is a relatively small class compared to the three-domain Cry family (Crickmore et al. (2014) supra; Adang et al. (2014) supra). The members of the MTX-like toxin family include Cry15, Cry23, Cry33, Cry38, Cry45, Cry46, Cry51, Cry60A, Cry60B, and Cry64. This family exhibits a range of insecticidal activity, including activity against insect pests of the Lepidopteran and Coleopteran orders. Some members of this family may form binary partnerships with other proteins, which may or may not be required for insecticidal activity.

The classification of the Mtx-like proteins has been revised to be in the Mpp (Mtx2-like pesticidal proteins) class of beta pore-forming pesticidal proteins from the ETX/MTX2 family. See, Crickmore, et al., 2020*, J. Invert. Path., July* 9:107438, doi: 10.1016/j.jip.2020.107438, PMID: 32652083.

Cry15 is a 34 kDA protein that was identified in *Bacillus thuringiensis* serovar thompsoni HD542; it occurs naturally in a crystal together with an unrelated protein of approximately 40 kDa. The gene encoding Cry15 and its partner protein are arranged together in an operon. Cry15 alone has been shown to have activity against lepidopteran insect pests including *Manduca sexta, Cydia pomonella*, and *Pieris rapae*, with the presence of the 40 kDA protein having been shown to increase activity of Cry15 only against *C. pomonella* (Brown K. and Whiteley H. (1992) *J. Bacteriol.* 174:549-557; Naimov et al. (2008) *Appl. Environ. Microbiol.* 74:7145-7151). Further studies are needed to elucidate the function of the partner protein of Cry15. Similarly, Cry23 is a 29 kDA protein that has been shown to have activity against the coleopteran pests *Tribolium castaneum* and *Popillia japonica* together with its partner protein Cry37 (Donovan et al. (2000) U.S. Pat. No. 6,063,756).

New members of the MTX-like family are continuing to be identified. An ETX_MTX toxin gene was recently identified in the genome of *Bacillus thuringiensis* serovar tolworthi strain Na205-3. This strain was found to be toxic against the lepidpoteran pest *Helicoverpa armigera*, and it also contained homologs of Cry1, Cry11, Vip1, Vip2, and Vip3 (Palma et al. (2014) *Genome Announc.* 2(2): e00187-14. Published online Mar. 13, 2014 at doi: 10.1128/genomeA.00187-14; PMCID: PMC3953196). Because the MTX-like proteins have a unique domain structure relative to the three-domain Cry proteins, they are believed to possess a unique mode of action, thereby making them a valuable tool in insect control and the fight against insect resistance.

Bacterial cells produce large numbers of toxins with diverse specificity against host and non-host organisms. Large families of binary toxins have been identified in numerous bacterial families, including toxins that have activity against insect pests. (Poopathi and Abidha (2010) *J. Physiol. Path.* 1(3): 22-38). *Lysinibacillus sphaericus* (Ls), formerly *Bacillus sphaericus*, (Ahmed et al. (2007) *Int. J. Syst. Evol. Microbiol.* 57:1117-1125) is well-known as an insect biocontrol strain. Ls produces several insecticidal proteins, including the highly potent binary complex BinA/BinB. This binary complex forms a parasporal crystal in Ls cells and has strong and specific activity against dipteran insects, specifically mosquitos. In some areas, insect resistance to existing Ls mosquitocidal strains has been reported. The discovery of new binary toxins with different target specificity or the ability to overcome insect resistance is of significant interest.

The Ls binary insecticidal protein complex contains two major polypeptides, a 42 kDa polypeptide and a 51 kDa polypeptide, designated BinA and BinB, respectively (Ahmed et al. (2007) supra). The two polypeptides act synergistically to confer toxicity to their targets. Mode of action involves binding of the proteins to receptors in the larval midgut. In some cases, the proteins are modified by protease digestion in the larval gut to produce activated forms. The BinB component is thought to be involved in binding, while the BinA component confers toxicity (Nielsen-LeRoux et al. (2001) *Appl. Environ. Microbiol.* 67(11):5049-5054). When cloned and expressed separately, the BinA component is toxic to mosquito larvae, while the BinB component is not. However, co-administration of the proteins markedly increases toxicity (Nielsen-LeRoux et al. (2001) supra).

A small number of Bin protein homologs have been described from bacterial sources. Priest et al. (1997) *Appl. Environ. Microbiol.* 63(4):1195-1198 describe a hybridization effort to identify new Ls strains, although most of the genes they identified encoded proteins identical to the known BinA/BinB proteins. The BinA protein contains a defined conserved domain known as the Toxin 10 superfamily domain. This toxin domain was originally defined by its presence in BinA and BinB. The two proteins both have the domain, although the sequence similarity between BinA and BinB is limited in this region (<40%). The Cry49Aa protein, which also has insecticidal activity, also has this domain (described below).

The Cry48Aa/Cry49Aa binary toxin of Ls has the ability to kill *Culex quinquefasciatus* mosquito larvae. These proteins are in a protein structural class that has some similarity to the Cry protein complex of *Bacillus thuringiensis* (Bt), a well-known insecticidal protein family. The Cry34/Cry35 binary toxin of Bt is also known to kill insects, including Western corn rootworm, a significant pest of corn. Cry34, of which several variants have been identified, is a small (14 kDa) polypeptide, while Cry35 (also encoded by several variants) is a 44 kDa polypeptide. These proteins have some sequence homology with the BinA/BinB protein group and are thought to be evolutionarily related (Ellis et al. (2002) *Appl. Environ. Microbiol.* 68(3):1137-1145).

The classification of Cry34 has been revised to be in the Gpp class of aegerolysin like pesticidal proteins, such as Gpp34Aa. See, Crickmore, et al., 2020, *J. Invert. Path.*, July 9:107438, doi: 10.1016/j.jip.2020.107438, PMID: 32652083.

Phosphoinositide phospholipase C proteins (PI-PLC; also phosphotidylinositol phospholipase C) are members of the broader group of phospholipase C proteins. Many of these proteins play important roles in signal transduction as part of normal cell physiology. Several important bacterial toxins also contain domains with similarity to these proteins (Titball, R. W. (1993) *Microbiological Reviews.* 57(2):347-366). Importantly, these proteins are implicated in signal amplification during intoxication of insect cells by Bt Cry proteins (Valaitis, A. P. (2008) *Insect Biochemistry and Molecular Biology.* 38: 611-618).

The PI-PLC toxin class occurs in *Bacillus* isolates, commonly seen in co-occurrence with homologs to other described toxin classes, such as Binary Toxins. This class of sequences has homology to phosphatidylinositol phosphodiesterases (also referred to as phosphatidylinositol-specific phospholipase C—PI-PLC). The crystal structure and its active site were solved for *B. cereus* PI-PLC by Heinz et al (Heinz, et. al., (1995) *The EMBO Journal.* 14(16): 3855-3863). The roles of the *B. cereus* PI-PLC active site amino acid residues in catalysis and substrate binding were investigated by Gässler et al using site-directed mutagenesis, kinetics, and crystal structure analysis (Gässler, et. al., (1997) *Biochemistry.* 36(42):12802-13).

These PI-PLC toxin proteins contain a PLC-like phosphodiesterase, TIM beta/alpha-barrel domain (IPR017946) and/or a Phospholipase C, phosphatidylinositol-specific, X domain (IPR000909) (also referred to as the PI-PLC X-box domain). We have also seen proteins with these domains in combination with other typical *Bacillus* protein toxin domains. This list includes most commonly a lectin domain (IPR000772), a sugar-binding domain that can be present in one or more copies and is thought to bind cell membranes, as well as the Insecticidal crystal toxin (IPR008872) (also referred to as Toxin10 or P42), which is the defining domain of the Binary Toxin.

Previously, toxins of this PI-PLC class were defined in U.S. Pat. No. 8,318,900 B2 SEQ ID NOs: 30 (DNA) and 79 (amino acid), in U.S. Patent Publication No. 20110263488A1 SEQ ID NOs: 8 (DNA) and 9 (amino acid), and in U.S. Pat. No. 8,461,421B2 SEQ ID NOs: 3 (DNA) and 63 (amino acid).

Provided herein are pesticidal proteins from these classes of toxins. The pesticidal proteins are classified by their structure, homology to known toxins and/or their pesticidal specificity.

ii. Variants and Fragments of Pesticidal Proteins and Polynucleotides Encoding the Same Pesticidal proteins or polypeptides of the invention include those set forth in SEQ ID NOs: 2, 4, 6, 8, 10, 12, 14, 16, 18, 20, 22, 24, 26, 28, 30, 32, 34, 36, 38, and/or 40, and fragments and variants thereof. By "pesticidal toxin" or "pesticidal protein" or "pesticidal polypeptide" is intended a toxin or protein or polypeptide that has activity against one or more pests, including, insects, fungi, nematodes, and the like such that the pest is killed or controlled.

The term "isolated" or "purified" encompasses a polypeptide or protein, or biologically active portion thereof, polynucleotide or nucleic acid molecule, or other entity or substance, that is substantially or essentially free from components that normally accompany or interact with the polypeptide or polynucleotide as found in its naturally occurring environment. Isolated polypeptides or polynucleotides may be separated from at least about 10%, about 20%, about 30%, about 40%, about 50%, about 60%, about 70%, about 80%, about 90%, or more of the other components with which they were initially associated. Thus, an isolated or purified polypeptide or protein is substantially free of other cellular material, or culture medium when produced by recombinant techniques, or substantially free of chemical precursors or other chemicals when chemically synthesized. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

The term "fragment" refers to a portion of a polypeptide sequence of the invention. "Fragments" or "biologically active portions" include polypeptides comprising a sufficient number of contiguous amino acid residues to retain the biological activity, i.e., have pesticidal activity. Fragments of the pesticidal proteins include those that are shorter than the full-length sequences, either due to the use of an alternate downstream start site, or due to processing that produces a shorter protein having pesticidal activity. Processing may occur in the organism the protein is expressed in, or in the pest after ingestion of the protein. Examples of fragments of the proteins can be found in Table 1. A biologically active portion of a pesticidal protein can be a polypeptide that is, for example, 10, 20, 25, 30, 50, 40, 50, 60, 70, 75, 80, 90, 100, 110, 120, 125, 130, 140, 150, 160, 170, 175, 180, 190, 200, 210, 220, 225, 230, 240, 250, 260 or more contiguous amino acids in length of any one of SEQ ID NOs: 2, 4, 6, 8, 10, 12, 14, 16, 18, 20, 22, 24, 26, 28, 30, 32, 34, 36, 38, and/or 40. Such biologically active portions can be prepared by recombinant techniques and evaluated for pesticidal activity. As used here, a fragment comprises at least 8 contiguous amino acids of SEQ ID NOs: 2, 4, 6, 8, 10, 12, 14, 16, 18, 20, 22, 24, 26, 28, 30, 32, 34, 36, 38, and/or 40.

Bacterial genes, including those encoding the pesticidal proteins disclosed herein, quite often possess multiple methionine initiation codons in proximity to the start of the open reading frame. Often, translation initiation at one or more of these start codons will lead to generation of a functional protein. These start codons can include ATG codons. However, bacteria such as Bacillus sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined apriori which of these codons are used naturally in the bacterium. Thus, it is understood that use of one of the alternate methionine codons may also lead to generation of pesticidal proteins. These pesticidal proteins are encompassed in the present invention and may be used in the methods disclosed herein. It will be understood that, when expressed in plants, it will be necessary to alter the alternate start codon to ATG for proper translation.

In various embodiments the pesticidal proteins provided herein include amino acid sequences deduced from the full-length nucleotide sequences and amino acid sequences that are shorter than the full-length sequences due to the use of an alternate downstream start site. Thus, the nucleotide sequence of the invention and/or vectors, host cells, and plants comprising the nucleotide sequence of the invention (and methods of making and using the nucleotide sequence of the invention) may comprise a nucleotide sequence encoding an alternate start site.

It is recognized that modifications may be made to the pesticidal polypeptides provided herein creating variant proteins. Changes designed by man may be introduced through the application of site-directed mutagenesis techniques. Alternatively, native, as yet-unknown or as yet unidentified polynucleotides and/or polypeptides structurally and/or functionally-related to the sequences disclosed herein may also be identified that fall within the scope of the present invention. Conservative amino acid substitutions may be made in nonconserved regions that do not alter the function of the pesticidal proteins. Alternatively, modifications may be made that improve the activity of the toxin. Modification of Cry toxins by domain III swapping has resulted in some cases in hybrid toxins with improved toxicities against certain insect species. Thus, domain III swapping could be an effective strategy to improve toxicity of Cry toxins or to create novel hybrid toxins with toxicity against pests that show no susceptibility to the parental Cry toxins. Site-directed mutagenesis of domain II loop sequences may result in new toxins with increased insecticidal activity. Domain II loop regions are key binding regions of initial Cry toxins that are suitable targets for the mutagenesis and selection of Cry toxins with improved insecticidal properties. Domain I of the Cry toxin may be modified to introduce protease cleavage sites to improve activity against certain pests. Strategies for shuffling the three different domains among large numbers of cry genes and high through output bioassay screening methods may provide novel Cry toxins with improved or novel toxicities.

As indicated, fragments and variants of the polypeptides disclosed herein will retain pesticidal activity. Pesticidal activity comprises the ability of the composition to achieve an observable effect diminishing the occurrence or an activity of the target pest, including for example, bringing about death of at least one pest, or a noticeable reduction in pest growth, feeding, or normal physiological development. Such decreases in numbers, pest growth, feeding or normal development can comprise any statistically significant decrease, including, for example a decrease of about 5%, 10%, 15%, 20%, 25%, 30%, 35%, 40%, 45%, 50%, 55%, 60%, 65%, 70%, 75%, 85%, 90%, 95% or greater. The pesticidal activity against one or more of the various pests provided herein, including, for example, pesticidal activity against Coleoptera, Diptera, Hymenoptera, Lepidoptera, Mallophaga, Homoptera, Hemiptera, Orthroptera, Nematodes, Thysanoptera, Dermaptera, Isoptera, Anoplura, Siphonaptera, Trichoptera, etc., or any other pest described herein. It is recognized that the pesticidal activity may be different or improved relative to the activity of the native protein, or it may be unchanged, so long as pesticidal activity is retained. Methods for measuring pesticidal activity are provided elsewhere herein. See also, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

By "variants" is intended polypeptides having an amino acid sequence that is at least about 70%, about 75%, about 80%, about 85%, about 86%, about 87%, about 88%, about 89%, about 90%, about 91%, about 92%, about 93%, about 94%, about 95%, about 96%, about 97%, about 98% or about 99% identical to the amino acid sequence of any of SEQ ID NOs: 2, 4, 6, 8, 10, 12, 14, 16, 18, 20, 22, 24, 26, 28, 30, 32, 34, 36, 38, and/or 40, and retain pesticidal activity. Note, Table 1 provides non-limiting examples of variant polypeptides (and polynucleotide encoding the same) for each of SEQ ID NOs: 2, 4, 6, 8, 10, 12, 14, 16, 18, 20, 22, 24, 26, 28, 30, 32, 34, 36, 38, and/or 40. A biologically active variant of a pesticidal polypeptide of the invention may differ by as few as about 1-15 amino acid residues, as few as about 1-10, such as about 6-10, as few as 5, as few as 4, as few as 3, as few as 2, or as few as 1 amino acid residue. In specific embodiments, the polypeptides can comprise an N-terminal or a C-terminal truncation, which can comprise at least a deletion of 10, 15, 20, 25, 30, 35, 40, 45, 50 amino acids or more from either the N or C terminal of the polypeptide.

Table 2 provides protein domains found in SEQ ID NOs: 2, 4, 6, 8, 10, 12, 14, 16, 18, 20, 22, 24, 26, 28, 30, 32, 34, 36, 38, and/or 40 based on PFAM data. Both the domain description and the positions within a given SEQ ID NO are provided in Table 2. In specific embodiments, the active variant comprising any one of SEQ ID NOs: 2, 4, 6, 8, 10, 12, 14, 16, 18, 20, 22, 24, 26, 28, 30, 32, 34, 36, 38, and/or 40 can comprise at least 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to any one of SEQ ID NOs: 2, 4, 6, 8, 10, 12, 14, 16, 18, 20, 22, 24, 26, 28, 30, 32, 34, 36, 38, and/or 40 and further comprises at least one of the conserved domains set forth in Table 2. For example, in one embodiment, the active variant will comprise at least 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO: 4, and further comprises the native amino acids at positions 41-408.

TABLE 2

Summary of PFAM domains in each of SEQ ID NOs: 2, 4, 6, 8, 10, 12, 14, 16, 18, 20, 22, 24, 26, 28, 30, 32, 34, 36, 38, and 40

| APG ID | Seq ID NO | Modification Type | PFAM domain | Domain Description | Domain Positions Start | Stop |
|---|---|---|---|---|---|---|
| APG06396.0 | 2 | | None | | | |
| APG03083.0 | 4 | | PF01117.20 | Aerolysin | 41 | 408 |
| APG03083.1 | 6 | Start Site | PF01117.20 | Aerolysin | 19 | 386 |
| APG05736.0 | 8 | | PF01117 | Aerolysin | 137 | 280 |
| APG05736.1 | 10 | Start Site | PF01117 | Aerolysin | 134 | 277 |
| APG05736.2 | 12 | Removed signal peptide | PF01117 | Aerolysin | 109 | 252 |
| APG02668.0 | 14 | | PF01117 | Aerolysin | 136 | 281 |
| APG02668.1 | 16 | Removed signal peptide | PF01117 | Aerolysin | 111 | 256 |
| APG06377.0 | 18 | | PF01117 | Aerolysin | 15 | 75 |
| | | | PF01117 | Aerolysin | 136 | 281 |
| APG06377.1 | 20 | Removed signal peptide | PF01117 | Aerolysin | 116 | 261 |
| APG08037.0 | 22 | | PF01117 | Aerolysin | 136 | 280 |
| APG08037.1 | 24 | Removed signal peptide | PF01117 | Aerolysin | 111 | 255 |
| APG03548.0 | 26 | | PF03318.13 | ETX_MTX | 118 | 315 |
| APG03548.1 | 28 | Removed signal peptide | PF03318.13 | ETX_MTX | 79 | 277 |
| APG03548.2 | 30 | Start site | PF03318.13 | ETX_MTX | 115 | 312 |
| APG04564.0 | 32 | | PF03318.13 | ETX_MTX | 132 | 353 |
| APG04564.1 | 34 | Start site | PF03318.13 | ETX_MTX | 129 | 350 |
| APG04564.2 | 36 | Removed signal peptide | PF03318.13 | ETX_MTX | 95 | 315 |
| APG03088.0 | 38 | | PF03318.13 | ETX_MTX | 145 | 349 |
| APG03088.1 | 40 | Removed signal peptide | PF03318.13 | ETX_MTX | 133 | 320 |

Nucleic acid molecules, including recombinant or synthetic nucleic acid molecules encoding the pesticidal polypeptides disclosed herein are also provided and include those set forth in SEQ ID NOs: 1, 3, 5, 7, 9, 11, 13, 15, 17, 19, 21, 23, 25, 27, 29, 31, 33, 35, 37, and/or 39. Of particular interest are nucleic acid sequences that have been designed for expression in a plant or a microbe of interest. That is, the nucleic acid sequence can be optimized for increased expression in a host plant or in a host microbe of interest. A pesticidal protein of the invention can be back-translated to produce a nucleic acid comprising codons optimized for expression in a particular host, for example, a crop plant. In another embodiment, the polynucleotides encoding the polypeptides provided herein may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference. Expression of such a coding sequence by the transformed plant (e.g., dicot or monocot) will result in the production of a pesticidal polypeptide and confer increased resistance in the plant to a pest. Recombinant and synthetic nucleic acid molecules encoding the pesticidal proteins of the invention do not include the naturally occurring bacterial sequence encoding the protein.

A "recombinant polynucleotide" or "recombinant nucleic acid" or "recombinant nucleic acid molecule" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or a variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides include chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide or nucleic acid" comprises at least one of a combination of two or more chemically linked amino acid segments which are not found directly joined in nature. A "recombinant polypeptide" or "recombinant protein" is a polypeptide or protein encoded by a recombinant polynucleotide.

Fragments of a polynucleotide (RNA or DNA) may encode protein fragments that retain activity. In specific embodiments, a fragment of a recombinant polynucleotide or a recombinant polynucleotide construct comprises at least one junction of the two or more chemically linked or operably linked nucleic acid segments which are not found directly joined in nature. A fragment of a polynucleotide that encodes a biologically active portion of a polypeptide that retains pesticidal activity will encode at least 25, 30, 40, 50, 60, 70, 75, 80, 90, 100, 110, 120, 125, 130, 140, 150, 160, 170, 175, 180, contiguous amino acids, or up to the total number of amino acids present in a full-length polypeptide as set forth in SEQ ID NOs: 2, 4, 6, 8, 10, 12, 14, 16, 18, 20, 22, 24, 26, 28, 30, 32, 34, 36, 38, and/or 40. In some embodiments, a fragment of a polynucleotide comprises at least 25, 30, 40, 50, 60, 70, 75, 80, 90, 100, 110, 120, 125, 130, 140, 150, 160, 170, 175, 180, 190, 200, 210, 220, 225, 230, 240, 250, 260, 270, 275, 280, 290, 300, 310, 320, 325, 330, 340, 350, 360, 370, 375, 380, 390, 400, contiguous nucleotides, or up the total number of nucleotides present in a full-length nucleotide sequence set forth in SEQ ID NOs: 1, 3, 5, 7, 9, 11, 13, 15, 17, 19, 21, 23, 25, 27, 29, 31, 33, 35, 37, and/or 39. In specific embodiments, such polypeptide fragments are active fragment, and in still other embodiments, the polypeptide fragment comprises a recombinant polypeptide fragment. As used herein, a fragment of a recombinant polypeptide comprises at least one of a combination of two or more chemically linked amino acid segments which are not found directly joined in nature.

By "variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively.

Variants of a particular polynucleotide of the invention, including those polynucleotides set forth in SEQ ID NOs: 1, 3, 5, 7, 9, 11, 13, 15, 17, 19, 21, 23, 25, 27, 29, 31, 33, 35, 37, and/or 39 (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NOs: 2, 4, 6, 8, 10, 12, 14, 16, 18, 20, 22, 24, 26, 28, 30, 32, 34, 36, 38, and/or 40 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 70%, 75%, 80%, 85%, 86%, 87%, 88%, 89%, 90%, 91%, 92%, 93%, 94%, 95%, 96%, 97%, 98%, 99% or more sequence identity to SEQ ID NOs: 2, 4, 6, 8, 10, 12, 14, 16, 18, 20, 22, 24, 26, 28, 30, 32, 34, 36, 38, and/or 40. In other embodiments, the variant of the polynucleotide provided herein differs from the native sequence by at least 1, 2, 3, 4, 5, 6, 7, 8, 9, 10 or more nucleotides.

Variant polynucleotides and proteins also encompass sequences and proteins derived from a mutagenic and recombinogenic procedure such as DNA shuffling. With such a procedure, one or more different pesticidal protein disclosed herein (SEQ ID NOs: 2, 4, 6, 8, 10, 12, 14, 16, 18, 20, 22, 24, 26, 28, 30, 32, 34, 36, 38, and/or 40) is manipulated to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the pesticidal sequences provided herein and other known pesticidal genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458. A "shuffled" nucleic acid is a nucleic acid produced by a shuffling procedure such as any shuffling procedure set forth herein. Shuffled nucleic acids are produced by recombining (physically or virtually) two or more nucleic acids (or character strings), for example in an artificial, and optionally recursive, fashion. Generally, one or more screening steps are used in shuffling processes to identify nucleic acids of interest; this screening step can be performed before or after any recombination step. In some (but not all) shuffling embodiments, it is desirable to perform multiple rounds of recombination prior to selection to increase the diversity of the pool to be screened. The overall process of recombination and selection are optionally repeated recursively. Depending on context, shuffling can refer to an overall process of recombination and selection, or, alternately, can simply refer to the recombinational portions of the overall process.

In one embodiment, a method of obtaining a polynucleotide that encodes an improved polypeptide comprising pesticidal activity is provided, wherein the improved polypeptide has at least one improved property over any one of SEQ ID NOs: 2, 4, 6, 8, 10, 12, 14, 16, 18, 20, 22, 24, 26, 28, 30, 32, 34, 36, 38, and/or 40. Such methods can comprise (a) recombining a plurality of parental polynucleotides to produce a library of recombinant polynucleotides encoding recombinant pesticidal polypeptides; (b) screening the library to identify a recombinant polynucleotide that encodes an improved recombinant pesticidal polypeptide that has an enhanced property improved over the parental polynucleotide; (c) recovering the recombinant polynucleotide that encodes the improved recombinant pesticidal polypeptide identified in (b); and, (d) repeating steps (a), (b) and (c) using the recombinant polynucleotide recovered in step (c) as one of the plurality of parental polynucleotides in repeated step (a).

iii. Sequence Comparisons

As used herein, the term "identity" or "percent identity" when used with respect to a particular pair of aligned amino acid sequences or aligned nucleotide sequences, refers to the percent amino acid sequence identity or percent nucleotide sequence identity that is obtained by counting the number of identical matches in the alignment and dividing such number of identical matches by the length of the aligned sequences. As used herein, the term "similarity" or "percent similarity" when used with respect to a particular pair of aligned amino acid sequences or aligned nucleotide sequences, refers to the sum of the scores that are obtained from a scoring matrix for each amino acid pair or each nucleotide pair in the alignment divided by the length of the aligned sequences.

Unless otherwise stated, identity and similarity will be calculated by the Needleman-Wunsch global alignment and scoring algorithms (Needleman and Wunsch (1970) *J. Mol. Biol.* 48(3):443-453) as implemented by the "needle" program, distributed as part of the EMBOSS software package (Rice, P. Longden, I. and Bleasby, A., EMBOSS: The European Molecular Biology Open Software Suite, 2000, *Trends in Genetics* 16, (6) pp 276-277, versions 6.3.1 available from EMBnet at embnet.org/resource/emboss and emboss.sourceforge.net, among other sources) using default gap penalties and scoring matrices (EBLOSUM62 for protein and EDNAFULL for DNA). Equivalent programs may also be used. By "equivalent program" is intended any sequence comparison program that, for any two sequences in question, generates an alignment having identical nucleotide residue matches and an identical percent sequence identity when compared to the corresponding alignment generated by needle from EMBOSS version 6.3.1.

Additional mathematical algorithms are known in the art and can be utilized for the comparison of two sequences. See, for example, the algorithm of Karlin and Altschul (1990) Proc. Natl. Acad. Sci. USA 87:2264, modified as in Karlin and Altschul (1993) Proc. Natl. Acad. Sci. USA 90:5873-5877. Such an algorithm is incorporated into the BLAST programs of Altschul et al. (1990) J. Mol. Biol. 215:403. BLAST nucleotide searches can be performed with the BLASTN program (nucleotide query searched against nucleotide sequences) to obtain nucleotide sequences homologous to pesticidal-like nucleic acid molecules of the invention, or with the BLASTX program (translated nucleotide query searched against protein sequences) to obtain protein sequences homologous to pesticidal nucleic acid molecules of the invention. BLAST protein searches can be performed with the BLASTP program (protein query searched against protein sequences) to obtain amino acid sequences homologous to pesticidal protein molecules of the invention, or with the TBLASTN program (protein query searched against translated nucleotide sequences) to obtain nucleotide sequences homologous to pesticidal protein molecules of the invention. To obtain gapped alignments for comparison purposes, Gapped BLAST (in BLAST 2.0) can be utilized as described in Altschul et al. (1997) *Nucleic*

Acids Res. 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins." In "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Natl. Acad. Sci. USA 89:10915-10919. The BLOSUM62 matrix is often used as a default scoring substitution matrix in sequence alignment protocols. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al. (1997) *Nucleic Acids Res.* 25:3389-3402, and made available to the public at the National Center for Biotechnology Information Website (www.ncbi.nlm.nih.gov). Optimal alignments, including multiple alignments, can be prepared using, e.g., PSI-BLAST, available through www.ncbi.nlm.nih.gov and described by Altschul et al. (1997) *Nucleic Acids Res.* 25:3389-3402.

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. For example, in SEQ ID NO: 2 position 1 is M, position 2 is H, position 3 is S, etc. When a test sequence is optimally aligned with SEQ ID NO: 2, a residue in the test sequence that aligns with the S at position 3 is said to "correspond to position 3" of SEQ ID NO: 2. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

iv. Antibodies

Antibodies to the polypeptides of the present invention, or to variants or fragments thereof, are also encompassed. Methods for producing antibodies are well known in the art (see, for example, Harlow and Lane (1988) Antibodies: A Laboratory Manual, Cold Spring Harbor Laboratory, Cold Spring Harbor, N.Y.; and U.S. Pat. No. 4,196,265). These antibodies can be used in kits for the detection and isolation of toxin polypeptides. Thus, this disclosure provides kits comprising antibodies that specifically bind to the polypeptides described herein, including, for example, polypeptides having the sequence of SEQ ID NOs: 2, 4, 6, 8, 10, 12, 14, 16, 18, 20, 22, 24, 26, 28, 30, 32, 34, 36, 38, and/or 40.

II. Pests

The compositions and methods provided herein are useful against a variety of pests. "Pests" includes but is not limited to, insects, fungi, bacteria, nematodes, acarids, protozoan pathogens, animal-parasitic liver flukes, and the like. Pests of particular interest are insect pests, particularly insect pests that cause significant damage to agricultural plants. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, or nematodes. In non-limiting embodiments, the insect pest comprises Western corn rootworm, *Diabrotica virgifera virgifera*; Fall armyworm, *Spodoptera frugiperda*; Colorado potato beetle, *Leptinotarsa decemlineata*; Corn earworm, *Helicoverpa zea* (in North America same species attacks cotton and called cotton bollworm); European corn borer, *Ostrinia nubilalis*; Black cutworm, *Agrotis ipsilon*; Diamondback moth, *Plutella xylostella*; Velvetbean caterpillar, *Anticarsia gemmatalis*; Southwestern corn borer, *Diatraea grandiosella*; Cotton bollworm, *Helicoverpa armigera* (found other than USA in rest of the world); Southern green stink bug, *Nezara viridula*; Green stink bug, *Chinavia halaris*; Brown marmorated stink bug, *Halyomorpha halys*; and Brown stink bug, *Euschistus servus*, *Euschistus heros* (Neotropical brown stink bug OR soy stink bug); *Piezodorus guildinii* (red-banded stink bug); *Dichelops melacanthus* (no common name) and/or *Dichelops furcatus* (no common name); an aphid, such as a soybean aphid. In other embodiments, the pest comprises a nematode including, but not limited to, *Meloidogyne hapla* (Northern root-knot nematode); *Meloidogyne enterolobii*, *Meloidogyne arenaria* (peanut root-knot nematode); and *Meloidogyne javanica*.

The term "insect pests" as used herein refers to insects and other similar pests such as, for example, those of the order Acari including, but not limited to, mites and ticks. Insect pests of the present invention include, but are not limited to, insects of the order Lepidoptera, e.g. *Achoroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis, Archips sp., Argyrotaenia sp., Athetis mindara, Bombyx mori, Bucculatrix thurberiella, Cadra cautella, Choristoneura sp., Cochylls hospes, Colias eurytheme, Corcyra cephalonica, Cydia latiferreanus, Cydia pomonella, Datana integerrima, Dendrolimus sibericus, Desmiafeneralis, Diaphania hyalinata, Diaphania nitidalis, Diatraea grandiosella, Diatraea saccharalis, Ennomos subsignaria, Eoreuma loftini, Esphestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea, Heliothis virescens, Hemileuca oliviae,*

*Homoeosoma electellum, Hyphantia cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrisalis, Malacosoma* sp., *Mamestra brassicae, Mamestra configurata, Manduca quinquemaculata, Manduca sexta, Maruca testulalis, Melanchra picta, Operophtera brumata, Orgyia* sp., *Ostrinia nubilalis, Paleacrita vernata, Papilio cresphontes, Pectinophora gossypiella, Phryganidia calfornica, Phyllonorycter blancardella, Pieris napi, Pieris rapae, Plathypena scabra, Platynotaflouendana, Platynota stultana, Platyptilia carduidactyla, Plodia interpunctella, Plutella xylostella, Pontia protodice, Pseudaletia unipuncta, Pseudoplasia includens, Sabulodes aegrotata, Schizura concinna, Sitotroga cerealella, Spilonta ocellana, Spodoptera* sp., *Thaurnstopoea pityocampa, Tinsola bisselliella, Trichoplusia hi, Udea rubigalis, Xylomyges curiails,* and *Yponomeuta padella.*

Insect pests also include insects selected from the orders Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, Coleoptera. Insect pests of the invention for the major crops include, but are not limited to: Maize: *Ostrinia nubilalis*, European corn borer; *Agrotis ipsilon*, black cutworm; *Helicoverpa zeae*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; western corn rootworm, e.g., *Diabrotica virgifera virgifera*; northern corn rootworm, e.g., *Diabrotica longicornis barberi*; southern corn rootworm, e.g., *Diabrotica undecimpunctata howardi; Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Euschistus heros* (Neotropical brown stink bug OR soy stink bug); *Piezodorus guildinii* (red-banded stink bug); *Dichelops melacanthus* (no common name); *Dichelops furcatus* (no common name); *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blotch leafminer; *Anaphothrips obscrurus*, grass thrips; *Solenopsis milesta*, thief ant; *Tetranychus urticae*, two spotted spider mite; Sorghum: *Chilo partellus*, sorghum borer; *Spodoptera frugiperda*, fall armyworm; *Helicoverpa zea*, corn earworm; *Elasmopalpus lignosellus*, leser cornstalk borer; *Feltia subterranea*, granulate cutworm; *Phyllophaga crinita*, white grub; *Eleodes, Conoderus,* and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; chinch bug, e.g., *Blissus leucopterus leucopterus; Contarinia sorghicola*, sorghum midge; *Tetranychus cinnabarinus*, carmine spider mite; *Tetranychus urticae*, two-spotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, pale western cutworm; *Elasmopalpus lignosellus*, lesser cornstalk borer; *Oulema melanopus*, cereal leaf beetle; *Hypera punctata*, clover leaf weevil; southern corn rootworm, e.g., *Diabrotica undecimpunctata howardi;* Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Cylindrocupturus adspersus*, sunflower stem weevil; *Smicronyx fulus*, red sunflower seed weevil; *Smicronyx sordidus*, gray sunflower seed weevil; *Suleima helianthana*, sunflower bud moth; *Homoeosoma electellum*, sunflower moth; *Zygogramma exclamationis*, sunflower beetle; *Bothyrus gibbosus*, carrot beetle; *Neolasioptera murtfeldtiana*, sunflower seed midge; Cotton: *Heliothis virescens*, tobacco budworm; *Helicoverpa zea*, cotton bollworm; *Spodoptera exigua*, beet armyworm; *Pectinophora gossypiella*, pink bollworm; boll weevil, e.g., *Anthonomus grandis; Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, two-spotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhoper; chinch bug, e.g., *Blissus leucopterus leucopterus; Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, tobacco budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean *thrips; Thrips tabaci*, onion thrips; *Tetranychus turkestani*, strawberry spider mite; *Tetranychus urticae*, two-spotted spider mite; Barley: *Ostrinia nubilalis*, European corn borer; *Agrotis ipsilon*, black cutworm; *Schizaphis graminum*, greenbug; chinch bug, e.g., *Blissus leucopterus leucopterus; Acrosternum hilare*, green stink bug; *Euschistus servus*, brown stink bug; *Jylemya platura*, seedcorn maggot; *Mayetiola destructor*, Hessian fly; *Petrobia latens*, brown wheat mite; Oil Seed Rape: *Vrevicoryne brassicae*, cabbage aphid; *Phyllotreta cruciferae*, crucifer flea beetle; *Phyllotreta striolata*, striped flea beetle; *Phyllotreta nemorum*, striped turnip flea beetle; *Meligethes aeneus*, rapeseed beetle; and the pollen beetles *Meligethes rufimanus, Meligethes nigrescens, Meligethes canadianus,* and *Meligethes viridescens;* Potato: *Leptinotarsa decemlineata*, Colorado potato beetle.

The methods and compositions provided herein may be effective against Hemiptera such as *Lygus hesperus, Lygus lineolaris, Lygus pratensis, Lygus rugulipennis Popp, Lygus pabulinus, Calocoris norvegicus, Orthops compestris, Plesiocoris rugicollis, Cyrtopeltis modestus, Cyrtopeltis notatus, Spanagonicus albofasciatus, Diaphnocoris chlorinonis, Labopidicola allii, Pseudatomoscelis seriatus, Adelphocoris rapidus, Poecilocapsus lineatus, Blissus leucopterus, Nysius ericae, Nysius raphanus, Euschistus servus, Nezara*

*viridula*, *Eurygaster*, Coreidae, Pyrrhocoridae, Tinidae, Blostomatidae, Reduviidae, and Cimicidae. Pests of interest also include Araecerusfasciculatus, coffee bean weevil; *Acanthoscelides obtectus*, bean weevil; *Bruchus rufimanus*, broadbean weevil; *Bruchus pisorum*, pea weevil; *Zabrotes subfasciatus*, Mexican bean weevil; *Diabrotica balteata*, banded cucumber beetle; *Cerotoma trifurcata*, bean leaf beetle; *Diabrotica virgifera*, Mexican corn rootworm; *Epitrix cucumeris*, potato flea beetle; *Chaetocnema confinis*, sweet potato flea beetle; *Hypera postica*, alfalfa weevil; *Anthonomus quadrigibbus*, apple curculio; *Sternechus paludatus*, bean stalk weevil; *Hypera brunnipennis*, Egyptian alfalfa weevil; *Sitophilus granaries*, granary weevil; *Craponius inaequalis*, grape curculio; *Sitophilus zeamais*, maize weevil; *Conotrachelus nenuphar*, plum curculio; *Euscepes postfaciatus*, West Indian sweet potato weevil; *Maladera castanea*, Asiatic garden beetle; *Rhizotrogus majalis*, European chafer; *Macrodactylus subspinosus*, rose chafer; *Tribolium confusum*, confused flour beetle; *Tenebrio obscurus*, dark mealworm; *Tribolium castaneum*, red flour beetle; *Tenebrio molitor*, yellow mealworm.

In some embodiments, the presently disclosed pesticidal proteins have pesticidal activity against insect pests that are resistant to one or more strains of *Bacillus thuringiensis* or one or more toxin proteins produced by one or more strains of *Bacillus thuringiensis*. As used herein, the term "resistant" as it relates to an insect pest refers to an insect pest that does not die in the presence of a toxin or does not exhibit reduced growth in the presence of a toxin when compared to the growth of the insect pest in the absence of the toxin. In certain embodiments, the presently disclosed pesticidal proteins have pesticidal activity against insect pests that are resistant to any one of Cry34/Cry35, Cry3Bb, Cry2Ab2, and Vip3A. In particular embodiments, the presently disclosed pesticidal proteins have pesticidal activity against Coleoptera insect pests (including, but not limited to, Western corn rootworm) that are resistant to one or more of Cry34/Cry35 and Cry3Bb. In some embodiments, the presently disclosed pesticidal proteins have pesticidal activity against Lepidopteran insect pests (including, but not limited to, Fall armyworm) that are resistant to one or more of Cry2Ab2 and Vip3A.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Insect pests may be tested for pesticidal activity of compositions of the invention in early developmental stages, e.g., as larvae or other immature forms. The insects may be reared in total darkness at from about 20° C. to about 30° C. and from about 30% to about 70% relative humidity. Bioassays may be performed as described in Czapla and Lang (1990) *J. Econ. Entomol.* 83 (6): 2480-2485. See, also the experimental section herein.

III. Expression Cassettes

Polynucleotides encoding the pesticidal proteins provided herein can be provided in expression cassettes for expression in an organism of interest. The cassette will include 5' and 3' regulatory sequences operably linked to a polynucleotide encoding a pesticidal polypeptide provided herein that allows for expression of the polynucleotide. The cassette may additionally contain at least one additional gene or genetic element to be cotransformed into the organism. Where additional genes or elements are included, the components are operably linked. Alternatively, the additional gene(s) or element(s) can be provided on multiple expression cassettes. Such an expression cassette is provided with a plurality of restriction sites and/or recombination sites for insertion of the polynucleotides to be under the transcriptional regulation of the regulatory regions. The expression cassette may additionally contain a selectable marker gene.

The expression cassette will include in the 5'-3' direction of transcription, a transcriptional and translational initiation region (i.e., a promoter), a pesticidal polynucleotide of the invention, and a transcriptional and translational termination region (i.e., termination region) functional in the organism of interest, i.e., a plant or bacteria. The promoters of the invention are capable of directing or driving expression of a coding sequence in a host cell. The regulatory regions (i.e., promoters, transcriptional regulatory regions, and translational termination regions) may be endogenous or heterologous to the host cell or to each other. As used herein, "heterologous" in reference to a sequence is a sequence that originates from a foreign species, or, if from the same species, is substantially modified from its native form in composition and/or genomic locus by deliberate human intervention. As used herein, a chimeric gene comprises a coding sequence operably linked to a transcription initiation region that is heterologous to the coding sequence.

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional regulatory signals include, but are not limited to, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (1992) Molecular Cloning: A Laboratory Manual, ed. Maniatis et al. (Cold Spring Harbor Laboratory Press, Cold Spring Harbor, N.Y.), hereinafter "Sambrook 11"; Davis et al., eds. (1980) Advanced Bacterial Genetics (Cold Spring Harbor Laboratory Press), Cold Spring Harbor, N.Y., and the references cited therein.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, inducible, tissue-preferred, or other promoters for expression in the organism of interest. See, for example, promoters set forth in WO 99/43838 and in U.S. Pat. Nos. 8,575,425; 7,790,846; 8,147,856; 8,586832; 7,772,369; 7,534,939; 6,072,050; 5,659,026; 5,608,149; 5,608,144; 5,604,121; 5,569,597; 5,466,785; 5,399,680; 5,268,463; 5,608,142; and 6,177,611; herein incorporated by reference.

For expression in plants, constitutive promoters also include CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730). Inducible promoters include those that drive expression of pathogenesis-related proteins (PR proteins), which are induced following infection by a pathogen. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116; and WO 99/43819, herein incorporated by reference. Promoters that are expressed locally at or near the site of pathogen infection may also be used (Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977; Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; Cordero et al. (1992) *Physiol. Mol. Plant Path.* 41:189-200; U.S. Pat. No. 5,750,386 (nematode-inducible); and the references cited therein).

Wound-inducible promoters may be used in the constructions of the invention. Such wound-inducible promoters include pin II promoter (Ryan (1990) *Ann. Rev. Phytopath.* 28:425-449; Duan et al. (1996) *Nature Biotechnology* 14:494-498); wun1 and wun2 (U.S. Pat. No. 5,428,148); win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Tissue-preferred promoters for use in the invention include those set forth in Yamamoto et al. (1997) *Plant J.* 12(2):255-265; Kawamata et al. (1997) *Plant Cell Physiol.* 38(7):792-803; Hansen et al. (1997)*Mol. Gen Genet.* 254 (3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505.

Leaf-preferred promoters include those set forth in Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and include those in Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element); Sanger et al. (1990) *Plant Mol. Biol.* 14(3):433-443 (mannopine synthase (MAS) gene of *Agrobacterium tumefaciens*); and Miao et al. (1991) *Plant Cell* 3(1):11-22 (cytosolic glutamine synthetase (GS)); Bogusz et al. (1990) *Plant Cell* 2(7):633-641; Leach and Aoyagi (1991) *Plant Science* (Limerick) 79(1):69-76 (rolC and rolD); Teeri et al. (1989) *EMBO J.* 8(2):343-350; Kuster et al. (1995) *Plant Mol. Biol.* 29(4):759-772 (the VfENOD-GRP3 gene promoter); and, Capana et al. (1994) *Plant Mol. Biol.* 25(4):681-691 (rolB promoter). See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *Bio Essays* 10:108. Seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed.

For expression in a bacterial host, promoters that function in bacteria are well-known in the art. Such promoters include any of the known crystal protein gene promoters, including the promoters of any of the pesticidal proteins of the invention, and promoters specific for *B. thuringiensis* sigma factors. Alternatively, mutagenized or recombinant crystal protein-encoding gene promoters may be recombinantly engineered and used to promote expression of the novel gene segments disclosed herein.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers are known and any can be used. See, for example, U.S. Provisional application 62/094,697, filed on Dec. 19, 2014, and U.S. Provisional Application 62/189,505, filed Jul. 7, 2015, both of which are herein incorporated by reference in their entirety, which discloses glufosinate resistance sequences that can be employed as selectable markers. See, for example, PCT/US2015/066648, filed on Dec. 18, 2015, herein incorporated by reference in its entirety, which discloses glufosinate resistance sequences that can be employed as selectable markers.

IV. Methods, Host Cells and Plant Cells

As indicated, DNA constructs comprising nucleotide sequences encoding the pesticidal proteins or active variants or fragments thereof can be used to transform plants of interest or other organisms of interest. Methods for transformation involve introducing a nucleotide construct into a plant. By "introducing" is intended to introduce the nucleotide construct to the plant or other host cell in such a manner that the construct gains access to the interior of a cell of the plant or host cell. The methods of the invention do not require a particular method for introducing a nucleotide construct to a plant or host cell, only that the nucleotide construct gains access to the interior of at least one cell of the plant or the host organism. Methods for introducing nucleotide constructs into plants and other host cells are known in the art including, but not limited to, stable transformation methods, transient transformation methods, and virus-mediated methods.

The methods result in a transformed organism, such as a plant, including whole plants, as well as plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated a polynucleotide encoding at least one pesticidal polypeptide of the invention. It is recognized that other exogenous or endogenous nucleic acid sequences or DNA fragments may also be incorporated into the plant cell. *Agrobacterium*-and biolistic-mediated transformation remain the two predominantly employed approaches. However, transformation may be performed by infection, transfection, microinjection, electroporation, microprojection, biolistics or particle bombardment, electroporation, silica/carbon fibers, ultrasound mediated, PEG mediated, calcium phosphate co-precipitation, polycation DMSO technique, DEAE dextran procedure, Agro and viral mediated (Caulimoriviruses, Geminiviruses, RNA plant viruses), liposome mediated and the like.

Transformation protocols as well as protocols for introducing polypeptides or polynucleotide sequences into plants may vary depending on the type of plant or plant cell, i.e., monocot or dicot, targeted for transformation. Methods for transformation are known in the art and include those set forth in U.S. Pat. Nos. 8,575,425; 7,692,068; 8,802,934; 7,541,517; each of which is herein incorporated by reference. See, also, Rakoczy-Trojanowska, M. (2002) *Cell Mol Biol Lett.* 7:849-858; Jones et al. (2005) *Plant Methods* 1:5; Rivera et al. (2012) *Physics of Life Reviews* 9:308-345; Bartlett et al. (2008) *Plant Methods* 4:1-12; Bates, G. W. (1999) *Methods in Molecular Biology* 111:359-366; Binns and Thomashow (1988) *Annual Reviews in Microbiology* 42:575-606; Christou, P. (1992) *The Plant Journal* 2:275-281; Christou, P. (1995) *Euphytica* 85:13-27; Tzfira et al. (2004) *TRENDS in Genetics* 20:375-383; Yao et al. (2006) *Journal of Experimental Botany* 57:3737-3746; Zupan and Zambryski (1995) *Plant Physiology* 107:1041-1047; Jones et al. (2005) *Plant Methods* 1:5;

Transformation may result in stable or transient incorporation of the nucleic acid into the cell. "Stable transformation" is intended to mean that the nucleotide construct introduced into a host cell integrates into the genome of the host cell and is capable of being inherited by the progeny thereof. "Transient transformation" is intended to mean that a polynucleotide is introduced into the host cell and does not integrate into the genome of the host cell.

Methods for transformation of chloroplasts are known in the art. See, for example, Svab et al. (1990) *Proc. Nail. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

In specific embodiments, the sequences provided herein can be targeted to a specific cite within the genome of the host cell or plant cell. Such methods include, but are not limited to, meganucleases designed against the plant genomic sequence of interest (D'Halluin et al. 2013 *Plant Biotechnol J*); CRISPR-Cas9, TALENs, and other technologies for precise editing of genomes (Feng, et al. Cell Research 23:1229-1232, 2013, Podevin, et al. *Trends Biotechnology*, online publication, 2013, Wei et al., *J Gen Genomics,* 2013, Zhang et al (2013) WO 2013/026740); Cre-lox site-specific recombination (Dale et al. (1995) *Plant J* 7:649-659; Lyznik, et al. (2007) *Transgenic Plant J* 1:1-9; FLP-FRT recombination (Li et al. (2009) *Plant Physiol* 151:1087-1095); Bxb1-mediated integration (Yau et al. *Plant J*(2011) 701:147-166); zinc-finger mediated integration (Wright et al. (2005) *Plant J* 44:693-705); Cai et al. (2009) *Plant Mol Biol* 69:699-709); and homologous recombination (Lieberman-Lazarovich and Levy (2011) *Methods Mol Biol* 701: 51-65); Puchta (2002) *Plant Mol Biol* 48:173-182).

The sequence provided herein may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus Curcumis such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides. Further provided is a processed plant product or byproduct that retains the sequences disclosed herein, including for example, soymeal.

In another embodiment, the genes encoding the pesticidal proteins can be used to transform organism and thereby create insect pathogenic organisms. Such organisms include baculoviruses, fungi, protozoa, bacteria, and nematodes. Microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the pesticidal protein, and desirably, provide for improved protection of the pesticide from environmental degradation and inactivation.

Such microorganisms include archaea, bacteria, algae, and fungi. Of particular interest are microorganisms such as bacteria, e.g., *Bacillus, Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*. Fungi include yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas aeruginosa, Pseudomonas fluorescens, Serratia marcescens, Acetobacter xylinum*, Agrobacteria, *Rhodopseudomonas spheroides, Xanthomonas campestris, Rhizobium melioti, Alcaligenes entrophus, Clavibacter xyli* and *Azotobacter vinlandir* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae, Aureobasidium pollulans, Bacillus thuringiensis, Escherichia coli, Bacillus subtilis*, and the like.

Illustrative prokaryotes, both Gram-negative and gram-positive, include Enterobacteriaceae, such as *Escherichia, Erwinia, Shigella, Salmonella*, and *Proteus*; Bacillaceae; Rhizobiceae, such as *Rhizobium*; Spirillaceae, such as *Photobacterium, Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Fungi include Phycomycetes and Ascomycetes, e.g., yeast, such as *Saccharomyces* and *Schizosaccharomyces*; and Basidiomycetes yeast, such as *Rhodotorula, Aureobasidium, Sporobolomyces*, and the like.

Genes encoding pesticidal proteins can be introduced by means of electrotransformation, PEG induced transformation, heat shock, transduction, conjugation, and the like. Specifically, genes encoding the pesticidal proteins can be cloned into a shuttle vector, for example, pHT3101 (Lerecius et al. (1989) *FEMS Microbiol. Letts.* 60: 211-218. The shuttle vector pHT3101 containing the coding sequence for the particular pesticidal protein gene can, for example, be transformed into the root-colonizing *Bacillus* by means of electroporation (Lerecius et al. (1989) *FEMS Microbiol. Letts.* 60: 211-218).

Expression systems can be designed so that pesticidal proteins are secreted outside the cytoplasm of gram-negative bacteria by fusing an appropriate signal peptide to the amino-terminal end of the pesticidal protein. Signal peptides recognized by *E. coli* include the OmpA protein (Ghrayeb et al. (1984) *EMBO J*, 3: 2437-2442).

Pesticidal proteins and active variants thereof can be fermented in a bacterial host and the resulting bacteria processed and used as a microbial spray in the same manner that *Bacillus thuringiensis* strains have been used as insecticidal sprays. In the case of a pesticidal protein(s) that is secreted from *Bacillus*, the secretion signal is removed or mutated using procedures known in the art. Such mutations and/or deletions prevent secretion of the pesticidal protein(s) into the growth medium during the fermentation process. The pesticidal proteins are retained within the cell, and the cells are then processed to yield the encapsulated pesticidal proteins.

Alternatively, the pesticidal proteins are produced by introducing heterologous genes into a cellular host or through the expression of the pesticidal protein in its native cell. Expression of the heterologous gene or the native gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These pesticidal proteins may then be formulated in accordance with conventional techniques for application to the environment hosting a target pest, e.g., soil, water, and foliage of plants. See, for example U.S. Pat. No. 6,468,523 and U.S. Publication No. 20050138685, and the references cited therein. In the present invention, a transformed microorganism or the native microorganism (which includes whole organisms, cells, spore(s), pesticidal protein(s), pesticidal component(s), pest-impacting component(s), mutant(s), living or dead cells and cell components, including mixtures of living and dead cells and cell components, and including broken cells and cell components) or an isolated pesticidal protein can be prepared as a formulation and can be formulated with an acceptable carrier into a pesticidal or agricultural composition(s) that is, for example, a liquid, a suspension, a solution, an emulsion, a dusting powder, dust, pellet, granule, a dispersible granule, a wettable powder, a dry flowable, a disbursable flowable, a wettable granule, a spray dried cellular composition, an emulsifiable concentrate, an aerosol, an impregnated granule, an adjuvant, a coatable paste, spray, colloid, an aqueous solution, an oil-based solution, and also encapsulations in, for example, polymer substances.

Agricultural compositions may comprise a polypeptide, a recombinogenic polypeptide or a variant or fragment thereof, as disclosed herein or a heterologous microbe expressing the pesticidal polypeptide or the native microbe comprising the pesticidal protein. The agricultural composition disclosed herein may be applied to the environment of a plant or an area of cultivation, or applied to the plant, plant part, plant cell, or seed.

Such compositions disclosed above may further comprise the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the pesticidal proteins produced by the bacterial strains of the present invention include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate of dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as a concentrate of primary composition that requires dilution with a suitable quantity of water or other diluent before application. The pesticidal concentration will vary depending upon the nature of the particular formulation, specifically, whether it is a concentrate or to be used directly. The composition contains 1 to 98% of a solid or liquid inert carrier, and 0 to 50% or 0.1 to 50% of a surfactant. These compositions will be administered at the labeled rate for the commercial product, for example, about 0.01 lb-5.0 lb. per acre when in dry form and at about 0.01 pts.-10 pts. per acre when in liquid form.

In a further embodiment, the compositions, as well as the transformed microorganisms and pesticidal proteins, provided herein can be treated prior to formulation to prolong the pesticidal activity when applied to the environment of a target pest as long as the pretreatment is not deleterious to the pesticidal activity. Such treatment can be by chemical and/or physical means as long as the treatment does not deleteriously affect the properties of the composition(s). Examples of chemical reagents include but are not limited to halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

The terms "controlling" or "control" with regards to a plant pest refers to one or more of inhibiting or reducing the growth, feeding, fecundity, reproduction, and/or proliferation of a plant pest or killing (e.g., causing the morbidity or mortality, or reduced fecundity) of a plant pest. As such, a plant treated with a pesticidal polypeptide or protein, a composition comprising a pesticidal polypeptide or protein, and/or expressing a pesticidal polypeptide or protein provided herein may show a reduced infestation of pests, or reduced damage caused by pests by a statistically significant amount. In particular embodiments, "controlling" and "protecting" a plant from a pest refers to one or more of inhibiting or reducing the growth, germination, reproduction, and/or proliferation of a pest; and/or killing, removing, destroying, or otherwise diminishing the occurrence, and/or activity of a pest. As such, a plant treated with a pesticidal protein provided herein and/or a plant expressing a pesticidal protein provided herein may show a reduced severity or reduced development of disease or damage in the presence of plant pests by a statistically significant amount.

Provided herein are methods of controlling insect pest damage to a plant, comprising expressing in a plant or cell thereof a nucleic acid molecule that encodes a pesticidal polypeptide provided herein. Also provided are methods of controlling a plant pest and/or damage caused by a plant pest comprising applying to a plant having a plant pest and/or damage an effective amount of at least one pesticidal polypeptide provided herein or an active variant thereof, and/or a composition derived therefrom wherein the pesticidal polypeptide and/or the composition derived therefrom controls a plant pest that causes the plant disease or damage. In particular embodiments, the plant damage is caused by an insect pest.

In one aspect, pests may be killed or reduced in numbers in a given area by application of the pesticidal proteins provided herein to the area. Alternatively, the pesticidal proteins may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations or compositions may also vary with respect to climatic conditions, environmental considerations, and/or frequency of application and/or severity of pest infestation.

The active ingredients are normally applied in the form of compositions and can be applied to the crop area, plant, or seed to be treated. Methods are therefore provided for providing to a plant, plant cell, seed, plant part or an area of cultivation, an effective amount of the agricultural composition comprising the polypeptide, recombinogenic polypeptide or an active variant or fragment thereof. By "effective amount" is intended an amount of a protein or composition has pesticidal activity that is sufficient to kill or control the pest or result in a noticeable reduction in pest growth, feeding, or normal physiological development. Such decreases in numbers, pest growth, feeding or normal development can comprise any statistically significant decrease, including, for example a decrease of about 5%, 10%, 15%, 20%, 25%, 30%, 35%, 40%, 45%, 50%, 55%, 60%, 65%, 70%, 75%, 85%, 90%, 95% or greater.

For example, the compositions may be applied to grain in preparation for or during storage in a grain bin or silo, etc. The compositions may be applied simultaneously or in succession with other compounds. Methods of applying an active ingredient or an agrochemical composition comprising at least one of the polypeptides, recombinogenic polypeptides or variants or fragments thereof as disclosed herein, include but are not limited to, foliar application, seed coating, and soil application.

Methods for increasing plant yield are provided. The methods comprise providing a plant or plant cell expressing a polynucleotide encoding the pesticidal polypeptide sequence disclosed herein and growing the plant or a seed thereof in a field infested with (or susceptible to infestation by) a pest against which said polypeptide has pesticidal activity. In some embodiments, the polypeptide has pesticidal activity against a lepidopteran, coleopteran, dipteran, hemipteran, or nematode pest, and said field is infested with a lepidopteran, hemipteran, coleopteran, dipteran, or nematode pest. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence. In specific methods, plant yield is increased as a result of improved pest resistance of a plant expressing a pesticidal protein disclosed herein. Expression of the pesticidal protein results in a reduced ability of a pest to infest or feed.

Further provided is a method for protecting a plant from an insect pest, comprising expressing in a plant or cell thereof a nucleotide sequence that encodes a pesticidal polypeptide, wherein the nucleotide sequence comprises (a) a nucleotide sequence that encodes a polypeptide comprising the amino acid sequence of any one of SEQ ID NOs: 2, 4, 6, 8, 10, 12, 14, 16, 18, 20, 22, 24, 26, 28, 30, 32, 34, 36, 38, and/or 40; or, (b) a nucleotide sequence that encodes a polypeptide comprising an amino acid sequence having at least the percent sequence identity set forth in Table 1 to an amino acid sequence selected from the group consisting of sequences set forth in SEQ ID NOs: 2, 4, 6, 8, 10, 12, 14, 16, 18, 20, 22, 24, 26, 28, 30, 32, 34, 36, 38, and/or 40.

The plants can also be treated with one or more chemical compositions, including one or more herbicide, insecticides, or fungicides.

In certain embodiments the polynucleotides of the present invention, including those set forth in SEQ ID NOs: 1, 3, 5, 7, 9, 11, 13, 15, 17, 19, 21, 23, 25, 27, 29, 31, 33, 35, 37, and/or 39, can be stacked with any combination of polynucleotide sequences of interest in order to create plants with a desired trait. A trait, as used herein, refers to the phenotype derived from a particular sequence or groups of sequences. For example, the polynucleotides of the present invention may be stacked with any other polynucleotides encoding polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593,881; and Geiser et al. (1986) *Gene* 48:109), lectins (Van Damme et al. (1994) *Plant Mol. Biol.* 24:825, pentin (described in U.S. Pat. No. 5,981,722), and the like. The combinations generated can also include multiple copies of any one of the polynucleotides provided herein. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)); the disclosures of which are herein incorporated by reference.

The polynucleotides of the present invention can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Non-limiting embodiments include:

1. A polypeptide having pesticidal activity, comprising
   (a) an amino acid sequence selected from the group consisting of sequences set forth in SEQ ID NOs: 2, 4, 6, 8, 10, 12, 14, 16, 18, 20, 22, 24, 26, 28, 30, 32, 34, 36, 38, and 40; or
   (b) an amino acid sequence having at least the percent sequence identity set forth in Table 1 to an amino acid sequence selected from the group consisting of sequences set forth in SEQ ID NOs: 2, 4, 6, 8, 10, 12, 14, 16, 18, 20, 22, 24, 26, 28, 30, 32, 34, 36, 38, and 40.

2. The polypeptide of embodiment 1, wherein said polypeptide comprises the amino acid sequence set forth in SEQ ID NOs: 2, 4, 6, 8, 10, 12, 14, 16, 18, 20, 22, 24, 26, 28, 30, 32, 34, 36, 38, or 40.

3. The polypeptide of embodiment 1 or 2, wherein the polypeptide is an isolated polypeptide.

4. The polypeptide of embodiment 1 or 2, wherein the polypeptide is a recombinant polypeptide.

5. A composition comprising the polypeptide of any one of embodiments 1-4.

6. The polypeptide of embodiment 2, further comprising heterologous amino acid sequences.

7. A nucleic acid molecule that encodes the polypeptide of embodiment 1.

8. The nucleic acid molecule of embodiment 7, wherein the nucleic acid molecule is an isolated nucleic acid molecule.

9. The nucleic acid molecule of embodiment 7, wherein the nucleic acid molecule is a recombinant nucleic acid molecule.

10. The recombinant nucleic acid of any one of embodiments 7-9, wherein said nucleic acid molecule is a synthetic sequence that has been designed for expression in a plant.

11. The nucleic acid molecule of embodiment 10, wherein said nucleic acid molecule is operably linked to a promoter capable of directing expression in a plant cell.

12. The nucleic acid molecule of embodiment 7, wherein said nucleic acid molecule is operably linked to a promoter capable of directing expression in a bacterium.

13. A host cell that contains the nucleic acid molecule of embodiment 12.

14. The host cell of embodiment 13, wherein said host cell is a bacterial host cell.

15. A DNA construct comprising a heterologous promoter or a heterologous promoter that drives expression in a plant cell operably linked to a recombinant nucleic acid molecule comprising
   (a) a nucleotide sequence that encodes a polypeptide comprising the amino acid sequence of any one of SEQ ID NOs: 2, 4, 6, 8, 10, 12, 14, 16, 18, 20, 22, 24, 26, 28, 30, 32, 34, 36, 38, or 40; or,
   (b) a nucleotide sequence that encodes a polypeptide comprising an amino acid sequence having at least the percent sequence identity set forth in Table 1 to an amino acid sequence selected from the group consisting of sequences set forth in SEQ ID NOs: 2, 4, 6, 8, 10, 12, 14, 16, 18, 20, 22, 24, 26, 28, 30, 32, 34, 36, 38, and 40.

16. The DNA construct of embodiment 15, wherein said nucleotide sequence is a synthetic DNA sequence that has been designed for expression in a plant.

17. A vector comprising the DNA construct of embodiment 15.

18. A host cell that contains the DNA construct of any one of embodiments 15-17.

19. The host cell of embodiment 18, wherein the host cell is a plant cell.

20. A transgenic plant comprising the host cell of embodiment 19.

21. A composition comprising the host cell of embodiment 14.

22. The composition of embodiment 21, wherein said composition is selected from the group consisting of a powder, dust, pellet, granule, a wettable granule, a disbursable flowable, a wettable powder, spray, emulsion, colloid, an aqueous solution, an oil-based solution, or a liquid.

23. The composition of embodiment 21, wherein said composition comprises from about 1% to about 99% by weight of said polypeptide.

24. A method for controlling a pest population comprising contacting said population with a pesticidal-effective amount of the composition of embodiment 21.

25. A method for killing a pest population comprising contacting said population with a pesticidal-effective amount of the composition of embodiment 21.

26. A method for producing a polypeptide with pesticidal activity, comprising culturing the host cell of embodiment 13 under conditions in which the nucleic acid molecule encoding the polypeptide is expressed.

27. A plant having stably incorporated into its genome a DNA construct comprising a nucleic acid molecule that encodes a protein having pesticidal activity, wherein said nucleic acid molecule comprises
   (a) a nucleotide sequence that encodes a polypeptide comprising the amino acid sequence of any one of SEQ ID NOs: 2, 4, 6, 8, 10, 12, 14, 16, 18, 20, 22, 24, 26, 28, 30, 32, 34, 36, 38, or 40; or,
   (b) a nucleotide sequence that encodes a polypeptide comprising an amino acid sequence having at least the percent sequence identity set forth in Table 1 to an amino acid sequence selected from the group consisting of sequences set forth in SEQ ID NOs: 2, 4, 6, 8, 10, 12, 14, 16, 18, 20, 22, 24, 26, 28, 30, 32, 34, 36, 38, and 40.

28. A transgenic seed of the plant of embodiment 27.

29. A method for protecting a plant from an insect pest, comprising expressing in a plant or cell thereof a nucleic acid molecule that encodes a pesticidal polypeptide, wherein said nucleic acid molecule comprises
(a) a nucleotide sequence that encodes a polypeptide comprising the amino acid sequence of any one of SEQ ID NOs: 2, 4, 6, 8, 10, 12, 14, 16, 18, 20, 22, 24, 26, 28, 30, 32, 34, 36, 38, or 40; or,
(b) a nucleotide sequence that encodes a polypeptide comprising an amino acid sequence having at least the percent sequence identity set forth in Table 1 to an amino acid sequence selected from the group consisting of sequences set forth in SEQ ID NOs: 2, 4, 6, 8, 10, 12, 14, 16, 18, 20, 22, 24, 26, 28, 30, 32, 34, 36, 38, and 40.

30. The method of embodiment 29, wherein said plant produces a pesticidal polypeptide having pesticidal activity against a lepidopteran pest, a hemipteran pest, or a coleopteran pest.

31. The method of embodiment 30, wherein said lepidopteran pest or said coleopteran pest is resistant to one or more strains of *Bacillus thuringiensis* or one or more toxin proteins produced by one or more strains of *Bacillus thuringiensis*.

32. The method of embodiment 31, wherein said lepidopteran pest or said coleopteran pest is resistant to any one of Cry34/Cry35, Cry3Bb, Cry2Ab2, and Vip3A.

33. A method for increasing yield in a plant comprising growing in a field a plant or seed thereof having stably incorporated into its genome a DNA construct comprising a promoter that drives expression in a plant operably linked to a nucleic acid molecule that encodes a pesticidal polypeptide, wherein said nucleic acid molecule comprises
(a) a nucleotide sequence that encodes a polypeptide comprising the amino acid sequence of any one of SEQ ID NOs: 2, 4, 6, 8, 10, 12, 14, 16, 18, 20, 22, 24, 26, 28, 30, 32, 34, 36, 38, or 40; or,
(b) a nucleotide sequence that encodes a polypeptide comprising an amino acid sequence having at least the percent sequence identity set forth in Table 1 to an amino acid sequence selected from the group consisting of sequences set forth in SEQ ID NOs: 2, 4, 6, 8, 10, 12, 14, 16, 18, 20, 22, 24, 26, 28, 30, 32, 34, 36, 38, and 40.

34. A method of obtaining a polynucleotide that encodes an improved polypeptide comprising pesticidal activity is provided, wherein the improved polypeptide has at least one improved property over any one of SEQ ID NOs: 2, 4, 6, 8, 10, 12, 14, 16, 18, 20, 22, 24, 26, 28, 30, 32, 34, 36, 38, or 40 comprising:
(a) recombining a plurality of parental polynucleotides comprising SEQ ID NOs: 1, 3, 5, 7, 9, 11, 13, 15, 17, 19, 21, 23, 25, 27, 29, 31, 33, 35, 37, or 39 or an active variant or fragment thereof to produce a library of recombinant polynucleotides encoding recombinant pesticidal polypeptides;
(b) screening the library to identify a recombinant polynucleotide that encodes an improved recombinant pesticidal polypeptide that has an enhanced property improved over the parental polynucleotide;
(c) recovering the recombinant polynucleotide that encodes the improved recombinant pesticidal polypeptide identified in (b); and,
(d) repeating steps (a), (b) and (c) using the recombinant polynucleotide recovered in step (c) as one of the plurality of parental polynucleotides in repeated step (a).

The following examples are offered by way of illustration and not by way of limitation.

EXPERIMENTAL

Example 1: Discovery of Novel Genes by Sequencing and DNA Analysis

Microbial cultures were grown in liquid culture in standard laboratory media. Cultures were grown to saturation (16 to 24 hours) before DNA preparation. DNA was extracted from bacterial cells by detergent lysis, followed by binding to a silica matrix and washing with an ethanol buffer. Purified DNA was eluted from the silica matrix with a mildly alkaline aqueous buffer.

DNA for sequencing was tested for purity and concentration by spectrophotometry. Sequencing libraries were prepared using the Nextera XT library preparation kit according to the manufacturer's protocol. Sequence data was generated on a HiSeq 2000 according to the Illumina HiSeq 2000 System User Guide protocol.

Sequencing reads were assembled into draft genomes using the CLC Bio Assembly Cell software package. Following assembly, gene calls were made by several methods and resulting gene sequences were interrogated to identify novel homologs of pesticidal genes. Novel genes were identified by BLAST, by domain composition, and by pairwise alignment versus a target set of pesticidal genes. A summary of such sequences is set forth in Table 1.

Genes identified in the homology search were amplified from bacterial DNA by PCR and cloned into bacterial expression vectors containing fused in-frame purification tags. Cloned genes were expressed in *E. coli* and purified by column chromatography. SEQ ID NOs: 1, 5, and 27 were each successfully expressed transiently. Purified proteins were assessed in insect diet bioassay studies to identify active proteins.

Example 2. Heterologous Expression in *E. Coli*

Each open reading frame set forth in Table 4 is cloned into an *E. coli* expression vector containing a maltose binding protein (pMBP). The expression vector is transformed into BL21*RIPL. An LB culture supplemented with carbenicillin is inoculated with a single colony and grown overnight at 37° C. using 0.5% of the overnight culture, a fresh culture is inoculated and grown to logarithmic phase at 37° C. The culture is induced using 250 mM IPTG for 18 hours at 16° C. The cells are pelleted and resuspended in 10 mM Tris pH7.4 and 150 mM NaCl supplemented with protease inhibitors. The protein expression is evaluated by SDS-PAGE.

Example 3. Pesticidal Activity Against Coleopteran and Lepidoptera

Methods

Protein Expression: Each sequence set forth in Table 4 was expressed in *E. coli* as described in Example 2. 400 mL of LB was inoculated and grown to an OD600 of 0.6. The culture was induced with 0.25 mM IPTG overnight at 16° C. The cells were spun down and the cell pellet was resuspended in 5 mL of buffer. The resuspension was sonicated for 2 min on ice.

Bioassay: Velvetbean Caterpillar (VBC), Fall army worm (FAW), corn ear worm (CEW), European corn borer (ECB) southwestern corn borer (SWCB), soybean looper (SBL), and diamond backed moth (DBM or Px) eggs were purchased from a commercial insectary (Benzon Research Inc., Carlisle, Pa.). The VBC, FAW, CEW, ECB and BCW eggs were incubated to the point that eclosion would occur within 12 hrs of the assay setup. ECB, SWCB and DBM were introduced to the assay as neonate larvae. Assays were carried out in 24-well trays containing multispecies lepidopteran diet (Southland Products Inc., Lake Village, Ariz.). Samples of the sonicated lysate were applied to the surface of the diet (diet overlay) and allowed to evaporate and soak into the diet. For CEW, FAW, BCW, ECB and SWCB, a 125 μl of sonicated lysate was added to the diet surface and dried. For DBM, 50 μl of a 1:2 dilution of sonicated lysate was added to the diet surface. The bioassay plates were sealed with a plate sealing film vented with pin holes. The plates were incubated at 26° C. at 65% relative humidity (RH) on a 16:8 day:night cycle in a Percival for 5 days. The assays were assessed for level of mortality, growth inhibition and feeding inhibition.

For the western corn rootworm bioassay, northern corn rootworm (NCRW), and southern corn rootworm (SCRW) bioassays, the protein construct/lysate was evaluated in an insect bioassay by dispensing 60 μl volume on the top surface of diet in well/s of 24-well plate (Cellstar, 24-well, Greiner Bio One) and allowed to dry. Each well contained 500 μl diet (Marrone et al., 1985). Fifteen to twenty neonate larvae were introduced in each well using a fine tip paint brush and the plate was covered with membrane (Viewseal, Greiner Bio One). The bioassay was stored at ambient temperature and scored for mortality, and/or growth/feeding inhibition at day 4 or day 5.

For Colorado Potato Beetle (CPB) a cork bore size No. 8 leaf disk is excised from potato leaf and is dipped in the protein construct/lysate until thoroughly wet and placed on top of filter disk (Millipore, glass fiber filter, 13 mm). Sixty μl dH$_2$O is added to each filter disk and placed in each well of 24-well plate (Cellstar, 24-well, Greiner Bio One). The leaf disk is allowed to dry and five to seven first instar larvae are introduced in each well using a fine tip paint brush. The plate is covered with membrane (Viewseal, Greiner Bio One) and small hole is punctured in each well of the membrane. The construct is evaluated with four replicates, and scored for mortality and leaf damage on day 3.

Table 3 provides a summary of pesticidal activity against coleopteran and lepidoptera of the various sequences. Table code: "–" indicates no activity seen; "+" indicates pesticidal activity; "NT" indicates not tested; "S" indicates stunt; "SS" indicates slight stunt; "LF" indicates low feeding; "M" indicates mortality.

and the fractions were analyzed for purity by SDS-PAGE. The purified protein was then tested on susceptible insects as a surface treatment in a diet-based assay as described above. The results are shown in Table 4.

TABLE 4

LC50 analysis for pesticidal activity

| APG# | Target Organism (Insect) | LC50 (μg/cm$^2$) | 95% Confidence Interval (μg/cm$^2$) |
|---|---|---|---|
| APG06396.0 | WCR | 7.8 μg/cm$^2$ | 7.4-8.3 |
| APG03548.1 | WCR | 2.8 μg/cm$^2$ | 1.8-4.1 |
| APG03083.1 | CEW | 10.1 μg/cm$^2$ | 0.2-22.1 |

Example 4. Pesticidal Activity Against Hemipteran

Protein Expression: Each of the sequences set forth in Table 4 is expressed in E. coli as described in Example 2. 400 mL of LB is inoculated and grown to an OD600 of 0.6. The culture is induced with 0.25 mM IPTG overnight at 16° C. The cells are spun down and the cell pellet is re-suspended in 5 mL of buffer. The resuspension is sonicated for 2 min on ice.

Second instar southern green stink bug (SGSB) are obtained from a commercial insectary (Benzon Research Inc., Carlisle, Pa.). A 50% v/v ratio of sonicated lysate sample to 20% sucrose is employed in the bioassay. Stretched parafilm is used as a feeding membrane to expose the SGSB to the diet/sample mixture. The plates are incubated at 25° C.:21° C., 16:8 day:night cycle at 65% RH for 5 days.

Mortality is scored for each sample.

Example 5. Transformation of Soybean

DNA constructs comprising each of SEQ ID NOs: 1, 3, 5, 7, 9, 11, 13, 15, 17, 19, 21, 23, 25, 27, 29, 31, 33, 35, 37, or 39, or active variants or fragments thereof operably linked to a promoter active in a plant are cloned into transformation vectors and introduced into Agrobacterium as described in U.S. Provisional Application No. 62/094,782, filed Dec. 19, 2015, herein incorporated by reference in its entirety.

Four days prior to inoculation, several loops of Agrobacterium are streaked to a fresh plate of YEP* medium supplemented with the appropriate antibiotics** (spectinomycin, chloramphenicol and kanamycin). Bacteria are grown for two days in the dark at 28° C. After two days,

TABLE 3

Summary of Pesticidal Activity against Coleopteran and Lepidopteran

| APG | Seq ID | SBL | VBC | FAW | CEW | BCW | ECB | SWCB | CPB | NCRW | SCRW | WCR Mortality |
|---|---|---|---|---|---|---|---|---|---|---|---|---|
| APG06396.0 | 2 | + | + | – | – | – | – | – | NT | + | NT | 100% |
| APG03083.1 | 6 | + | + | + | + | + | + | + | NT | NT | NT | – |
| APG05736.2 | 12 | NT | – | – | – | NT | NT | NT | NT | NT | NT | 80-100% |
| APG03548.1 | 28 | NT | – | – | – | NT | NT | NT | NT | + | NT | 80-100% |
| APG03548.2 | 30 | NT | – | – | – | NT | NT | NT | NT | NT | NT | 60-80% |

LC50 Analysis

A 6×His construct comprising SEQ ID NO: 2, 6, or 28 was produced. The construct was transformed into E. coli BL21*(DE3) for protein production. The proteins were purified using standard techniques for a HIS-tagged protein several loops of bacteria are transferred to 3 ml of YEP liquid medium with antibiotics in a 125 ml Erlenmeyer flask. Flasks are placed on a rotary shaker at 250 RPM at 28° C. overnight. One day before inoculation, 2-3 ml of the overnight culture were transferred to 125 ml of YEP with antibiotics in a 500 ml Erlenmeyer flask. Flasks are placed on a rotary shaker at 250 RPM at 28° C. overnight.

Prior to inoculation, the OD of the bacterial culture is checked at OD 600. An OD of 0.8-1.0 indicates that the culture is in log phase. The culture is centrifuged at 4000 RPM for 10 minutes in Oakridge tubes. The supernatant is discarded and the pellet is re-suspended in a volume of Soybean Infection Medium (SI) to achieve the desired OD. The cultures are held with periodic mixing until needed for inoculation.

Two or three days prior to inoculation, soybean seeds are surface sterilized using chlorine gas. In a fume hood, a petri dish with seeds is place in a bell jar with the lid off. 1.75 ml of 12 N HCl is slowly added to 100 ml of bleach in a 250 ml Erlenmeyer flask inside the bell jar. The lid is immediately placed on top of the bell jar. Seeds are allowed to sterilize for 14-16 hours (overnight). The top is removed from the bell jar and the lid of the petri dish is replaced. The petri dish with the surface sterilized is then opened in a laminar flow for around 30 minutes to disperse any remaining chlorine gas.

Seeds are imbibed with either sterile DI water or soybean infection medium (SI) for 1-2 days. Twenty to 30 seeds are covered with liquid in a 100×25 mm petri dish and incubated in the dark at 24° C. After imbibition, non-germinating seeds are discarded.

Cotyledonary explants are processed on a sterile paper plate with sterile filter paper dampened using SI medium employing the methods of U.S. Pat. No. 7,473,822, herein incorporated by reference.

Typically, 16-20 cotyledons are inoculated per treatment. The SI medium used for holding the explants is discarded and replaced with 25 ml of *Agrobacterium* culture (OD 620=0.8-20). After all explants are submerged, the inoculation is carried out for 30 minutes with periodic swirling of the dish. After 30 minutes, the *Agrobacterium* culture is removed.

Co-cultivation plates are prepared by overlaying one piece of sterile paper onto Soybean Co-cultivation Medium (SCC). Without blotting, the inoculated cotyledons are cultured adaxial side down on the filter paper. Around 20 explants can be cultured on each plate. The plates are sealed with Parafilm and cultured at 24° C. and around 120 µmoles m-2s-1 (in a Percival incubator) for 4-5 days.

After co-cultivation, the cotyledons are washed 3 times in 25 ml of Soybean Wash Medium with 200 mg/l of cefotaxime and timentin. The cotyledons are blotted on sterile filter paper and then transferred to Soybean Shoot Induction Medium (SSI). The nodal end of the explant is depressed slightly into the medium with distal end kept above the surface at about 45 deg. No more than 10 explants are cultured on each plate. The plates are wrapped with Micropore tape and cultured in the Percival at 24° C. and around 120 µmoles m-2s-1.

The explants are transferred to fresh SSI medium after 14 days. Emerging shoots from the shoot apex and cotyledonary node are discarded. Shoot induction is continued for another 14 days under the same conditions.

After 4 weeks of shoot induction, the cotyledon is separated from the nodal end and a parallel cut is made underneath the area of shoot induction (shoot pad). The area of the parallel cut is placed on Soybean Shoot Elongation Medium (SSE) and the explants cultured in the Percival at 24° C. and around 120 umoles m-2s-1. This step is repeated every two weeks for up to 8 weeks as long as shoots continue to elongate.

When shoots reach a length of 2-3 cm, they are transferred to Soybean Rooting Medium (SR) in a Plantcon vessel and incubated under the same conditions for 2 weeks or until roots reach a length of around 3-4 cm. After this, plants are transferred to soil.

Note, all media mentioned for soybean transformation are found in Paz et al. (2010) *Agrobacterium*-mediated transformation of soybean and recovery of transgenic soybean plants; Plant Transformation Facility of Iowa State University, which is herein incorporated by reference in its entirety. (See, agron-www.agron.iastate.edu/ptf/protocol/Soybean.pdf.)

Example 6. Transformation of Maize

Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000.times. Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842). DNA constructs designed to express the GRG proteins of the present invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Example 7. Pesticidal Activity Against Nematodes

*Heterodera* Gylcine's (Soybean Cyst Nematode) In-Vitro Assay.

Soybean Cyst Nematodes are dispensed into a 96 well assay plate with a total volume of 100 uls and 100 J2 per well. The protein of interest as set forth in any one of SEQ ID NOs: 2, 4, 6, 8, 10, 12, 14, 16, 18, 20, 22, 24, 26, 28, 30, 32, 34, 36, 38, or 40 is dispensed into the wells and held at room temperature for assessment. Finally, the 96 well plate containing the SCN J2 is analyzed for motility. Data is reported as % inhibition as compared to the controls. Hits are defined as greater or equal to 70% inhibition.

*Heterodera* Glycine's (Soybean Cyst Nematode) On-Plant Assay

Soybean plants expressing one or more of SEQ ID NOs: 2, 4, 6, 8, 10, 12, 14, 16, 18, 20, 22, 24, 26, 28, 30, 32, 34, 36, 38, or 40 are generated as described elsewhere herein. A 3-week-old soybean cutting is inoculated with 5000 SCN eggs per plant. This infection is held for 70 days and then harvested for counting of SCN cyst that has developed on the plant. Data is reported as % inhibition as compared to the controls. Hits are defined as greater or equal to 90% inhibition.

*Meloidogyne incognita* (Root-Knot Nematode) In-Vitro Assay

Root-Knot Nematodes are dispensed into a 96 well assay plate with a total volume of 100 µls and 100 J2 per well. The protein of interest comprising any one of SEQ ID NOs: 2, 4, 6, 8, 10, 12, 14, 16, 18, 20, 22, 24, 26, 28, 30, 32, 34, 36, 38, or 40 is dispensed into the wells and held at room temperature for assessment. Finally, the 96 well plate containing the RKN J2 is analyzed for motility. Data is reported as % inhibition as compared to the controls. Hits are defined as greater or equal to 70% inhibition.

*Meloidogyne incognita* (Root-Knot Nematode) On-Plant Assay

Soybean plants expressing one or more of SEQ ID NOs: 2, 4, 6, 8, 10, 12, 14, 16, 18, 20, 22, 24, 26, 28, 30, 32, 34, 36, 38, or 40 are generated as described elsewhere herein. A 3-week-old soybean is inoculated with 5000 RKN eggs per plant. This infection is held for 70 days and then harvested for counting of RKN eggs that have developed in the plant. Data is reported as % inhibition as compared to the controls. Hits are defined as greater or equal to 90% inhibition.

Example 8. Additional Assays for Pesticidal Activity

The various polypeptides set forth in SEQ ID NOs: 2, 4, 6, 8, 10, 12, 14, 16, 18, 20, 22, 24, 26, 28, 30, 32, 34, 36, 38, or 40 can be tested to act as a pesticide upon a pest in a number of ways. One such method is to perform a feeding assay. In such a feeding assay, one exposes the pest to a sample containing either compounds to be tested or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, and then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) Pesticide bioassays with arthropods, CRC, Boca Raton, Fla. Alternatively, assays are commonly described in the journals Arthropod Management Tests and Journal of Economic Entomology or by discussion with members of the Entomological Society of America (ESA). Any one of SEQ ID NOs: 2, 4, 6, 8, 10, 12, 14, 16, 18, 20, 22, 24, 26, 28, 30, 32, 34, 36, 38, or 40 can be expressed and employed in an assay as set forth in Examples 3 and 4, herein.

Example 9: Pesticidal Activity Against Bt Toxin Resistant Insects

To determine if the pesticidal proteins have a new mode-of-action from field-evolved resistant insects, lysate was tested on field-evolved resistant insects.

WCRW—Diet overlay bioassay was performed on Cry34/35-R, Cry3Bb-R and susceptible WCR (SUS) neonate larvae to assess APG06396.0 and APG03548.1 protein toxicity at 5 days. Samples of whole cell *E. coli* expressing protein, inactive proteins (negative controls), and active protein, Cry34/34 (positive control), were prepared by pelleting and resuspending the cells in different volumes of LB media. The doses were equivalent to 0.25, 0.5, 1, 2, and 3 times the cell concentration of the initial bacterial culture. LB media was also included as a negative control. WCR-M02, a semi-solid agar based artificial diet (Huynh et al., 2019, *Sci. Rep.* 9: 16009), was prepared and dispensed into each well of 96-well tissue culture plates. Samples were applied to the diet and air dried in a biological safety cabinet. A single neonate larva, hatched from surface sterilized WCR egg (Ludwick et al., 2018, *Sci. Rep.* 8: 5379), was placed in each well. Each sample was tested against 24 neonate larvae across 3 replicates. Adhesive membranes sealed each well and pin holes were made to allow airflow. The bioassay plates were stored in a dark environmental chamber at approximately 25° C.

At 5 days, the assay was evaluated. Mortality was determined and the surviving larvae were collected in vials of ethanol. The larvae were placed in a drying oven and then weighed with Sartorius microscale to estimate dry weights.

Lepidopterans—Diet overlay bioassays were performed on Cry2Ab2-R CEW, Vip3A-R FAW and susceptible populations of CEW and FAW to assess APG03083.1 protein toxicity at 7 days. Samples of whole cell *E. coli* expressing the protein and inactive protein, were prepared by pelleting and resuspending the cells in different volumes of 20 mM sodium carbonate buffer. The doses tested were equivalent to 1 and 3 times the cell concentration of the original bacterial culture. 20 mM sodium carbonate was included as a negative buffer control. Purified proteins at the diagnostic dose, Cry2Ab2 (10 µg/cm$^2$) and Vip3A (6 µg/cm$^2$), were included as positive controls. A semi-solid lepidopteran diet was prepared and dispensed into the cells of a 128-cell insect bioassay tray. Then 100 µl of each sample was applied to the diet and air dried in a biological safety cabinet. A single neonate larva, less than 12 hours old, was placed in each well. Adhesive membranes with a clear perforated window per cell for gas/moisture exchange sealed each cell. The bioassay trays were kept in an environmental chamber at approximately 27° C.

At 7-days, the assay was evaluated for larval mortality and the developmental stadia of the larvae were determined.

The results of the assays are shown in Table 5.

TABLE 5

Pesticidal Activity Against Bt Toxin Resistant Insects

| APG# | Seq ID No. | Target (Insect) | Concentration | Activity |
|---|---|---|---|---|
| APG06396.0 | 2 | susceptible WCRW | 3× | + |
| APG06396.0 | 2 | Cry3Bb-resistant WCRW | 3× | + |
| APG06396.0 | 2 | Cry34/35-resistant WCRW | 3× | + |
| APG03548.1 | 28 | susceptible WCRW | 3× | + |
| APG03548.1 | 28 | Cry3Bb-resistant WCRW | 3× | + |
| APG03548.1 | 28 | Cry34/35-resistant WCRW | 3× | + |
| APG03083.1 | 6 | susceptible FAW | 3× | + |
| APG03083.1 | 6 | Vip3A-resistant FAW | 3× | + |
| APG03083.1 | 6 | Cry1Fa-resistant FAW | 3× | + |

TABLE 5-continued

Pesticidal Activity Against Bt Toxin Resistant Insects

| APG# | Seq ID No. | Target (Insect) | Concentration | Activity |
|---|---|---|---|---|
| APG03083.1 | 6 | susceptible CEW | 3× | + |
| APG03083.1 | 6 | Cry2Ab-resistant CEW | 3× | + |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed is:

1. A recombinant nucleic acid molecule encoding a polypeptide comprising
   an amino acid sequence having at least 95% sequence identity to an amino acid sequence set forth in SEQ ID NO: 26, 28 or 30, wherein the polypeptide has pesticidal activity;
   wherein the recombinant nucleic acid molecule is operably linked to a heterologous promoter.

2. The recombinant nucleic acid molecule of claim 1, wherein the recombinant nucleic acid molecule is not a naturally occurring sequence encoding said polypeptide.

3. The recombinant nucleic acid of claim 1, wherein said recombinant nucleic acid molecule is a synthetic sequence designed for expression in a plant.

4. A host cell comprising a nucleic acid molecule encoding a polypeptide comprising
   an amino acid sequence having at least 95% sequence identity to an amino acid sequence set forth in SEQ ID NO: 26, 28 or 30, wherein the polypeptide has pesticidal activity;
   wherein said nucleic acid molecule is heterologous to said host cell.

5. The host cell of claim 4, wherein said host cell is a bacterial host cell or a plant cell.

6. A DNA construct comprising a heterologous promoter operably linked to a nucleotide sequence that encodes a polypeptide comprising
   an amino acid sequence having at least 95% sequence identity to an amino acid sequence set forth in SEQ ID NO: 26, 28 or 30, wherein the polypeptide has pesticidal activity.

7. The DNA construct of claim 6, wherein the promoter drives expression in a plant cell.

8. The DNA construct of claim 6, wherein said nucleotide sequence is a synthetic DNA sequence designed for expression in a plant.

9. The DNA construct of claim 6, wherein the promoter drives expression in a bacterial cell.

10. A vector comprising the DNA construct of claim 6.

11. A host cell comprising the DNA construct of claim 6.

12. A method for producing a polypeptide with pesticidal activity comprising culturing the host cell of claim 11 under conditions in which the nucleic acid molecule encoding the polypeptide is expressed.

13. A plant having stably incorporated into its genome a DNA construct comprising a nucleic acid molecule that encodes a protein having pesticidal activity, wherein said nucleic acid molecule comprises
    a nucleotide sequence that encodes a polypeptide comprising an amino acid sequence having at least 95% sequence identity to an amino acid sequence set forth in SEQ ID NO: 26, 28 or 30, wherein the polypeptide has pesticidal activity.

14. A transgenic seed of the plant of claim 13, wherein said seed has stably incorporated into its genome the DNA construct.

15. The plant of claim 13, wherein said pesticidal activity controls a lepidopteran pest, a hemipteran pest, or a coleopteran pest.

16. The plant of claim 13, wherein the plant is a monocot.

17. The plant of claim 13, wherein the plant is a dicot.

18. The plant of claim 16, wherein the plant is corn, sorghum, wheat, rice, sugarcane, barley, oats, rye, millet, coconut, pineapple or banana.

19. The plant of claim 17, wherein the plant is sunflower, tomato, crucifers, peppers, potato, cotton, soybean, sugarbeet, tobacco, oilseed rape, sweet potato, alfalfa, safflower, peanuts, cassava, coffee, cocoa, cucumber, lettuce, olive, peas, or tea.

20. A method for protecting a plant from an insect pest, comprising expressing in a plant or cell thereof a nucleic acid molecule that encodes a pesticidal polypeptide, wherein said nucleic acid molecule comprises
    a nucleotide sequence that encodes a polypeptide comprising an amino acid sequence having at least 95% sequence identity to an amino acid sequence set forth in SEQ ID NO: 26, 28 or 30, wherein the polypeptide has pesticidal activity.

21. The method of claim 20, wherein protecting said plant comprises controlling insect pest damage to said plant.

22. A method for increasing yield in a plant comprising growing in a field a plant or seed thereof having stably incorporated into its genome a DNA construct comprising a promoter that drives expression in a plant operably linked to a nucleic acid molecule that encodes a pesticidal polypeptide, wherein said nucleic acid molecule comprises a nucleotide sequence that encodes a polypeptide comprising an amino acid sequence having at least 95% sequence identity to an amino acid sequence set forth in SEQ ID NO: 26, 28 or 30, wherein the polypeptide has pesticidal activity.

23. The method of claim 20, wherein said plant produces a pesticidal polypeptide having pesticidal activity against a lepidopteran pest, a hemipteran pest, or a coleopteran pest.

24. The method of claim 23, wherein said lepidopteran pest or said coleopteran pest is resistant to one or more strains of *Bacillus thuringiensis* or one or more toxin proteins produced by one or more strains of *Bacillus thuringiensis*.

25. The method of claim 24, wherein said lepidopteran pest or said coleopteran pest is resistant to any one of Cry34/Cry35, Cry3Bb, Cry2Ab2, and Vip3A.

26. The method of claim 20, wherein the plant is a monocot.

27. The method of claim 20, wherein the plant is a dicot.

28. The method of claim 26, wherein the plant is corn, sorghum, wheat, rice, sugarcane, barley, oats, rye, millet, coconut, pineapple or banana.

29. The method of claim 27, wherein the plant is sunflower, tomato, crucifers, peppers, potato, cotton, soybean, sugarbeet, tobacco, oilseed rape, sweet potato, alfalfa, safflower, peanuts, cassava, coffee, cocoa, cucumber, lettuce, olive, peas, or tea.

30. The recombinant nucleic acid molecule of claim 1, wherein the recombinant nucleic acid molecule encodes a polypeptide comprising the amino acid sequence set forth in SEQ ID NO: 26, 28 or 30.

31. The host cell of claim 4, wherein the nucleic acid molecule encodes a polypeptide comprising the amino acid sequence set forth in SEQ ID NO: 26, 28 or 30.

32. The DNA construct of claim 6, wherein the nucleotide sequence encodes a polypeptide comprising the amino acid sequence set forth in SEQ ID NO: 26, 28 or 30.

33. The plant of claim 13, wherein the nucleic acid molecule comprises a nucleotide sequence that encodes a polypeptide comprising the amino acid sequence set forth in SEQ ID NO: 26, 28 or 30.

34. The method of claim 20, wherein the nucleic acid molecule comprises a nucleotide sequence that encodes a polypeptide comprising the amino acid sequence set forth in SEQ ID NO: 26, 28 or 30.

35. The method of claim 22, wherein the nucleic acid molecule comprises a nucleotide sequence that encodes a polypeptide comprising the amino acid sequence set forth in SEQ ID NO: 26, 28 or 30.

* * * * *